(12) United States Patent
Sekiya et al.

(10) Patent No.: US 6,338,711 B1
(45) Date of Patent: Jan. 15, 2002

(54) STEREOSCOPIC ENDOSCOPE

(75) Inventors: Takaomi Sekiya; Masaru Eguchi, both of Tokyo (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/309,889

(22) Filed: May 11, 1999

Related U.S. Application Data

(62) Division of application No. 08/564,537, filed on Nov. 29, 1995, now Pat. No. 5,976,071.

(30) Foreign Application Priority Data

| Nov. 29, 1994 | (JP) | 6-319300 |
|---|---|---|
| Dec. 8, 1994 | (JP) | 6-331229 |
| Dec. 28, 1994 | (JP) | 6-340053 |
| Dec. 28, 1994 | (JP) | 6-340055 |
| Feb. 9, 1995 | (JP) | 7-044779 |
| Feb. 15, 1995 | (JP) | 7-050613 |
| Feb. 24, 1995 | (JP) | 7-061749 |
| May 10, 1995 | (JP) | 7-136043 |
| Jul. 4, 1995 | (JP) | 7-191143 |

(51) Int. Cl.$^7$ ............................................. A61B 1/06
(52) U.S. Cl. ...................... 600/166; 600/111; 348/45
(58) Field of Search ........................... 600/111, 112, 600/166; 348/73, 75; 359/477

(56) References Cited

U.S. PATENT DOCUMENTS

| 2,149,601 A | 3/1939 | Guldbransen |
| 2,595,409 A | 5/1952 | Reijnders |
| 2,929,305 A | 3/1960 | Blackstone |
| 3,457,364 A | 7/1969 | Carrillo |
| 3,495,891 A | 2/1970 | Lee |
| 4,061,135 A | * 12/1977 | Widran et al. ............... 600/166 |
| 4,295,153 A | * 10/1981 | Gibson ........................ 348/48 |
| 4,364,629 A | 12/1982 | Lang et al. |
| 4,834,518 A | 5/1989 | Barber |
| 4,862,873 A | 9/1989 | Yajima et al. |
| 4,873,572 A | 10/1989 | Miyazaki et al. |
| 5,385,138 A | 1/1995 | Berry |
| 5,522,789 A | 6/1996 | Takahashi |
| 5,527,263 A | * 6/1996 | Zobel et al. ................. 600/166 |
| 5,557,454 A | 9/1996 | Takahashi |
| 5,577,991 A | 11/1996 | Akui et al. |
| 5,702,350 A | * 12/1997 | Vry et al. .................... 600/166 |
| 5,743,847 A | * 4/1998 | Nakamura et al. .......... 600/166 |

FOREIGN PATENT DOCUMENTS

| DE | 4341975 | 7/1994 |
| FR | 502707 | 5/1930 |
| GB | 2268283 | 5/1994 |
| JP | 6-194581 | 7/1994 |
| JP | 6-202006 | 7/1994 |

* cited by examiner

*Primary Examiner*—John P. Leubecker
(74) *Attorney, Agent, or Firm*—Greenblum & Bernstein, P.L.C.

(57) ABSTRACT

An adapter uses a monocular endoscope with a stereoscopic observing portion. The observing portion includes a system that divides light transmitted by the monocular endoscope into two light beams, and a pair of optical systems, each of the optical systems receiving one of the light beams and forming an image of the object. The images formed by each of the optical systems forming a stereoscopic image of the object, the adapter comprising a system that connects the observing portion to the monocular endoscope.

4 Claims, 77 Drawing Sheets

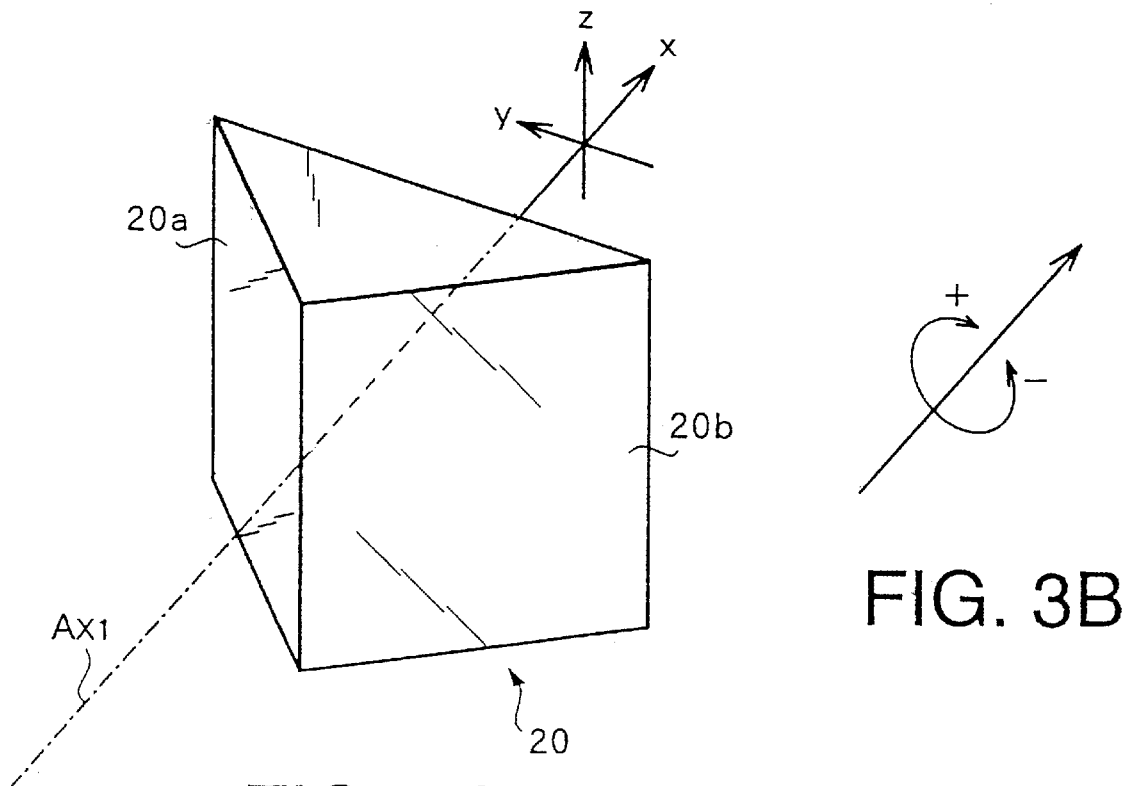
FIG. 3A
FIG. 3B
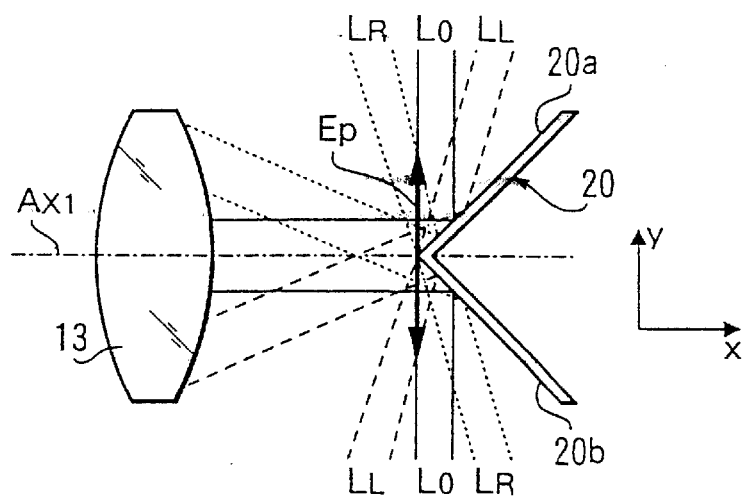
FIG. 4

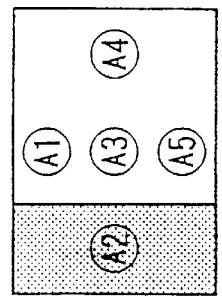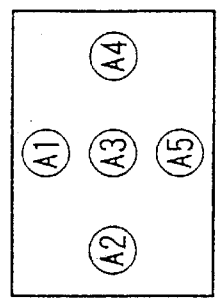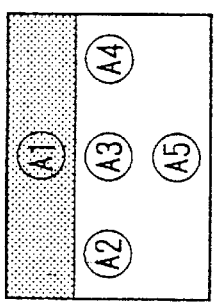
FIG. 11A  FIG. 11B  FIG. 11D
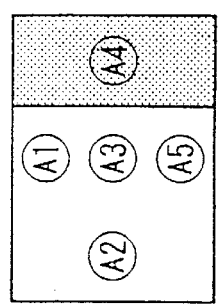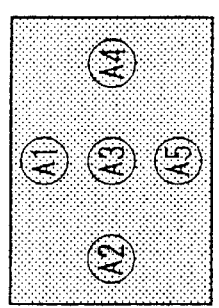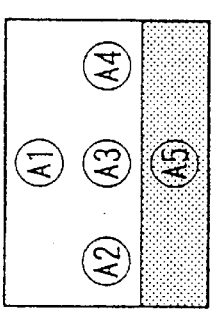
FIG. 11A  FIG. 11C  FIG. 11E FIG. 35
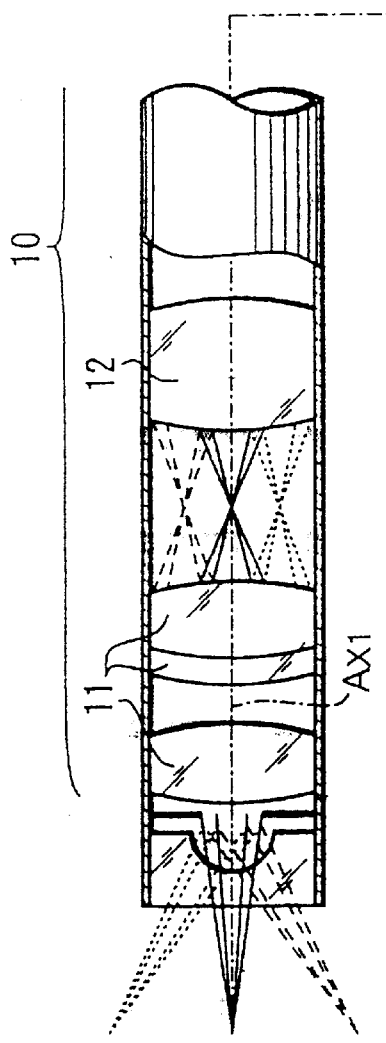
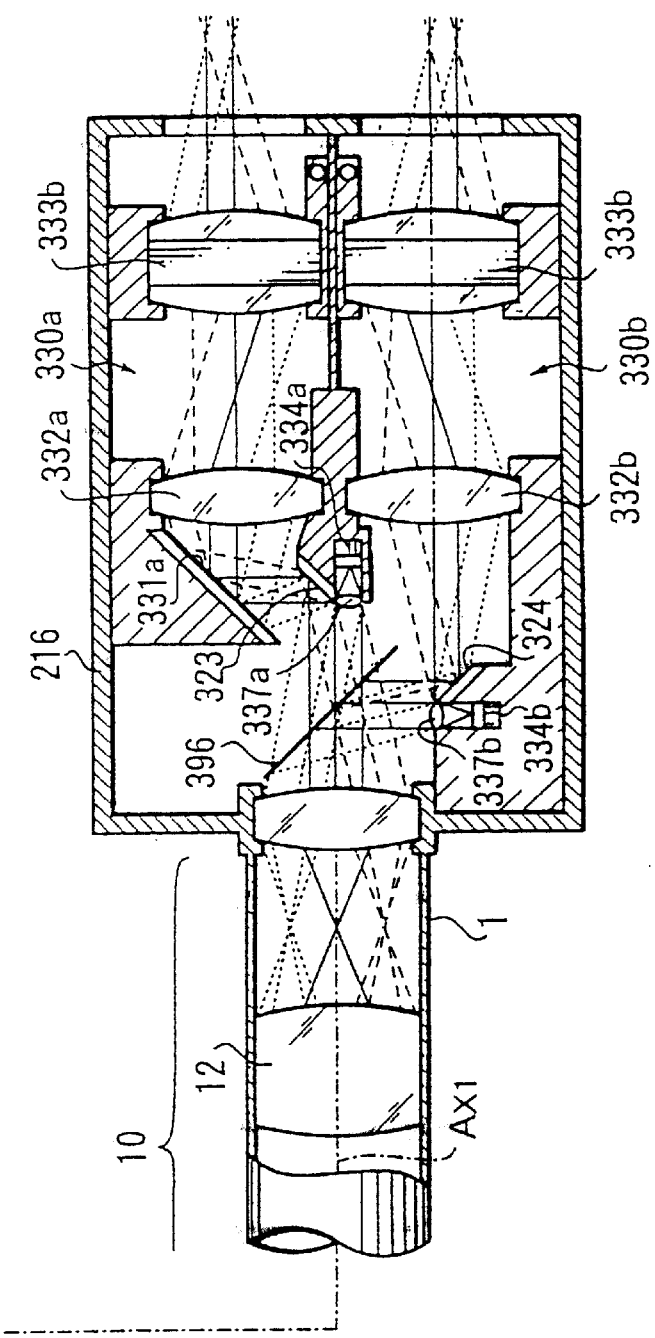

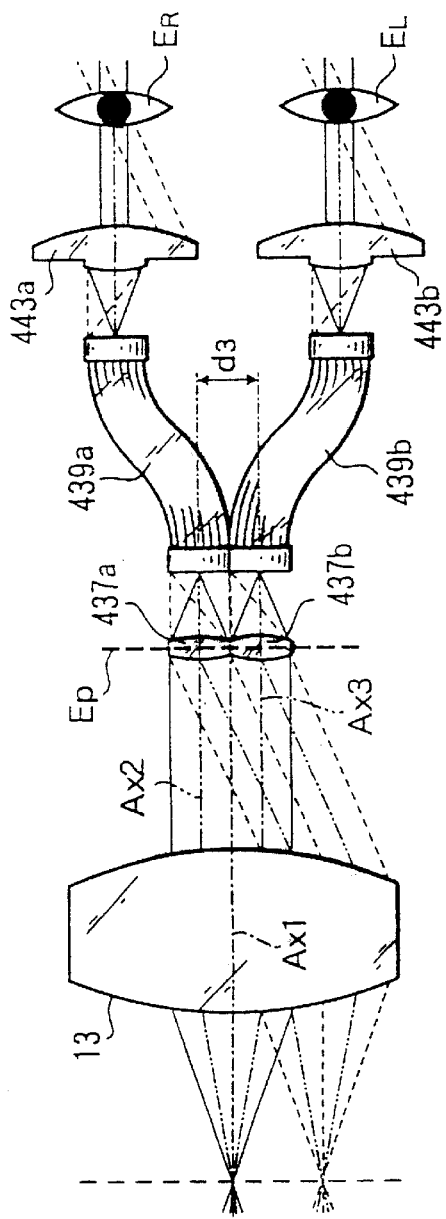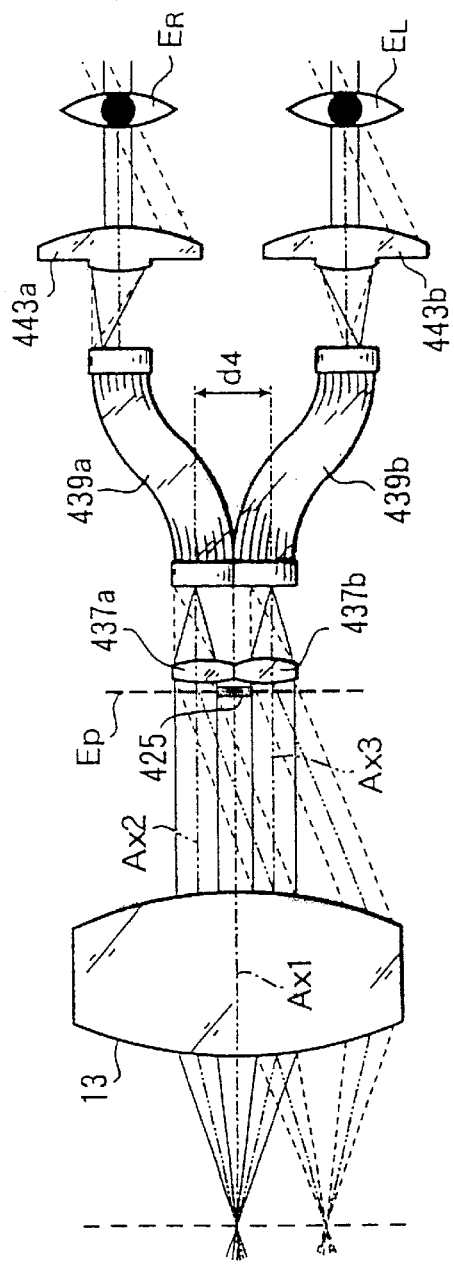

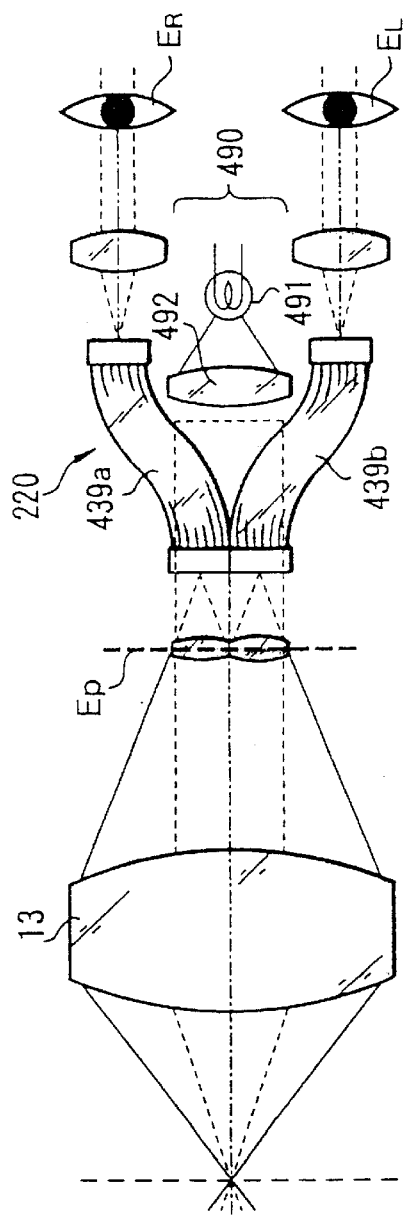
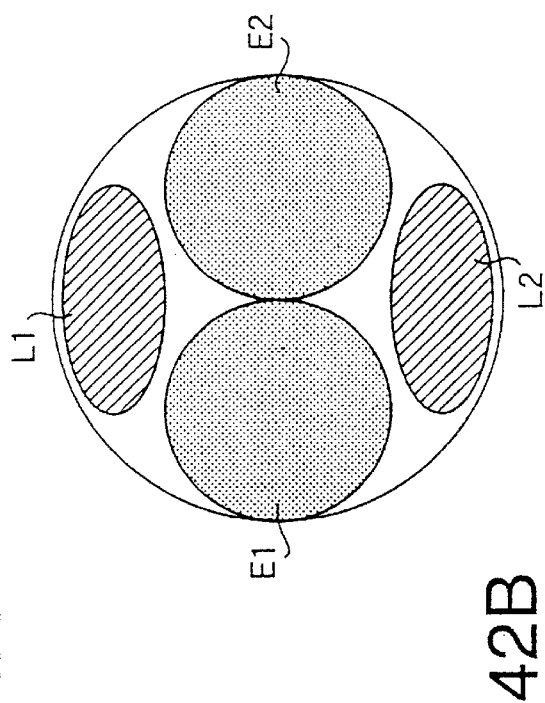
FIG. 42A
FIG. 42B

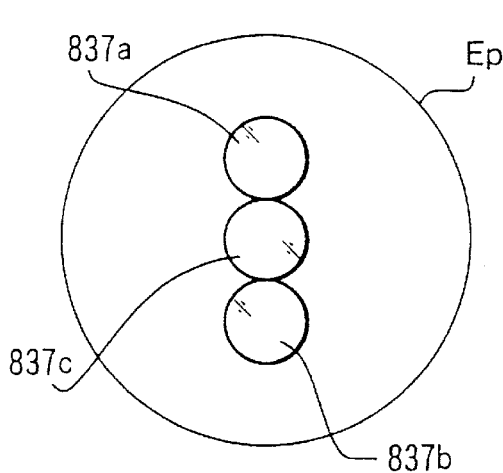
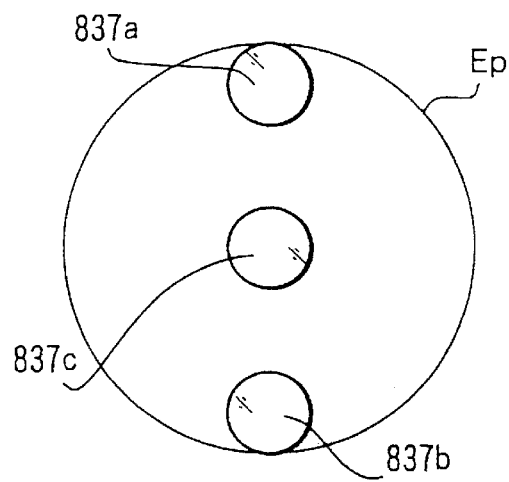
FIG. 58A　　　　　FIG. 58B
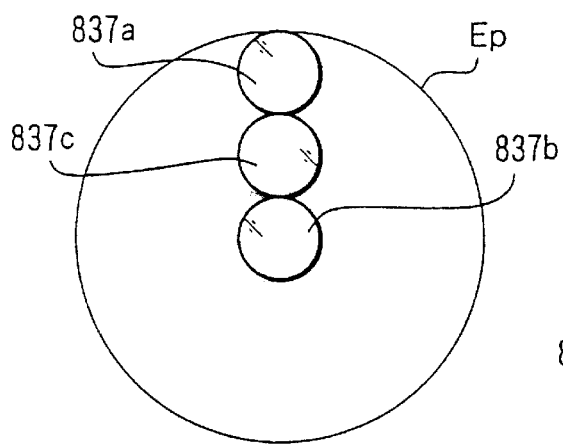
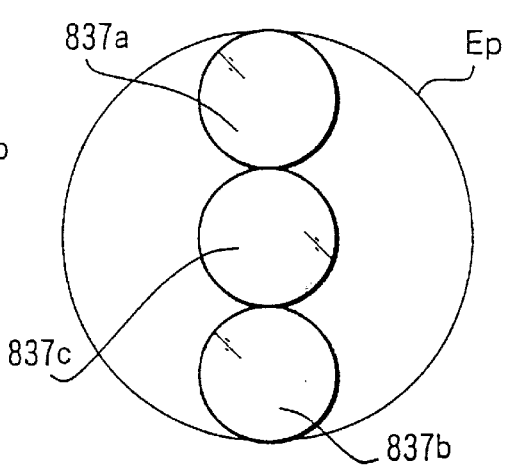
FIG. 58C　　　　　FIG. 58D

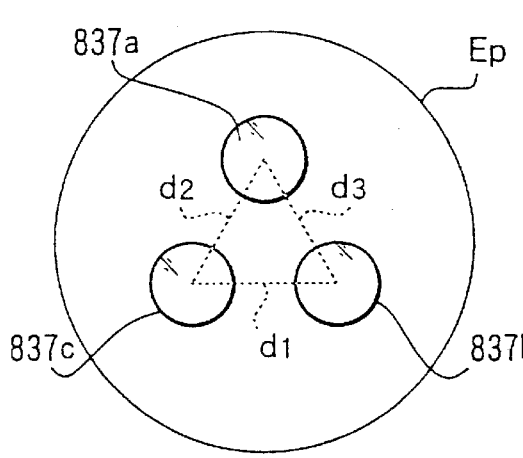
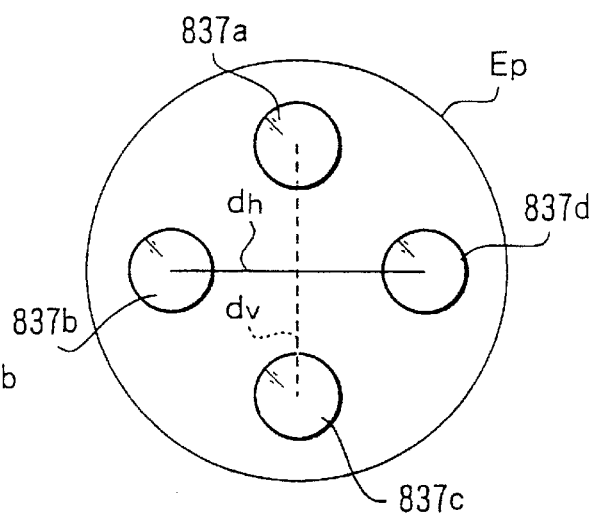
FIG. 59A    FIG. 59B
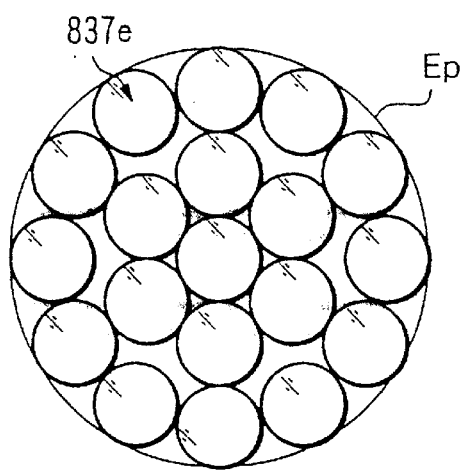
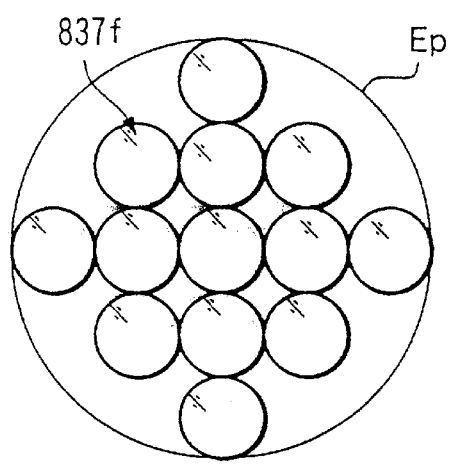
FIG. 59C    FIG. 59D

STEREOSCOPIC ENDOSCOPE

CROSS-REFERENCE TO RELATED APPLICATIONS

This is a divisional of application Ser. No. 08/564,537, filed Nov. 29, 1995, now U.S. Pat. No. 5,976,071 the contents of which are herein incorporated by reference in its entirety.

BACKGROUND OF THE INVENTION

The present invention relates to a stereoscopic endoscope which allows an observer to view a three-dimensional image of an object under test.

A stereoscopic endoscope is used to observe an object or cavity internal to a machine or the human body. Examples of rigid type stereoscopic endoscopes are disclosed in for example, U.S. Pat. No. 4,364,629 and Japanese Laid Open Publication Hei. 6-194581. In these examples, the stereoscopic endoscopes have an insertion portion which includes an objective lens for forming an image of the object and a relay lens for transmitting the light to an exit pupil of the insertion portion. The stereoscopic endoscopes also include an observing portion, which includes an optical device for splitting the light at the exit pupil and directing the split light beams to a left and right optical imaging system, through which an observer would view a three-dimensional image of the object.

However, if the optical device for splitting the light beam is not positioned correctly, the three-dimensional effect of the image may be reduced, thereby reducing the effectiveness of the endoscope. Further, even if the optical device for splitting the light beam is positioned correctly for an object located near to the insertion portion of the endoscope, the three-dimensional effect of an image of an object located far away from the insertion point of the endoscope may be reduced. This also reduces the effectiveness of the endoscope.

In conventional stereoscopic endoscopes, the three-dimensional image is viewed directly, using eyepiece lenses, or indirectly using an imaging device such as a CCD, and a video processor. Use of an imaging device allows the images to be viewed by many people, through the use of a monitor and special viewing glasses. However, this requires extra hardware and elaborate image processing. In a direct viewing endoscope, the image may be viewed easily and quickly through the eyepiece lenses, but by only one person at a time. Thus, extra time will be required if many people are to view the image.

Further, in a conventional stereoscopic endoscope that employs the imaging devices, one imaging device is used with each optical system, thereby increasing the cost of manufacturing the cost of the endosocope.

In conventional stereoscopic endoscopes the optical device for splitting the light beam uses a series of reflective surfaces in order to properly split the light beam. Therefore, the positional relationship between the various reflective surfaces must be set precisely. Further, in order properly position all of the reflective surfaces, the size of the endoscope must be made large, thereby reducing the effectiveness of the endoscope. Furthermore, the number of parts required to manufacture the endoscope is increased.

In a conventional stereoscopic endoscope, light is provided to illuminate the object by using a separate light source and an optical guide. The optical guide is housed in the insertion portion of the stereoscopic endoscope, and is parallel to the optical axis of optical system used for viewing the image. This results in the diameter of the insertion portion being large, and therefore the insertion portion cannot be as easily inserted into the cavity.

SUMMARY OF THE INVENTION

It is therefore an object of the present invention to provide an improved stereoscopic endoscope in which the position of a device for splitting the light beam, can be positioned at the standard correct position quickly and accurately.

It is another object of the present invention to provide an improved stereoscopic endoscope in which the three-dimensional effect of the image viewed using the endoscope can be changed quickly and easily.

It is a further object of the present invention to improve the utility of a stereoscopic endoscope in which the image of the object can be viewed by many people or by a single person, quickly.

It is yet a further object of the present invention to provide an improved stereoscopic endoscope in which a single imaging device is used, thereby reducing the size of the endoscope and the number of parts required to manufacture the endosocope.

It is still another object of the present invention to provide an adapter for use with a stereoscopic endoscope which allows a wide range of insertion portions of monocular endoscopes to be used with an observing portion of the stereoscopic endoscope.

It is still a further object of the present invention to provide an improved stereoscopic endoscope which can illuminate the object to be viewed without increasing the diameter of the insertion portion of the stereoscopic endoscope.

According to a first aspect of the present invention, there is provided a stereoscopic endoscope which includes: a primary optical system for transmitting light, reflected by an object located near a first end of the primary optical system; to a second end of the primary optical system, a device for dividing the light transmitted to the second end of the primary optical system into two light beams; and a pair of secondary optical systems. Each of the secondary optical systems has an imaging device which outputs an image signal. Each of the secondary optical systems receives one of the light beams and forms an image of the object on its corresponding imaging device. The stereoscopic endoscope also includes a device for adjusting a position of the light dividing device relative to an optical axis and exit pupil of the primary optical system, and a device for detecting a position of the light dividing device in accordance with each of the output image signals.

In a preferred embodiment, the detecting device detects the position of the light dividing device in accordance with a distribution of a brightness of each image formed on each of the imaging devices, by an object having a uniform brightness. Further, the stereoscopic endoscope calculates an amount and direction of movement required to move the adjusting device to a standard correct position, in accordance with the distribution of brightness of the images formed on each of the imaging devices. Therefore, the stereoscopic endoscope can automatically position the light dividing device at the standard correct position, quickly and accurately. This ensures that an image having the proper three-dimensional effect can be observed by the user.

Still preferably, the stereoscopic endoscope also includes a device for processing the image signals to produce left and right images, and a device for calculating the amount and direction of movement required to position the light dividing device at the standard correct position.

In a preferred embodiment, the processing device and the calculating device are located in a common, which is separate from the housing of the stereoscopic endoscope.

In another preferred embodiment, the processing device and the calculating device are located in separate housings. Therefore, during normal use of the stereoscopic endoscope, only the processing device needs to be attached to the stereoscopic endoscope, thereby reducing the size of the stereoscopic endoscope system.

In yet another preferred embodiment, the calculating device is provided inside the stereoscopic endoscope housing, and the processing means is provided in a separate housing. This reduces the overall size required for the stereoscopic endoscope system.

Optionally, the primary optical system is provided by a monocular endoscope, which is attached to an adapter. The adapter is then attached to an observing portion of the stereoscopic endoscope which includes the light dividing device and the pair of secondary optical systems. This permits automatic positioning of the light dividing device relative to an exit pupil of any monocular endoscope.

The position of the adapter relative to the light dividing device may be adjusted by varying a position of adjustment screws used to secure the adapter to the observing portion. Furthermore, by including motors, the adjustment of the position of the screws can be done automatically.

In another preferred embodiment, the stereoscopic endoscope includes an indicator for indicating the calculated amount and direction of movement required to position the light dividing device at the standard correct position. The adjustment of the position of the light dividing device can then be done manually using the indicated information.

In yet another preferred embodiment, a single imaging device replaces the imaging device used in each of the secondary systems. This reduces the overall cost of manufacturing the stereoscopic endoscope.

In order to further reduce the cost of manufacture, the size of the imaging device can be reduced, and the formation of the images by the two secondary optical systems on the imaging device are alternated.

The viewing of the three-dimensional image of the object may be achieved by using a monitor to alternately display the left and right images, and special glasses to alternately transmit the left and right images to the corresponding eye of the observer.

In a preferred embodiment, the light dividing device is a mirror block having two reflective surfaces which are perpendicular to each other, and arranged at a 45° angle to an optical axis of the primary optical system. Further, the adjusting device may include:

a frame for holding the mirror block;

a first screw fitted into the holding frame;

a first gear which meshes with the first screw, the first gear rotating about an axis;

a second screw fitted into a mounting member attached to the observing portion and having a nut through which the first screw is threaded; and a second gear which meshes with the second screw, the first gear rotating about another axis.

The holding frame is moved in a first plane in response to a rotation of the first gear, and is moved in a second plane in response to a rotation of the second gear, with the first plane being perpendicular to the second plane.

In an alternative embodiment, the mirror block is replaced with a pair of mirrors attached to separate supports. The pair of mirrors are arranged in a similar position relative to the primary optical axis, as the reflective surfaces of the mirror block. This reduces the need for a mirror block and results in reduction in the weight of the stereoscopic endoscope.

According to a second aspect of the present invention, there is provided a stereoscopic endoscope having an optical system for transmitting a luminous flux, reflected by an object located near a first end of the optical system, to a second of the optical system. The stereoscopic endoscope forms a first image of the object in accordance with a first area of the luminous flux, and forms a second image of the object in accordance with a second area of the luminous flux. The second area of the luminous flux does not overlap the first area of the luminous flux. The stereoscopic endoscope also includes a device for adjusting a distance between an optical axis of the first area of the luminous flux and an optical axis of the second area of the luminous flux, such that a size of the first area of the luminous flux remains equal to a size of the second area of the luminous flux.

In a preferred embodiment, the stereoscopic endoscope includes a device for guiding the first area of the luminous flux to a first device for forming a first image, and a device for guiding the second area of the luminous flux to a second device for forming the second image.

Preferably, the adjusting device includes a screw and a gear which rotates about an axis and meshes with a center of the screw. The two guiding devices are attached to separate supports, with one support threaded onto the screw on one side of the center of the screw, and the other support threaded onto the screw on the other side of the center of the screw. By rotating the gear, the supports move towards or away from each other along an axis of the screw.

Therefore, the distance between the central axis of the two portions of the luminous flux which form the first and second images, can be adjusted. Thus, the three-dimensional effect of the observed image can be adjusted, by rotating the gear.

In a preferred embodiment the guiding devices are mirrored surfaces for reflecting the first area of the luminous flux to the first image forming device, and for reflecting the second area of the luminous flux to the second image forming device.

In another preferred embodiment, each of the first and second image forming devices includes an imaging lens for forming the respective image and an eyepiece lens for viewing the image.

In yet another preferred embodiment, each of the first and second image forming devices includes an imaging lens for forming the respective image and an imaging device for detecting the image and for outputting an image signal. The imaging device can include a CCD. Optionally, each of the secondary optical systems may also have an eyepiece lens to allow simultaneous direct viewing of the image, and indirect viewing using the imaging devices.

Further optionally, the primary optical system is provided by an insertion portion of a monocular endoscope which is attached using an adapter to an observing portion of the stereoscopic endoscope. Therefore, the range of endoscopes which may be used with the apparatus having the present invention is increased.

Alternatively, each guiding device and corresponding image forming device is replaced with a separator lens and an imaging device. Each separator lens receives one of the respective portions of the luminous flux and forms an image, which is detected by the corresponding imaging device. The imaging devices output image signals, which can be processed to produce a three-dimensional image. Therefore, in this case, the adjusting device changes the distance between the optical axes of the separator lenses.

Optionally, an optical fiber bundle may be used to transfer the luminous flux from the separator lens to the corresponding imaging device. This increases the flexibility of positioning the imaging devices.

Alternatively, the imaging device is replaced with an imaging lens and an eyepiece lens for direct viewing of the three-dimensional image by an observer.

In another alternative embodiment, the stereoscopic endoscope has a single imaging device and each of separator lenses forms one of the images on the single imaging device. By employing one imaging device, the cost of manufacturing the stereoscopic endoscope can be decreased.

According to a third aspect of the present invention, there is provided a stereoscopic endoscope which includes a primary optical system for transmitting light, reflected by an object located near a first end of the primary optical system, to a second end of the primary optical system, a plurality of secondary optical systems, each of the secondary optical systems receiving a separate portion of the light and forming an image of the object; and a plurality of devices for guiding a separate portion of the light transmitted to the second end of the primary optical system, to each of the secondary optical systems. The stereoscopic endoscope also includes a device for selecting a predetermined number of the images for viewing the object. Therefore, by selecting images which are formed by secondary optical systems which are closer together or further apart, the three-dimensional effect of the observed image can be varied.

In a preferred embodiment, each of the plurality of guiding devices and corresponding plurality of secondary optical systems is replaced with a separator lens, and an imaging device. Each separator receives one of the portions of transmitted light and forms an image of the object on the corresponding imaging device. The imaging devices output image signals corresponding to the images formed by the separator lenses.

In another preferred embodiment, each of the guiding devices includes a separator lens for receiving the separate portions of the light. Further, each of the secondary optical systems includes an imaging lens, an imaging device, and an optical fiber bundle for guiding the received portions of the light from the separator lens to the imaging lens. The imaging lens forms an image on the imaging device, which outputs the image signal.

Alternatively, some of the imaging devices are replaced with eyepiece lenses to allow direct viewing of the three-dimensional image of the object. Therefore, simultaneous direct viewing using the eyepiece lenses and indirect viewing using the imaging devices is possible.

Optionally, some of the secondary optical systems are provided with an eyepiece lens, a half mirror and an imaging device. This also allows direct viewing with the eyepiece lens as well as more choices for indirectly viewing the image using the imaging devices.

Preferably, at least three secondary optical systems, and three guiding devices are provided.

In another preferred embodiment, one imaging device is provided and two secondary optical systems are provided to form two images on two areas of the single imaging device.

Optionally, each of the secondary optical systems is provided with a liquid crystal shutter, which allows or prohibits the formation of the image by the secondary optical system. Therefore, when the image is being formed by one of the secondary optical systems on the single imaging device, the liquid crystal shutter of the other secondary optical system prohibits the formation of the other image by the other secondary optical system.

In this case, the first area and second area of the single imaging device can overlap, and therefore, the size of the single imaging device can be reduced, thereby reducing the manufacturing cost of the stereoscopic endoscope.

According to a fourth aspect of the present invention, there is provided a stereoscopic endoscope which includes a primary optical system for transmitting light, reflected by an object located near a first end of the primary optical system, to a second end of the primary optical system; a prism for dividing the light transmitted to the second end of the primary optical system into two light beams, with the two light beams not being parallel to each other; and a pair of secondary optical systems which receive one of the light beams and forming an image of the object. Therefore, the size of the stereoscopic endoscope can be reduced since extra space is not required to have parallel secondary optical systems.

In a preferred embodiment, the primary optical system is housed within an insertion portion of the stereoscopic endoscope, and the secondary optical systems are housed within an observing portion of the endoscope. The insertion portion is attached to the observing portion using a cylindrical adapter. This allows the insertion portion of monocular endoscopes to be used with the observing portion of the stereoscopic endoscope.

In another preferred embodiment, each of the secondary optical systems includes an imaging lens for forming an image of the object in accordance with the refracted light beam, and an imaging device for detecting the images formed by the imaging lens, with the imaging devices outputting image signals.

Alternatively, the stereoscopic endoscope is provided with a single imaging device. The images formed by the imaging lenses of the secondary optical systems is formed on different areas of the single imaging device.

Optionally, each of the secondary optical systems is provided with a liquid crystal shutter, which allows or prohibits the formation of the image by the secondary optical system. Therefore, when the image is being formed by one of the secondary optical systems on the single imaging device, the liquid crystal shutter of the other secondary optical system prohibits the formation of the other image by the other secondary optical system.

In this case, the first area and second area of the single imaging device can overlap, and therefore, the size of the single imaging device can be reduced, thereby reducing the cost of manufacturing the stereoscopic endoscope.

In yet another preferred embodiment, each of the secondary optical systems includes a prism for refracting the received light beams, such that the refracted light beams are parallel to an optical axis of the primary optical system, an imaging lens for forming an image of the object in accordance with the refracted light beam, and an eyepiece lens for viewing the image formed by the imaging lens. This permits direct viewing of the three-dimensional image.

Alternatively, a single deflecting prism is provided for refracting the received light beams. This reduces the number of parts required to manufacture the stereoscopic endoscope.

Further, a single roof prism may replace the prism used for dividing the light. This results in a less complex prism being used in the manufacturing of the stereoscopic endoscope.

According to a fifth aspect of the present invention, there is provided a method of adjusting a position of a light dividing mechanism of a stereoscopic endoscope to a predetermined position. Light from an object having a uniform brightness is transmitted by a primary optical system of the stereoscopic endoscope to the light dividing mechanism, which divides the light into two light beams, with each light beam being incident on an imaging device. The method includes the steps of:

- detecting a brightness pattern of an image formed on each of the imaging devices;
- determining a direction and amount of movement required to position the light dividing mechanism at the predetermined position, in response to the detected brightness pattern of each of the images; and
- adjusting the position of the light dividing mechanism in accordance with the direction and movement amount determined in the determining step.

In a preferred embodiment, the determining step includes the steps of calculating a direction of movement of the light dividing mechanism, and comparing a position of the light dividing mechanism with the predetermined position. Further, the adjusting step includes the step of driving the light dividing mechanism by a fixed amount. Furthermore, the detecting step, the determining step and the adjusting step are repeated until the determining step determines that the position of the light dividing mechanism is at the predetermined position. Since the calculating step only determines a direction of movement, the number of bits required for the calculation is low.

Alternatively, the calculating step also calculates the amount of movement required to move the light dividing mechanism to the predetermined position. In this case, the driving step drives the light dividing mechanism directly to the predetermined position, after the first calculation. Therefore, the light dividing mechanism can be quickly and accurately placed at the predetermined position.

According to a sixth aspect of the present invention, there is provided an adapter for enabling a monocular endoscope to be used with a stereoscopic observing portion. The observing portion includes a device for dividing light transmitted by the monocular endoscope, into two light beams, by a pair of optical systems. Each of the optical systems receives one of the light beams and forms an image of the object. The adapter includes a device for connecting the observing portion of the stereoscopic endoscope to the monocular endoscope.

Thus, the range of insertion portions that can be used with the observing portion of the stereoscopic endoscope is increased.

In a preferred embodiment, the connecting device includes a plurality of screws and nuts for attaching the adapter to the observing portion. Therefore, the adapter can be easily attached to the observing portion of the stereoscopic endoscope.

In another preferred embodiment, the connecting device includes a device for adjusting a positional relationship of the observing portion and the monocular endoscope. This allows for accurate positioning of the monocular endoscope in relation to the light dividing device of the observing portion. Therefore, the three-dimensional effect of the image can be changed by using the adjusting device.

In the preferred embodiment, the adjusting device includes a first set of screws oriented along a first direction, and a second set of screws oriented along a second direction. The second direction may be perpendicular to the first direction. Further, the first set of screws adjusts a position of the adapter relative to the observing portion along the first direction. The second set of screws adjusts a position of the adapter relative to the observing portion along the second direction. Therefore, accurate two dimensional adjustment of the position of the monocular endoscope relative to the observing portion can be achieved.

Optionally, each screw is rotated by a motor. This allows automatic adjustment of the position of the monocular endoscope relative to the observing portion.

According to a seventh aspect of the present invention, there is provided a stereoscopic endoscope which has a primary optical system for transmitting light, reflected by an object located near a first end of the primary optical system, along a first optical path to an exit pupil located at a second end of the primary optical system. The stereoscopic endoscope is also provided with a device for dividing the light transmitted to the second end of the primary optical system into two light beams, and a pair of secondary optical systems. Each of the secondary optical systems receives one of the light beams and forms an image of the object. The stereoscopic endoscope further provides a device for emitting light through a second optical path of the primary optical system which is parallel to the first optical path. The emitted light is incident on the object and does not interfere with the first optical path. Therefore, the stereoscopic endoscope provides the light required for viewing the object, and an auxiliary light source is not need.

According to an eighth aspect of the present invention, there is provided a stereoscopic endoscope having a primary optical system for transmitting light, reflected by an object located near a first end of the primary optical system, to a second end of the primary optical system. The stereoscopic endoscope also includes a device for dividing the light transmitted through the primary optical system into two light beams, and a pair of secondary optical systems. Each of the secondary optical systems receives one of the light beams and forms an image of the object. Further, each of the secondary optical systems includes an eyepiece lens for viewing the image and an imaging device for detecting the images formed by the secondary optical system. A half mirror is provided in each secondary optical system for reflecting half of the received light to one of the eyepiece lens and the imaging device, and for transmitting the other half of the received light to other of the eyepiece lens and the imaging device.

Therefore, the three-dimensional image can be viewed directly using the eyepiece lenses or indirectly using the imaging devices. This increases the facility of the viewing of the three-dimensional image observed using the stereoscopic endoscope.

In a preferred embodiment, the light dividing device includes two mirrors arranged perpendicular to each other, with each of the mirrors arranged at a 45° angle to an optical axis of the primary optical system. Further, stereoscopic endoscope also includes a device for adjusting a distance between each of the two mirrors. Therefore, by adjusting the distance between the two mirrors, the three-dimensional effect of the image can be changed.

In another preferred embodiment, the dividing device includes a half mirror for dividing the light into the two light beams. This reduces the number of parts required to manufacture the endoscope.

According to a ninth aspect of the present invention, there is provided a stereoscopic endoscope having a primary optical system for transmitting a luminous flux, reflected by an object located near a first end of the optical system, to a second end of the optical system. The stereoscopic endoscope also includes a device for forming a first image of the object in accordance with a first area of the luminous flux, and another device for forming a second image of the object in accordance with a second area of the luminous flux. The second area of the luminous flux does not overlap the first area of the luminous flux. A single imaging device detects the first image and the second image and outputs an image signal. By using only one imaging device, the cost of manufacturing the stereoscopic endoscope can be decreased.

In a preferred embodiment, the first image is formed on a first portion of the imaging device, and the second image is formed on a second portion of the imaging device, which is separate from the first portion. Therefore, by processing the image signal, the left and right images can be obtained.

In another preferred embodiment, each image forming device is provided with a liquid crystal shutter, which controls a timing of the image formation by alternately prohibiting and allowing transmission of light through the image forming device. Further, the first and second images are alternately formed on overlapping portions of the imaging device. Therefore, the size of the imaging device can be reduced, and the cost of manufacturing the stereoscopic endoscope can also be reduced.

BRIEF DESCRIPTION OF THE FIGURES

FIGS. 3A and 3B are perspective views for defining directions of movement of the mirror block shown in FIG. 2A;

FIG. 4 is a top view of the mirror block showing optical paths when the mirror block is positioned at a standard correct position;

FIGS. 11A and 11B show brightnesses of left and right images taken by the stereoscopic endoscope shown in FIG. 1, when the mirror block is moved in along the x-axis in the +x and −x directions, respectively;

FIGS. 11C and 11D show brightnesses of left and right images taken by the stereoscopic endoscope shown in FIG. 1, when the mirror block is moved in along the y-axis in the +y and −y directions, respectively;

FIGS. 11E and 11F show brightnesses of left and right images taken by the stereoscopic endoscope shown in FIG. 1, when the mirror block is rotated about the x-axis in the clockwise and counterclockwise directions, respectively;

FIG. 35 is a sectional view of a stereoscopic endoscope according to a nineteenth embodiment of the present invention;

FIG. 39A is a top view of the separator lenses of the pupil dividing mechanism according to a modification of the twenty-first embodiment, showing light paths when the separator lenses are positioned closest to each other;

FIG. 39B is a top view of the separator lenses of the pupil dividing mechanism according to a modification of the twenty-first embodiment;

FIG. 42A is a top view of separator lenses of a pupil dividing mechanism according to a twenty-third embodiment of the present invention, showing light paths when the separator lenses are positioned closest to each other;

FIG. 42B is a front view of the separator lenses of the pupil dividing mechanism, viewed from the object side, showing a relationship between illumination light beams and an observing field of an exit pupil of the primary optical system of the stereoscopic endoscope;

FIGS. 58A through 58D are front views showing modified arrangements of separator lenses in an exit pupil of a primary optical system of the stereoscopic endosocope shown in FIG. 56A;

FIGS. 59A through 59D are front views showing additional modified arrangements of the separator lenses shown in FIGS. 58A through 58D;

DESCRIPTION OF THE EMBODIMENTS

The present invention will now be described with reference to FIGS. 1A through 70.

Figure 1A:
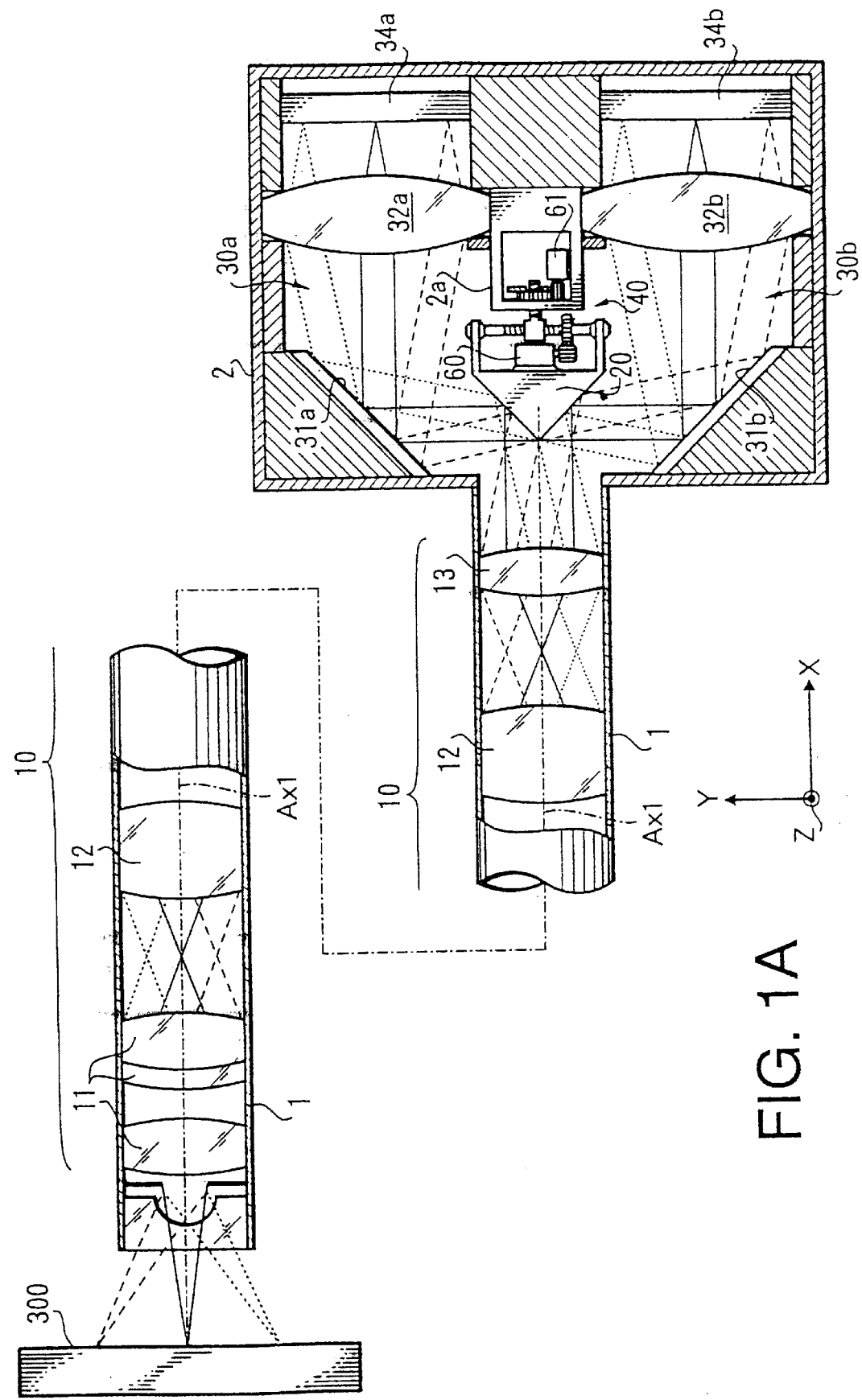
FIG. 1A shows a sectional view of a stereoscopic endoscope according to a first embodiment of the present invention.

FIG. 1A shows a sectional view of a stereoscopic endoscope according to the present invention. The stereoscopic endoscope comprises an insertion portion 1 and an observing portion 2. The insertion portion 1, is inserted through a narrow opening into an object or cavity (such as the digestive tract or abdominal cavity of the human body) that is to be observed. The observing portion 2 is optically connected to the insertion portion 1 and allows an observer to see an image of the object being observed.

The insertion portion 1 includes a primary optical system 10. The primary optical system 10, as shown in FIG. 1A, consists of an objective lens 11, a first relay lens 12, and a second relay lens 13. In this specification the term "lens" can mean a "single lens" or a "group of lenses". The objective lens 11 forms an image of the object being observed. The first relay lens 12 and second relay lens 13 transmit the image to an exit pupil of the optical system 10, in order to be observed by the observing portion 2.

Figure 1B:
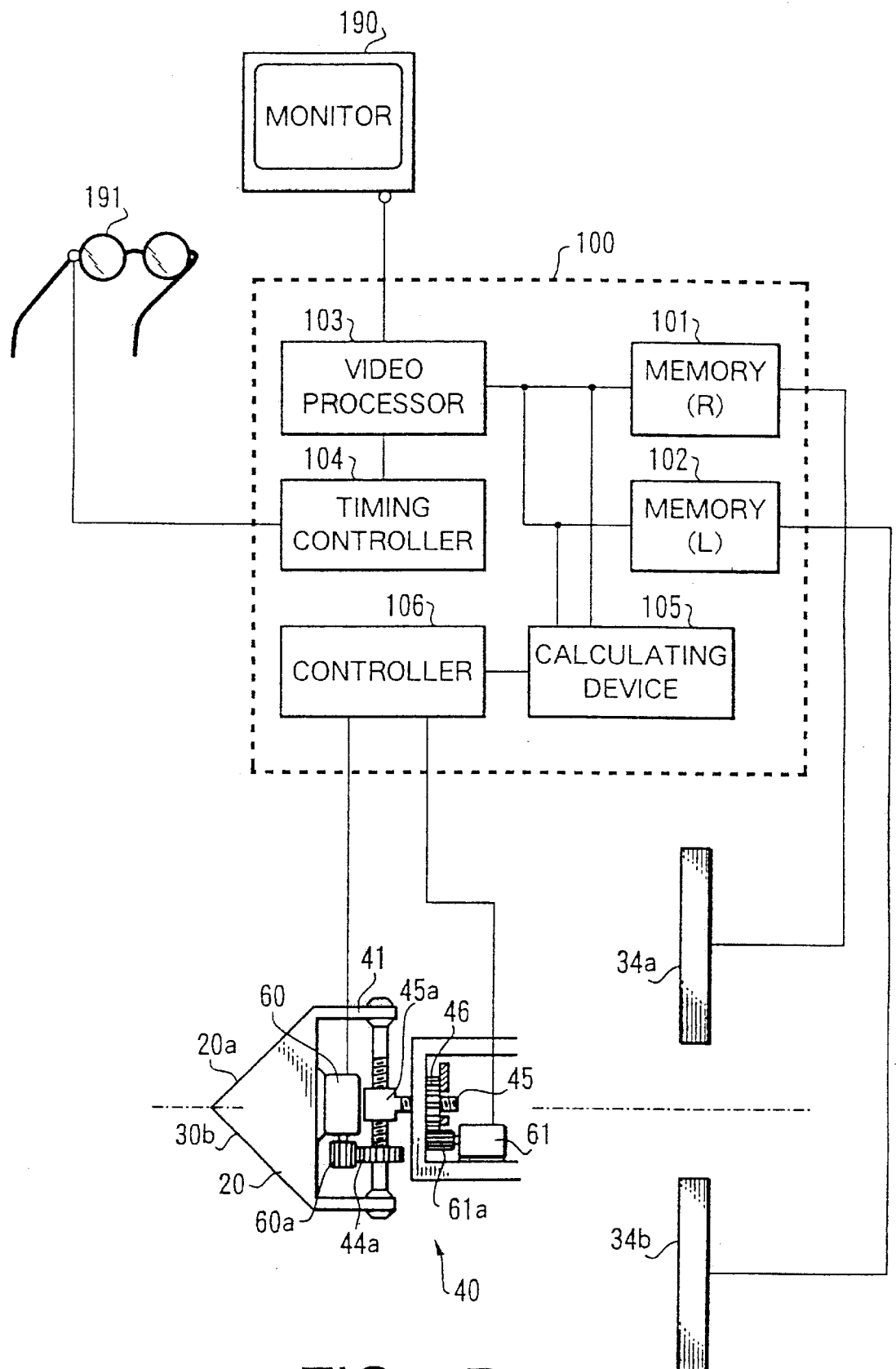
FIG. 1B shows a block diagram of a processing device used with the stereoscopic endoscope shown in FIG. 1A, according to the first embodiment of the present invention.

The observing portion 2 includes a pupil dividing mirror block 20, and a pair of secondary optical systems 30A and 30B (see e.g., FIGS. 1A and 1B). The mirror block 20 consists of a pair of mirrored surfaces 20a and 20b. The optical systems 30A, 30B consist of mirrors 31a, 31b, imaging lenses 32a, 32b and imaging devices 34a, 34b, respectively. In the preferred embodiment, the imaging devices 34a, and 34b are CCDs.

Light from the primary optical system 10 that is incident on the mirrored surface 20a is reflected to the mirror 31a and then reflected to the imaging lens 32a. The imaging lens 32a forms an image on the imaging device 34a. Similarly, light from the primary optical system 10 that is incident on the mirrored surface 20b is reflected to the mirror 31b and then reflected to the imaging lens 32b. The imaging lens 32b forms an image on the imaging device 34b.

As shown in FIG. 1A, and described above, the light transmitted from the primary optical system 10, is divided into two separate paths and an image of the divided light is produced by the secondary optical systems 30a and 30b. The secondary optical system 30a forms an image that is seen by a right eye of the observer, while the secondary optical system 30b forms an image that is seen by a left eye of the observer. Therefore, each of the optical systems 30a, 30b will produce an image of the object from a slightly different perspective, resulting in a three-dimensional view of the object being observed.

However, in order to achieve the proper three-dimensional perspective of the object, an area of the exit pupil Ep through which light is transferred to the secondary optical system 30a, must be the same size as an area of the exit pupil Ep through which light is transferred to the secondary optical system 30b.

Figure 2A:
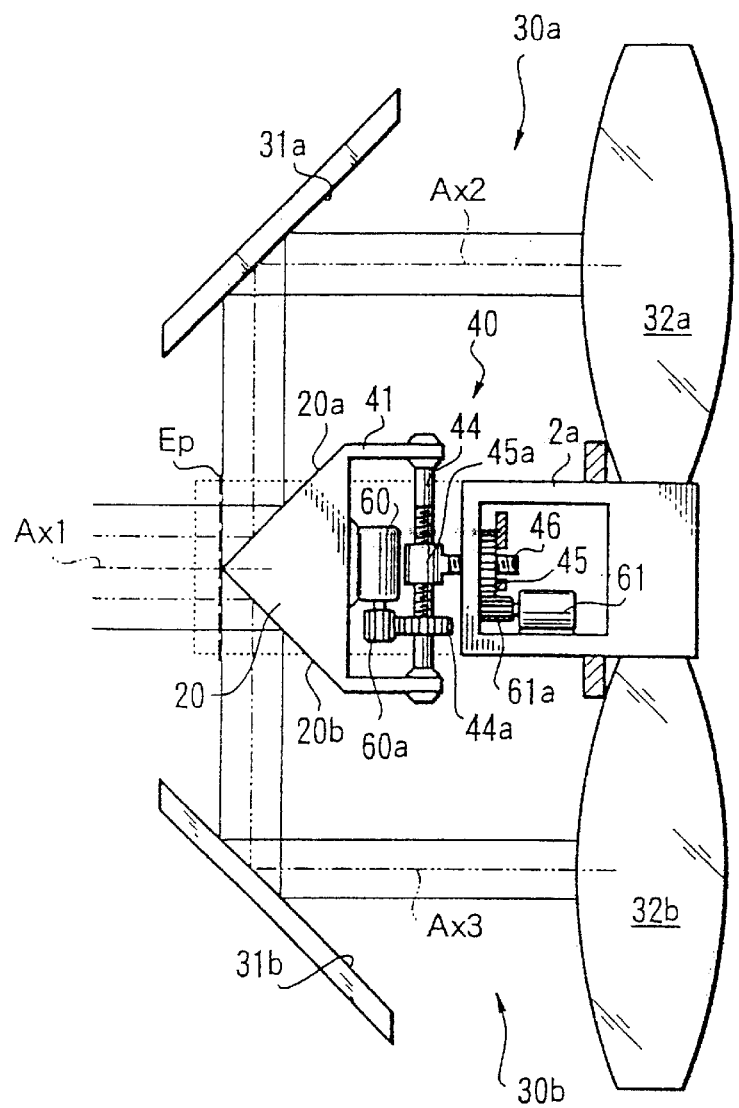
FIGS. 2A and 2B are enlarged views of a mirror block of the stereoscopic endoscope shown in FIG. 1.
Figure 2B:
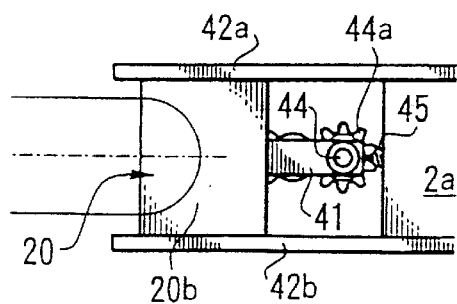

FIG. 2A shows an enlargement of the mirror block 20, the secondary optical systems 30a, 30b, and the exit pupil of the primary optical system 10. In order to achieve the proper three-dimensional perspective, the ridge line between the mirrored surfaces 20a and 20b, must be coincident with the plane of the exit pupil and an optical axis Ax1 of the primary optical system 10. If this condition is satisfied, then the mirror block 20 is in the standard correct position. Further, the mirrored surfaces 20a, 20b are arranged to be at an angle of 45° to the optical axis Ax1, when the mirror block 20 is at the standard correct position.

Further, as shown in FIG. 2A, when the mirror block 20 is at the standard correct position, a center axis Ax2 of the light reflected by the mirrored surface 20a is coincident with an optical axis of the secondary optical system 30a, and a center axis Ax3 of the light reflected by the mirrored surface 20b is coincident with an optical axis of the secondary optical system 30b. Further, the axes Ax2 and Ax3 are positioned at a predetermined distance on either side of the axis Ax1, and therefore, parallax corresponding to the distance occurs in the images formed at the imaging devices 34A and 34B.

FIGS. 3 through 10 will be used to explain the effect on the image detected by the imaging devices 34a and 34b, by moving the mirror block 20 from the standard correct position. As shown in FIGS. 3A through 10B, the uniformity of brightness of the two images will be affected by the movement of the mirror block 20. Further, the exit pupil Ep is shown as a bold line in FIGS. 4 through 10A.

The mirror block 20 has six degrees of freedom, as shown in FIGS. 3A and 3B. The mirror block 20 can be moved along the x-axis, y-axis or z-axis. Further, the mirror block 20 may be rotated about any of these axes. However, movement along the z-axis may be ignored, since the mirror block 20 has enough height in the z-axis direction. Hereinafter, only five degrees of freedom will be described.

In the following description, $\phi 1$ denotes the movement along the x-axis, $\phi 2$ the movement along the y-axis, $\phi 3$ the rotation about the x-axis, $\phi 4$ the rotation about the y-axis and $\phi 5$ the rotation about the z-axis.

FIG. 3A shows the reference x, y and z axes. Movement along one of the axes in a direction toward the arrow is defined as positive(+) movement, while the movement in the reverse direction is defined as negative (−) movement. FIG. 3B shows one of the three axes and a rotation movement about the axis. Clockwise rotation about the axis is defined as positive (+) rotation, while counterclockwise rotation is defined as negative (−) rotation.

FIG. 4 shows the light paths incident from the second relay lens 13 and divided by the mirror block 20 that is located at the standard correct position (i.e., all displacements in any direction are equal to zero). At this position, the center light beam (shown by solid line L0) transmitted along the optical axis Ax1, the left light beam (shown by line LL) transmitted from the left side of the primary optical system 10, and the right light beam (shown by line LR) transmitted from the right side of the primary optical system 10, are each divided into two uniformly equal light beams by the mirror block 20.

Figure 5A:
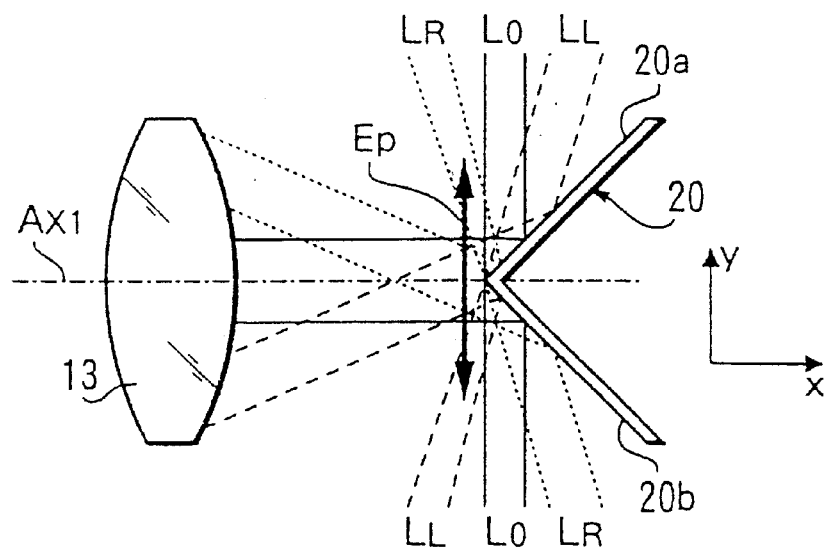
FIG. 5A is a top view of the mirror block showing optical paths when the mirror block is linearly displaced in a +x direction from the standard correct position.

FIG. 5A shows the mirror block 20 displaced from the standard correct position by +$\phi 1$, (i.e., in the positive x-axis direction). In this case, the fraction of the left light beam LL that is incident on the right mirror surface 20a is increased, and the fraction of the right light beam LR that is incident on the left mirror surface 20b is also increased. The center light beam L0 remains divided into two equal light beams.

Figure 5B:
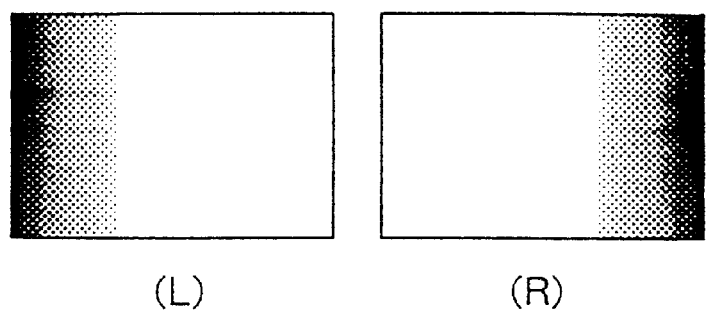
FIG. 5B shows a brightness distribution of left and right images taken by the stereoscopic endoscope shown in FIG. 1, when the mirror block is in the position shown in FIG. 5A.

FIG. 5B shows the effect on the right and left images detected by the CCDs 34A and 34B, respectively, when the mirror block 20 is moved from the standard correct position by +$\phi 1$. As shown in FIG. 5B, the left side of the left image, and the right side of the right image become dark. The remaining portions of the two images become bright.

Figure 6A:
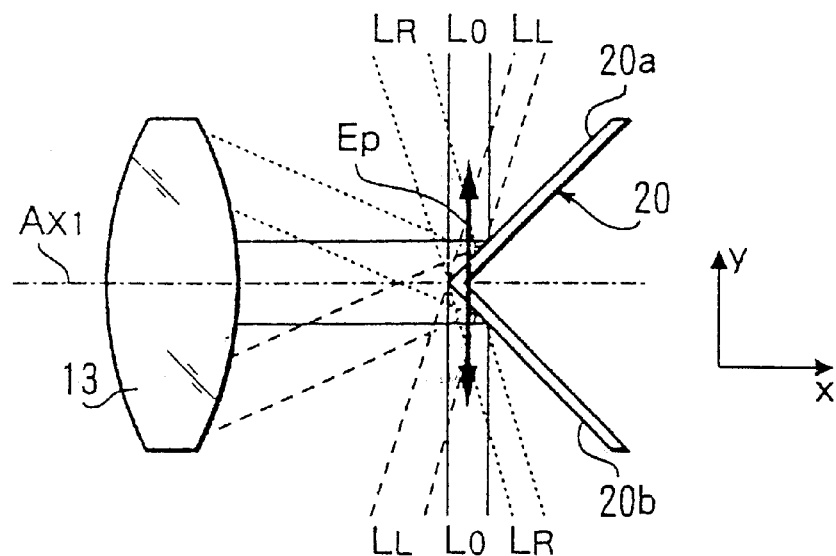
FIG. 6A is a top view of the mirror block showing optical paths when the mirror block is linearly displaced in a −x direction from the standard correct position.

FIG. 6A shows the pupil dividing mirror block 20 displaced from the standard correct position by −$\phi 1$ (i.e., in the negative x-axis direction). In this case, the fraction of the left light beam LL that is incident on the left mirror surface 20b is increased, and the fraction of the right light beam LR that is incident on the right mirror surface 20a is also increased. The center light beam L0 remains equally divided.

Figure 6B:
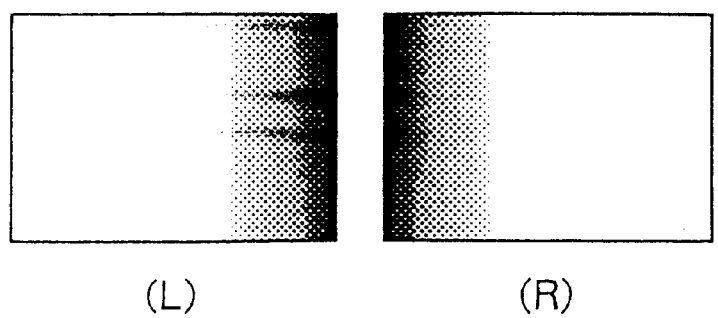
FIG. 6B shows a brightness distribution of left and right images taken by the stereoscopic endoscope shown in FIG. 1, when the mirror block is in the position shown in FIG. 6A.

FIG. 6B shows the effect on the right and left images detected by the CCDs 34A and 34B, respectively, when the mirror block 20 is moved from the standard correct position by −$\phi 1$. As shown in FIG. 6B, the right side of the left image, and the left side of the right image become dark. The remaining portions of the two images become bright.

Figure 7A:
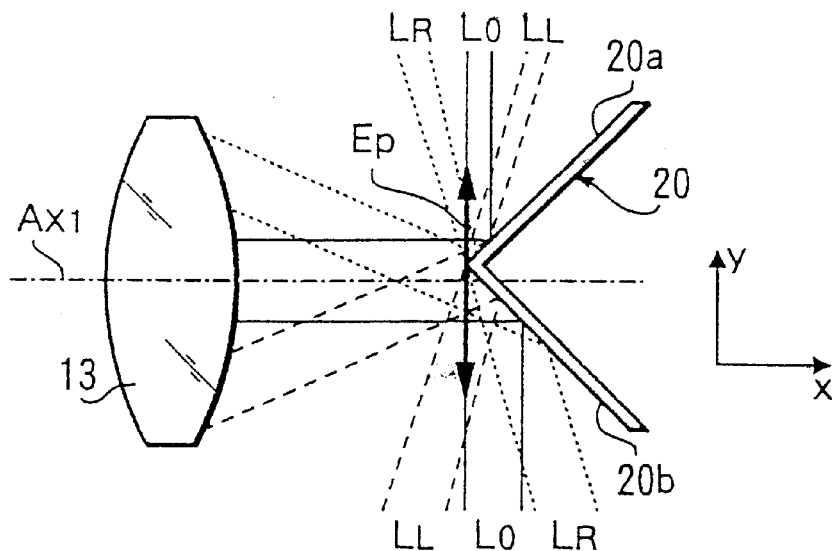
FIG. 7A is a top view of the mirror block showing optical paths when the mirror block is linearly displaced in a +y direction from the standard correct position.

FIG. 7A shows the mirror block 20 displaced from the standard correct position by +$\phi 2$ (i.e., in the positive y-axis direction). In this case, the fraction of the left light beam LL, the right light beam LR and the center light beam LO that is incident on the left mirror surface 20b is increased.

Figure 7B:
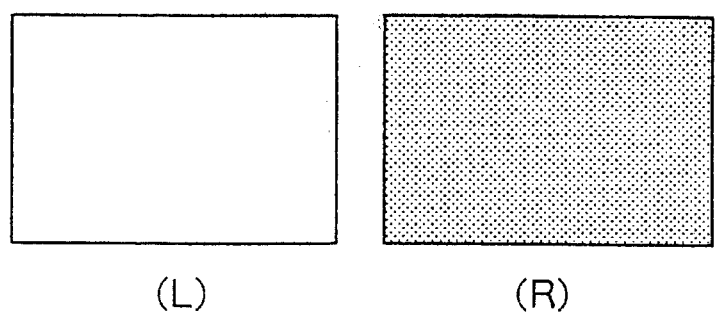
FIG. 7B shows a brightness distribution of left and right images taken by the stereoscopic endoscope shown in FIG. 1, when the mirror block is in the position shown in FIG. 7A.

FIG. 7B shows the effect on the right and left images detected by the CCDs 34A and 34B, respectively, when the mirror block 20 is moved from the standard correct position by +$\phi 2$. As shown in FIG. 7B, the left image becomes bright, while the right image becomes dark.

Figure 8A:
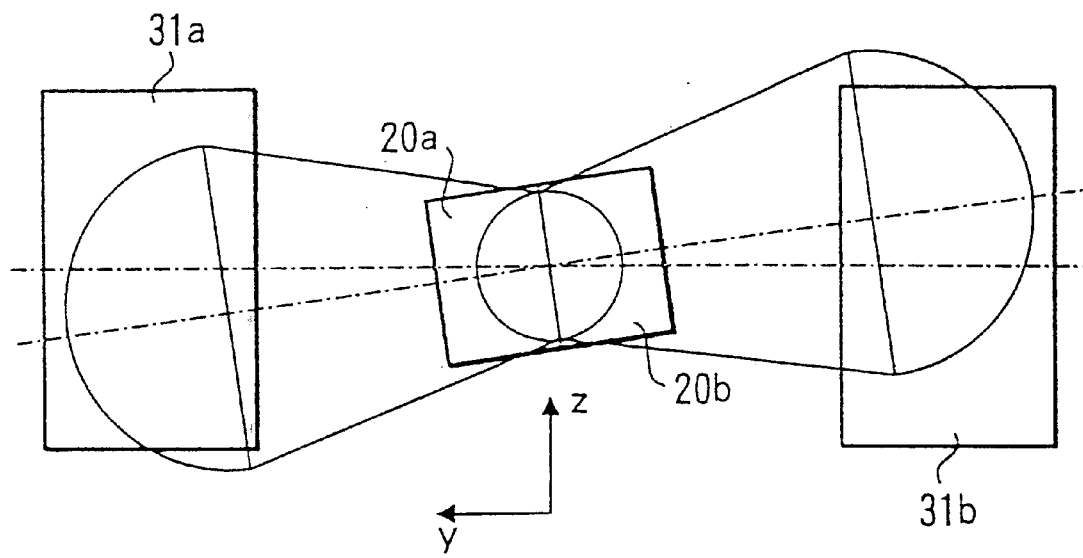
FIG. 8A is a front view of the mirror block from the object side showing optical paths when the mirror block is rotated about the x-axis from the standard correct position.

FIG. 8A shows the mirror block 20 displaced from the standard correct position by +$\phi 3$ (i.e., rotated about the x-axis in the clockwise direction). In this case, the left light beam LL, the right light beam LR and the center light beam LO are reflected such that they are not incident on the upper part of the mirrored surface 31a or the lower part of the mirrored surface 31b.

Figure 8B:
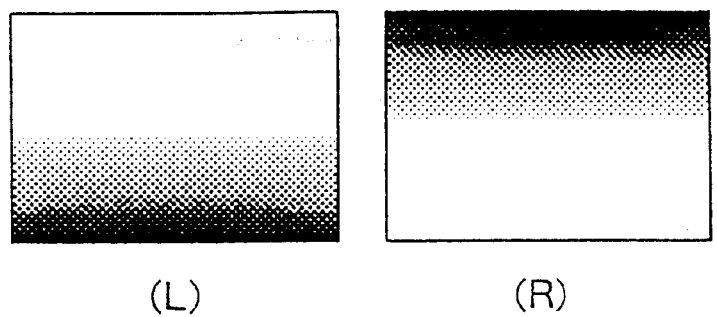
FIG. 8B shows a brightness distribution of left and right images taken by the stereoscopic endoscope shown in FIG. 1, when the mirror block is in the position shown in FIG. 8A.

FIG. 8B shows the effect on the right and left images detected by the CCDs 34A and 34B, respectively, when the mirror block 20 is moved from the standard correct position by +$\phi 3$. As shown in FIG. 8B, the lower portion of the left image and the upper portion of the right image becomes dark, while the remaining portions of the two images become bright.

Figure 9A:
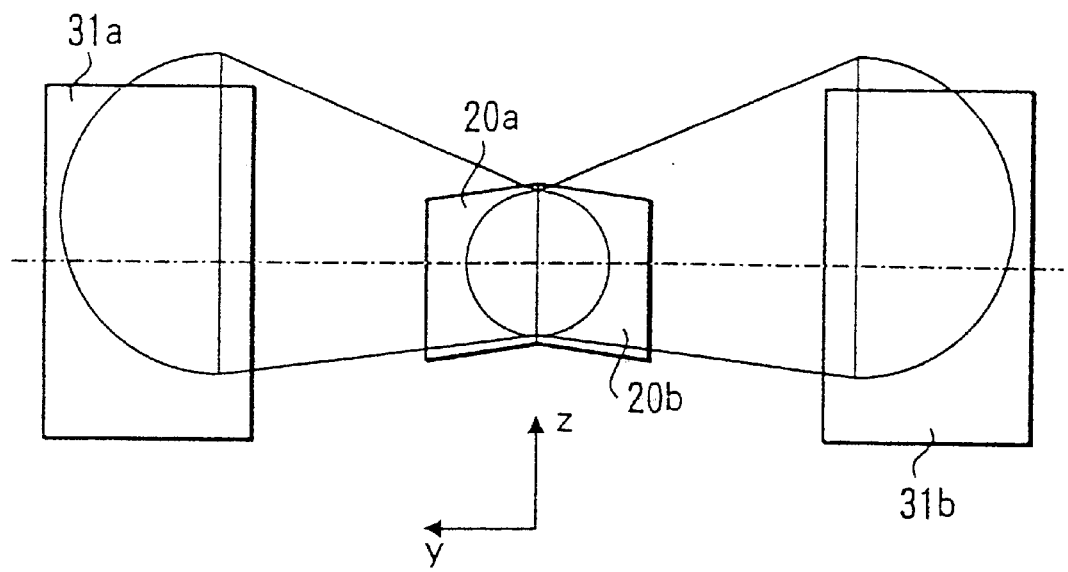
FIG. 9A is a front view of the mirror block from the object side showing optical paths when the mirror block is rotated about the y-axis from the standard correct position.

FIG. 9A shows the mirror block 20 displaced from the standard correct position by +$\phi 4$ (i.e., rotated about the y-axis in the clockwise direction). In this case, the left light beam LL, the right light beam LR and the center light beam L0 are reflected such that they are not incident on the lower part of the mirrored surface 31a or the lower part of the mirrored surface 31b.

Figure 9B:
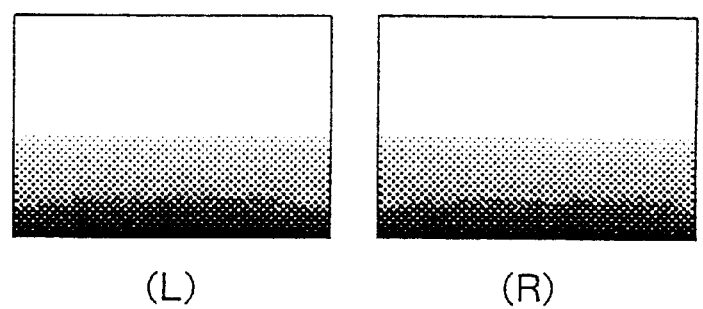
FIG. 9B shows a brightness distribution of left and right images taken by the stereoscopic endoscope shown in FIG. 1, when the mirror block is in the position shown in FIG. 9A.

FIG. 9B shows the effect on the right and left images detected by the CCDs 34A and 34B, respectively, when the mirror block 20 is moved from the standard correct position by +$\phi 4$. As shown in FIG. 9B, the lower portion of the left image and the lower portion of the right image becomes dark, while the remaining portions of the two images become bright.

Figure 10A:
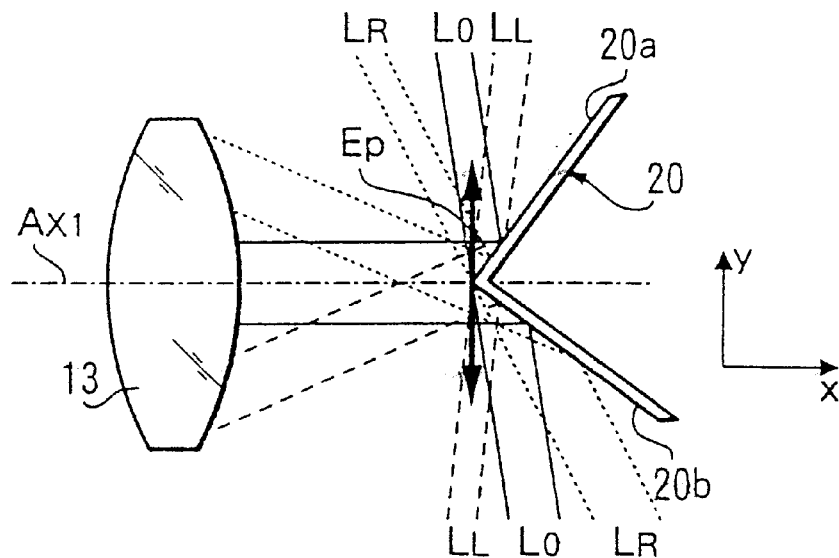
FIG. 10A is a top view of the mirror block showing optical paths when the mirror block is rotated about the z-axis from the standard correct position.

FIG. 10A shows the mirror block 20 displaced from the standard correct position by +$\phi 5$ (i.e., rotated about the z-axis in the clockwise direction). In this case, the left light beam LL, the right light beam LR and the center light beam LO are reflected such that they are not incident on the left part of the mirrored surface 31a or the left part of the mirrored surface 31b.

Figure 10B:
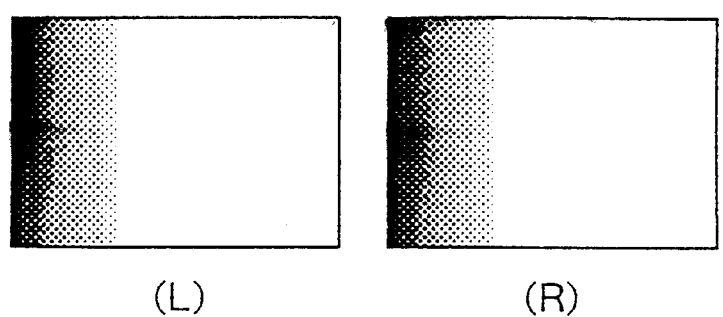
FIG. 10B shows a brightness distribution of left and right images taken by the stereoscopic endoscope shown in FIG. 1, when the mirror block is in the position shown in FIG. 10A.
Figure 11H:
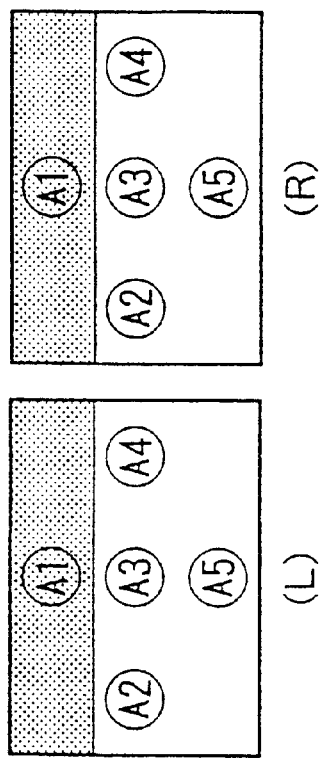
FIGS. 11G and 11H show brightnesses of left and right images taken by the stereoscopic endoscope shown in FIG. 1, when the mirror block is rotated about the y-axis in the clockwise and counterclockwise directions, respectively.
Figure 11J:
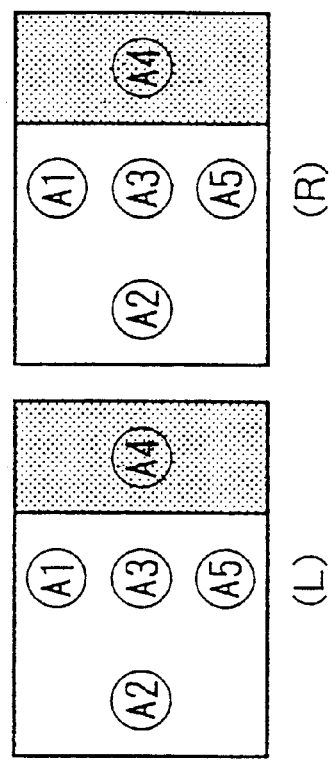
FIGS. 11I and 11J show brightnesses of left and right images taken by the stereoscopic endoscope shown in FIG. 1, when the mirror block is rotated about the z-axis in the clockwise and counterclockwise directions, respectively.
Figure 11G:
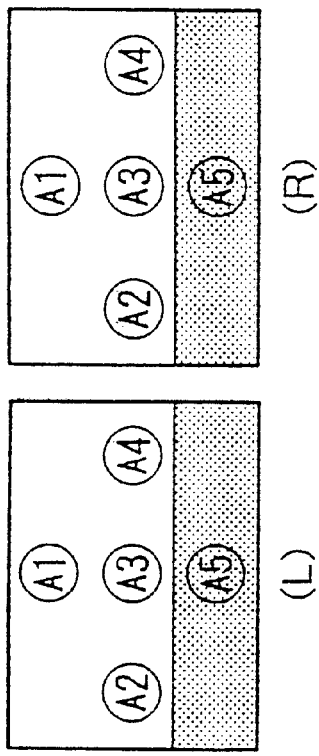
Figure 11I:
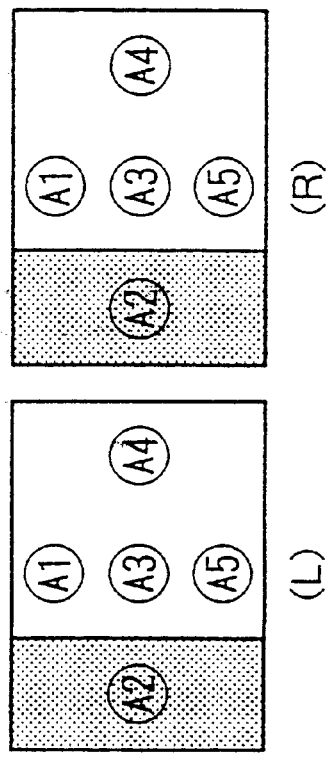

FIG. 10B shows the effect on the right and left images detected by the CCDs 34A and 34B, respectively, when the mirror block 20 is moved from the standard correct position by +$\phi 5$. As shown in FIG. 10B, the left side of the left image and the left side of the right image becomes dark, while the remaining portions of the two images become bright.

Thus, as described above, the position of the mirror block 20 relative to the exit pupil Ep, and the optical axes Ax1, Ax2, and Ax3, is critical if the brightness of the left and right images is to be uniform, and the three-dimensional perspective is to be maintained.

Therefore, by detecting a difference between the brightness of different portions of each of the left and right images, and a difference in brightness between the left image and the right image, the direction for moving the mirror block 20, in order to achieve a uniform brightness of both images, can be determined.

FIRST EMBODIMENT

A first embodiment of the present invention, will be described with reference to FIGS. 1A, 1B, 2A and 2B.

The position of the mirror block 20 is adjustable in the x and y directions between a pair of parallel guide plates 42a and 42b (see FIG. 2B), by an adjusting mechanism 40. The adjusting mechanism 40 includes a holding frame 41, which is attached to a base portion of the mirror block 20, and a first screw 44, which is fitted into the holding frame 41. A first motor 60 is attached to the base of the mirror block 20, and has a pinion 60A. A first gear 44A is meshed with the pinion 60A, and is also meshed with the first screw 44. When the first motor 60 is driven, the pinion 60A rotates the first gear 44A and thereby moves the screw 44 in the y direction.

A second screw 45 is fitted through a holding wall 2a of the observing portion 2. A nut portion 45a formed on the head of the second screw 45 is engaged with the first screw 44. A second motor 61 is attached to the inside of the holding wall 2a, and has a pinion 61a. A second gear 46 which is meshed with the pinion 61a and the second screw 45, is installed inside the holding wall 2a. When the second motor 61 is driven, the pinion 61A rotates the second gear 46 and thereby moves the screw 45 in the x direction.

Thus, as described above, the mirror block 20 is supported by the first screw 44 that is held by the second screw 45 which is fitted through the holding wall 2a. Further, by driving the motors 60 and 61, the position of the mirror block 20 can be adjusted in the x and y directions, until the ridge line between the mirrored surfaces 20a and 20b, is coincident with the exit pupil and the optical axis Ax1, of the primary optical system 10. Furthermore, the effect on the left and right images formed at the imaging devices 34a and 34b described above, can be used to determine which direction the mirror block 20 should be moved in order to restore uniform brightness to the detected images.

As shown in FIG. 1A, a light source 300 outputs a diffuse light having a uniform brightness. The light is incident on the primary optical system 10, and transmitted to the observing unit 2.

As shown in FIG. 1B, an image signal is output from each of the imaging devices 34a and 34b and is sent to a processor 100. More specifically, picture data contained within the image signal is stored in memories 101 and 102, respectively. The picture data of one image is compared with the picture data of the other image by a calculating device 105. The calculating device 105 outputs a driving signal to a controller 106. The controller 106 controls the first motor 60 and second motor 61 to drive the mirror block 20 to a position (i.e., the standard correct position) which will result in a uniform brightness of the left and right images.

Once the mirror block 20 has been adjusted to standard correct position, the picture data for the left and right images are further processed by a video processor 103 and output to a monitor 190. A timing controller 104 controls the video processor to alternately output the left and right image to the monitor 190. An observer wears a pair of glasses 191 that has shutters such as liquid crystal shutters in a viewfields of each eye. The shutters are controlled by the timing controller 104 to be alternately open and shut, such that the image on the monitor 190 can be viewed by only one eye at one time. The timing controller 104 outputs control signals corresponding to the output timing of the picture data of the video processor 103. Therefore, the shutter in front of the right eye of the glasses 191 blocks the light when the left picture is displayed on the monitor 190. Conversely, the shutter of left eye blocks the light when the right picture is displayed.

The pair of glasses 191 allow an observer to view the left picture taken by the left image sensing element 34a using only the left eye, and the right picture taken by the right image sensing element 34b by using only the right eye. Therefore, the observer is able to view a three-dimensional image of the object.

Thus, as described above, the difference in brightness between the left and right images, and the difference in brightness between each image is detected. Then, the position of the mirror block 20 is automatically adjusted to the standard correct position.

The calculating device 105 and the controller 106 are only used during the adjustment and are not used during the observation.

The operation of the calculating device 105, and the detection of the image brightness will be described with reference to FIGS. 11A through 11J and 12A through 12D.

FIGS. 11A through 11J show the brightness of the left and right images when the mirror block 20 has been moved in one of the directions or rotations φ1 through φ5.

As shown in FIGS. 11A through 11J, there are five brightness detection zones, A1, A2, A3, A4 and AS, respectively. The intensities I1, I2, I3, I4 and I5 are measured for the detection zones, A1, A2, A3, A4 and A5, respectively. Each intensity may be the output of one picture cell or an average of a group of cells.

Table 1 below summarizes the displacement of the mirror block 20 from the standard correct position corresponding to each of the FIGS. 11A through 11J, as well combinations of two types of displacements. In Table 1, "d" denotes "dark", "b" denotes "bright", "vd" denotes "very dark" and "vb" denotes "very bright". These terms are relative to a standard brightness, which is defined as the brightness of the each of the left and right images when the mirror block 20 is located at the standard correct position. In Table 1, the intensities which have no data have the standard brightness level.

TABLE 1

| | Displacement | | | | | Measurement Value | | | | | | | | | |
| | | | | | | Left Picture | | | | | Right Picture | | | | |
| | φ1 | φ2 | φ3 | φ4 | φ5 | I1 | I2 | I3 | I4 | I5 | I1 | I2 | I3 | I4 | I5 |
| A | + | | | | | | d | b | | | b | | d | | |
| B | − | | | | | | b | d | | | d | | b | | |
| C | | + | | | | | | | | | d | d | d | d | d |
| D | | − | | | | d | d | d | d | d | | | | | |
| E | | | + | | | d | | | b | | b | | | | d |
| F | | | − | | | b | | | d | | d | | | | b |
| G | | | | + | | b | | | d | | b | | | | d |
| H | | | | − | | d | | | b | | d | | | | b |
| I | | | | | + | | d | | b | | | d | | b | |

TABLE 1-continued

| | Displacement | | | | | Measurement Value | | | | | | | | | |
| | | | | | | Left Picture | | | | | Right Picture | | | | |
| | φ1 | φ2 | φ3 | φ4 | φ5 | I1 | I2 | I3 | I4 | I5 | I1 | I2 | I3 | I4 | I5 |
|---|---|---|---|---|---|---|---|---|---|---|---|---|---|---|---|
| J | | | | | − | | b | | d | | | b | | d | |
| K | + | | | | + | | vd | | vb | | | | | | |
| L | + | | | | − | | | | | | | vb | | vd | |
| M | − | | | | + | | | | | | | vd | | vb | |
| N | − | | | | − | | vb | | vd | | | | | | |
| O | | | + | + | | | | | | | vb | | | | vd |
| P | | | + | − | | vd | | | | | | | vb | | |
| Q | | | − | + | | vb | | | | | | | vd | | |
| R | | | − | − | | | | | | | | vd | | | vb |

The first six rows in Table 1 (i.e., A through F) show the intensities I1 through I5 for each of the detecting zones A1 trough A5 as a result of the displacement of the mirror block 20, along one of the axes. The resulting left and right image patterns detected by the imaging devices 34a and 34b, respectively, are shown in FIGS. 11A through 11F, respectively. Therefore, by comparing the intensities I1 through I5 of the image sensor areas A1 through A5 of the left image, with the intensities I1 through I5 of the image sensor areas A1 through A5 of the right image, it is possible to detect the position of the mirror block 20 relative to the standard correct position. Further, the direction in which the mirror block 20 should be moved in order to return to the standard correct position can be determined.

The next four rows in Table 1 (i.e., G through J) show the intensities I1 through I5 for each of the detecting zones A1 trough A5 as a result of the rotation of the mirror block 20, about one of the axes. The resulting left and right image patterns detected by the imaging devices 34a and 34b, respectively are shown in FIGS. 11G through 11J, respectively. Therefore, by comparing the intensities I1 through I5 of the image sensor areas A1 through A5 of the left image with the intensities I1 through I5 of the image sensor areas A1 through A5 of the right image, it is possible to detect the position of the mirror block 20 relative to the standard correct position. Further, the direction in which the mirror block 20 should be rotated in order to return to the standard correct position can be determined.

As shown in Table 1, if the displacement of the mirror block 20 from the standard correct position usually occurs in only one direction (i.e., movement along only one axis, or rotation about one axis), then by detecting whether each of the intensities I1 through I5 of each of the images is darker or brighter than the standard brightness, the calculating device 105 can determine which direction the mirror block 20 must be moved. Therefore, only 1 bit of information is required for processing.

However, in the case that the mirror block 20 has been displaced along two or more axes, then more information may be required.

In Table 1, examples K through R illustrate examples of the mirror block 20 having been displaced in two directions from the standard correct position. In these cases, the intensities I1 through I5 are either very bright, very dark or have the standard brightness. However, the image patterns for each of the examples A through R, is unique and therefore, for the image patterns of examples K through R, only 1 bit of information is required in order to determine the direction in which the mirror block 20 should be moved.

However, other combinations of displacements in which the image pattern is similar to those listed above, but which have intensities that have more than one bright level and more than one dark level, 2 or more bits of information will be required.

If 8 bits of information are used, then the calculating device 105 can also determine the amount of displacement of the mirror block 20 from the standard correct position.

The methods of adjusting the location of the mirror block 20 based on the detected intensities I1 through I5 will be described below with reference to FIGS. 12A through 12D.

First Method

Figure 12B:
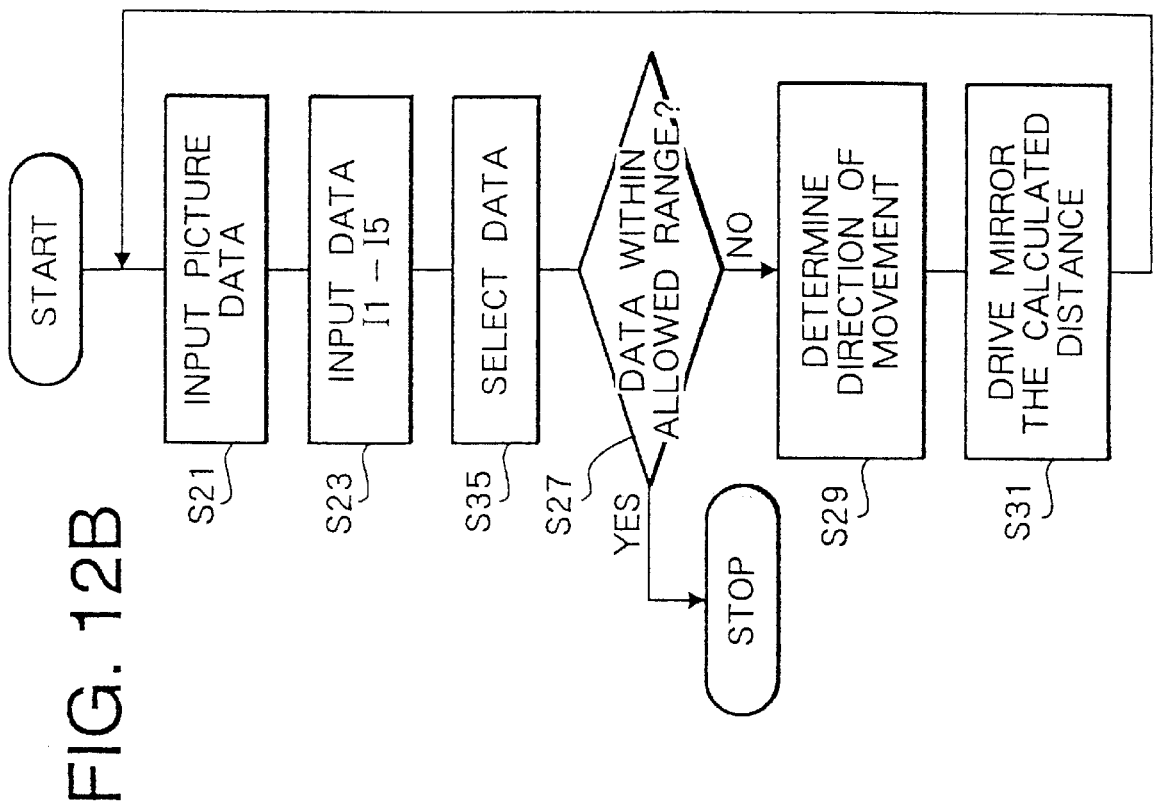
FIGS. 12A through 12D are flowcharts showing four different methods for adjusting the position of the mirror block according to the first embodiment of the present invention.
Figure 12A:
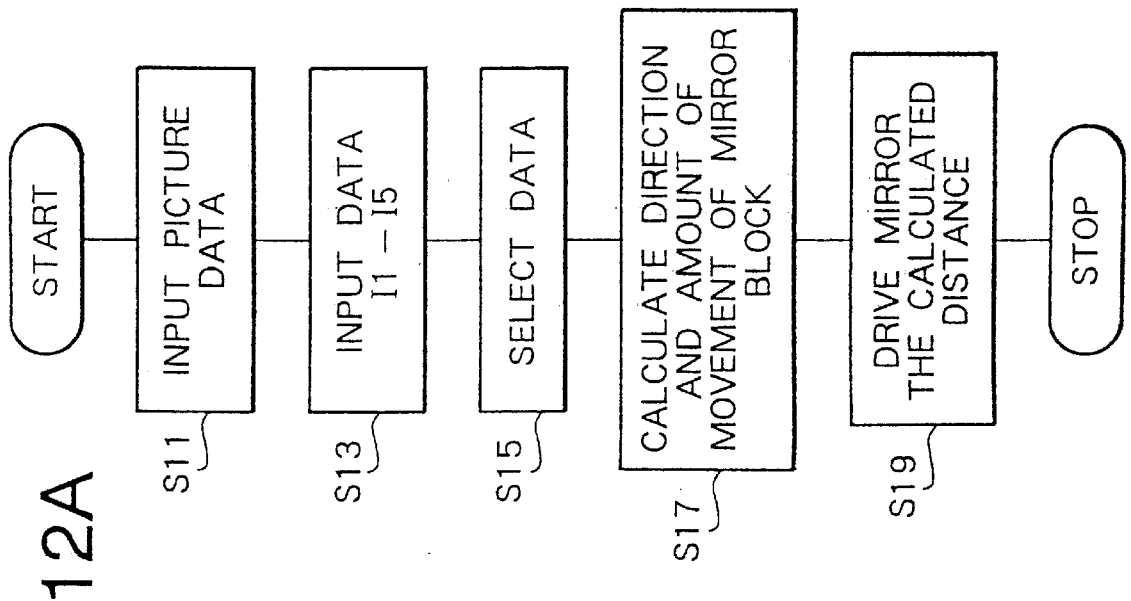

FIG. 12A shows a flowchart of a first method of adjusting the position of the mirror block 20. In this method, the amount of displacement necessary to position the mirror block 20 at the standard correct position is determined by solving a set of simultaneous linear equations. In this method, the number of intensities detected is equivalent to the number of degrees of freedom of the mirror block 20. Therefore, since the mirror block 20 has five degrees of freedom, five of the ten intensities (i.e. I1 through I5 for each of the left and right images) detected are used for determining the adjustment amount of the mirror block 20.

In step S11, the image data from the imaging devices 34a and 34b are transferred to the memories 101 and 102, respectively. Then in step S13, the intensities I1 through I5 for each of the left and right images are determined. In step S15, a total of five intensities of the ten intensities are selected. In step S17, the calculating device 105 uses simultaneous linear equations to determine the amount and direction of movement of the mirror block 20, required to move the mirror block 20 back to the standard correct position. The calculating device 105 then outputs a signal to the controller 106, which indicates the amount and direction of movement required to position the mirror block 20 at the standard correct position.

In step 19, the controller 106 controls the first motor 60 and the second motor 61 to drive the first gear 44a and the second gear 46 by a calculated amount, in order to move the mirror block 20 to the standard correct position. The routine then ends.

Thus, as described above, the first method can quickly calculate the amount and direction of movement required to move the mirror block 20 to the standard correct position, since the image data only needs to be detected once.

However, the first method requires that the intensity values change linearly with a change in displacement of the mirror block 20. If the mirror block 20 is located at a position where a rotation of the mirror block 20 is required in order to return the mirror block 20 to the standard correct position, another method of determining the amount and direction of movement of the mirror block 20 is required.

Second Method

FIG. 12B shows a second method of determining the amount and direction of movement of the mirror block 20, required to move the mirror block 20 to the standard correct position. In the second method, the calculating device 105, stores standard intensity values for the left and right images when the mirror block 20 is at the standard correct position. The actual intensity values are compared with the standard intensity values, and the mirror block 20 is moved based on a difference between the actual intensity values and the standard intensity values. Then the process is repeated until the two sets of values are the same.

Steps S21 through S25 are similar to steps S11 through S15 of the first method shown in FIG. 12A. Therefore, in step S21, the image data from the imaging devices 34a and 34b are transferred to the memories 101 and 102, respectively. Then in step S23, the intensities I1 through I5 for each of the left and right images are determined. In step S25, a total of five intensities of the ten intensities are selected.

In step S27, the calculating device 105 compares the intensities with the standard data, and determines whether the intensities are within an allowable range of the standard data by calculating the difference between the two sets of data using the least square method. If the difference between the two sets of data is less than a predetermined value (S27:Y), then the routine ends.

If the difference between the two sets of data is not less than the predetermined value (S27:N), then in step S29, the calculating device 105 determines the direction and amount of compensation required to move the mirror block 20 to the standard correct position.

In step 31, the controller 106 controls the first motor 60 and the second motor 61 to drive the first gear 44a and the second gear 46 by the calculated amount, in order to move the mirror block 20 to the standard correct position. Control then returns to step S21, where the above process is repeated.

As, described above, the process of measuring the intensities I1 through I5 for each of the left and right images, and the driving of the mirror block 20 to a new position in accordance with a difference between the measured intensities and the standard values, is repeated until the mirror block 20 is positioned at the standard correct position.

Third Method

Figure 12D:
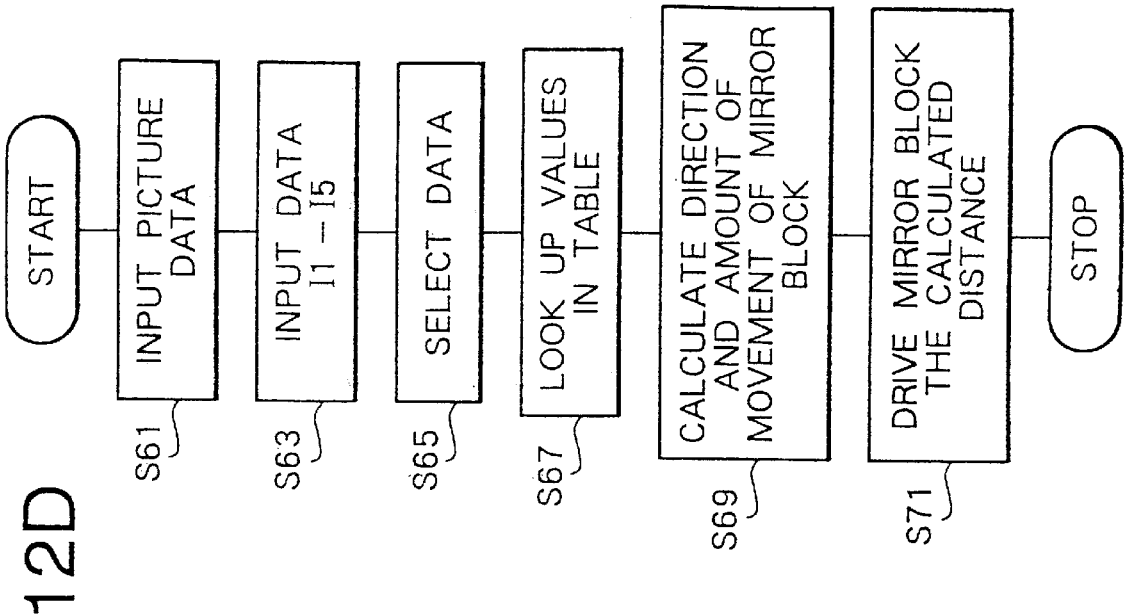
Figure 12C:
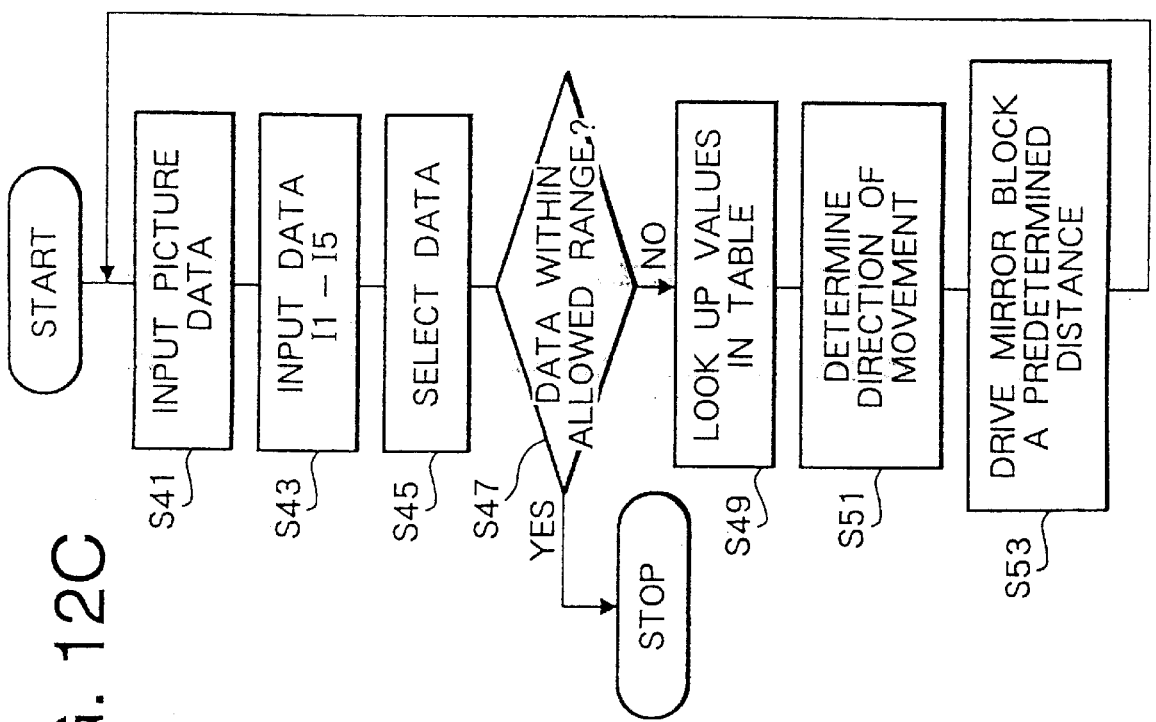

FIG. 12C shows a third method of determining the amount and direction of movement of the mirror block 20, required to move the mirror block 20 to the standard correct position. In the third method, a reference look up table which cross references displacement amounts with intensities (similar to Table 1) is used.

As shown in FIG. 12C, steps S41 through S49, are similar to the steps S21 through S29 of the second method shown in FIG. 12B.

Therefore, in step S41, the image data from the imaging devices 34a and 34b are transferred to the memories 101 and 102, respectively. Then in step S43, the intensities I1 through I5 for each of the left and right images are determined. In step S45, a total of five intensities of the ten intensities are selected.

In step S47, the calculating device 105 compares the intensities with the standard data, and determines whether the intensities are within an allowable range of the standard data by calculating the difference between the two sets of data using the least square method. If the difference between the two sets of data is less than a predetermined value (S47:Y), then the routine ends.

If the difference between the two sets of data is not less than the predetermined value (S47:Y), then in step S49 the calculating device 105 looks up a direction of movement for compensating the position of the mirror block 20 in accordance with the measured intensities. The controller 106 then controls the first motor 60 and second motor 61 to drive the mirror block 20 by a predetermined amount and in the direction determined from the look up table. The control then proceeds to step S41, where the above process is repeated, until the difference between the intensities and the standard values is below the predetermined amount.

As, described above, the process of measuring the intensities I1 through I5 for each of the left and right images, and the driving of the mirror block 20 to a new position in accordance with a value in the reference table, is repeated until the mirror block 20 is positioned at the standard correct position.

Fourth Method

FIG. 12D shows a fourth method of determining the amount and direction of movement of the mirror block 20, required to move the mirror block 20 to the standard correct position. The fourth method also uses the reference look up table which cross references displacement amounts with intensities used in the third method. However, the fourth method is also similar to the first method, where the procedure is executed only once, and the mirror block 20 is moved to the standard correct position immediately.

As shown in FIG. 12D, steps S61 through S65 are similar to the steps S11 through S15 of the second method shown in FIG. 12A.

Therefore, in step S61, the image data from the imaging devices 34a and 34b are transferred to the memories 101 and 102, respectively. Then in step S63, the intensities I1 through I5 for each of the left and right images are determined. In step S65, a total of five intensities of the ten intensities are selected.

Then in step S67, the calculating device 105 looks up a direction and amount of compensation corresponding to the measured intensities. The controller 106 then controls the first motor 60 and second motor 61 to drive the mirror block 20 by the amount and in the direction determined from the look up table, in step S71. The mirror block 20 will then be located at the standard correct position.

As described above, there are four methods of positioning the mirror block 20 at the standard correct position. The first and fourth method determine an amount and direction of movement required to move the mirror block 20 to the standard correct position, while the second and third method determine a direction that the mirror block 20 should be moved in order to attain the standard correct position. However, the mirror block 20 is moved by a predetermined amount and the process is repeated until it is determined that the mirror block 20 is at the standard correct position.

Thus, only direction data needs to be determined when using the second and third method, and therefore only 1 or 2 bits of data is required. The first and fourth methods will position the mirror block 20 at the standard correct position more quickly, but require 8 bits of data.

Second Embodiment

Figure 13:
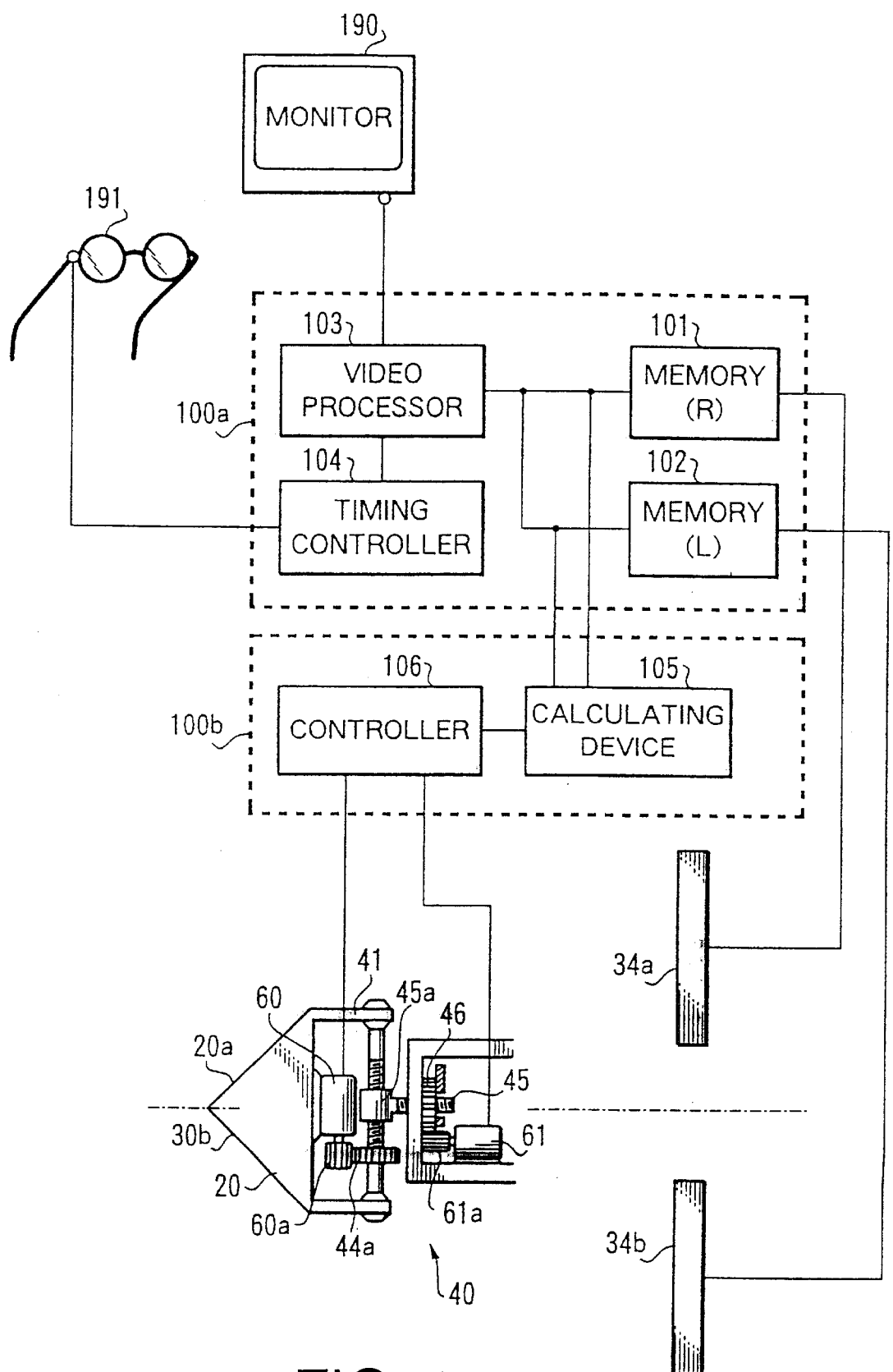
FIG. 13 shows a block diagram of a processing device used with the stereoscopic endoscope shown in FIG. 1A according to a second embodiment of the present invention.

FIG. 13 shows a block diagram of a stereoscopic endoscope according to a second embodiment of the present invention. The second embodiment is similar to the first embodiment shown in FIG. 1, with the common parts having the same reference numerals.

The second embodiment is provided with an observation processing device 100a and an adjustment processing device 100b, instead of the processing device 100 of the first embodiment.

As shown in FIG. 13, the observation processing device 100a is provided with the memories 101 and 102, the video processor 103, and the timing controller 104. The adjustment processing device 100b is provided with the calculating device 105, and the controller 106. Further, the memories 101 and 102 are electrically connected to the calculating device 105.

The movement of the mirror block 20 to the standard correct position is done in a similar manner to that described for the first embodiment above. However, the adjustment of the position of the mirror block 20 is usually done in the factory, and therefore, it is only necessary to connect the adjustment processing device 100b to the endoscope during the adjustment operation. Furthermore, during normal operation of the stereoscopic endoscope, only the observation processing device 100a is required. This reduces the overall size of the stereoscopic endoscope unit required in the field.

Third Embodiment

Figure 14:
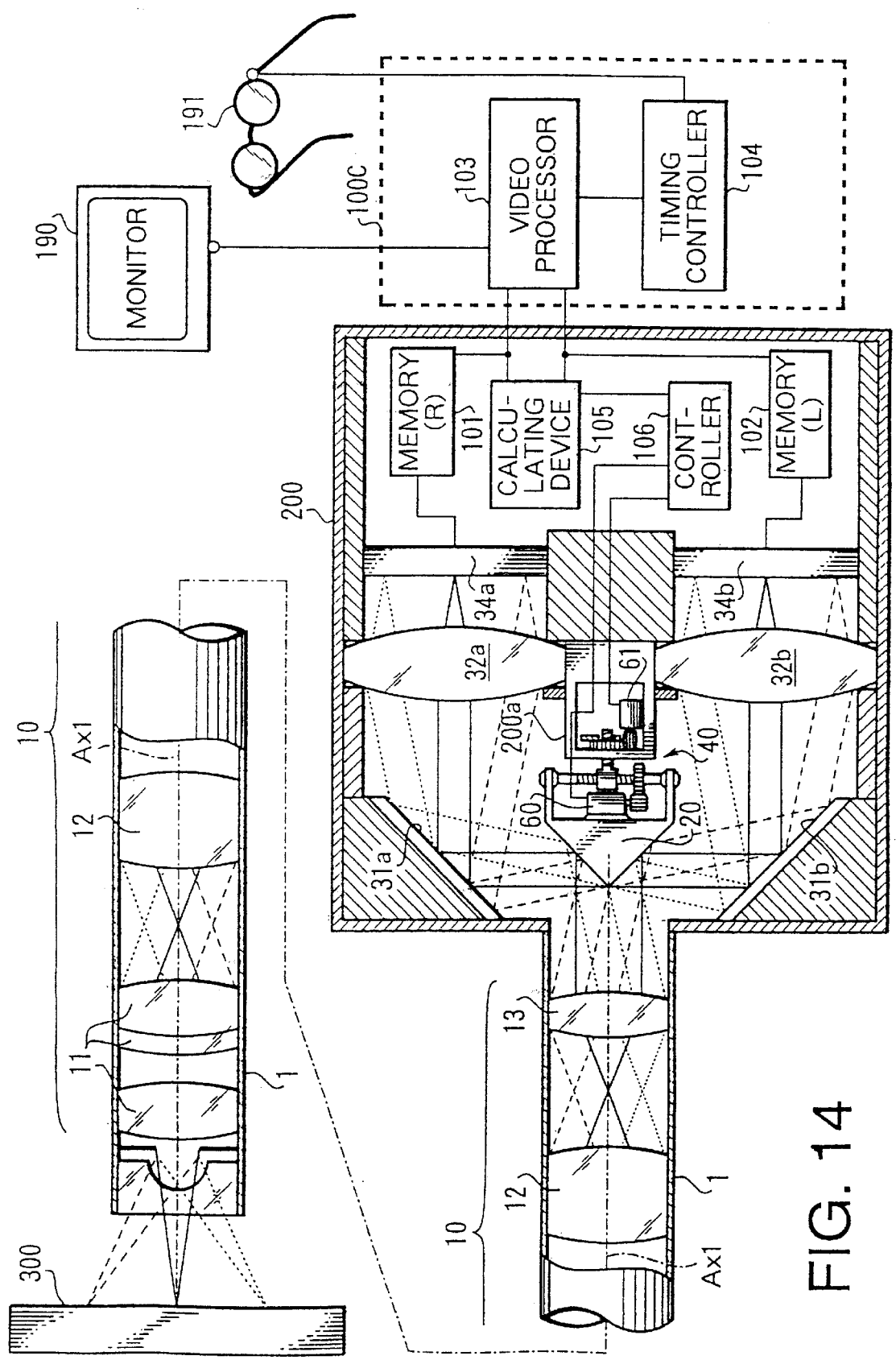
FIG. 14 shows a sectional view of a stereoscopic endoscope and block diagram of the stereoscopic endoscope, according to third embodiment of the present invention.

FIG. 14 shows a sectional view of a stereoscopic endoscope according to a third embodiment of the present invention. The third embodiment includes the insertion portion 1 and an observing portion 200.

The observing portion 200 is similar to the observing portion 2, with the adjustment mechanism 40 attached to a holding wall 200a, and other common parts having the same reference numerals. However, the observing portion 200 includes the calculating device 105, the memories 101 and 102, and the controller 106. Therefore, the adjustment of the position of the mirror block 20 can be done without connecting an external device. This facilitates the readjustment of the position of the mirror block 20 in the field, as well as the initial adjustment done in the factory. Further, the overall size of the stereoscopic endoscope is reduced.

An observation processor 100c which includes the video processor 103 and the timing controller 104 can be connected to observing portion 200 to allow viewing of the images displayed on the monitor 190 while wearing the pair of glasses 191.

Fourth Embodiment

Figure 15A:
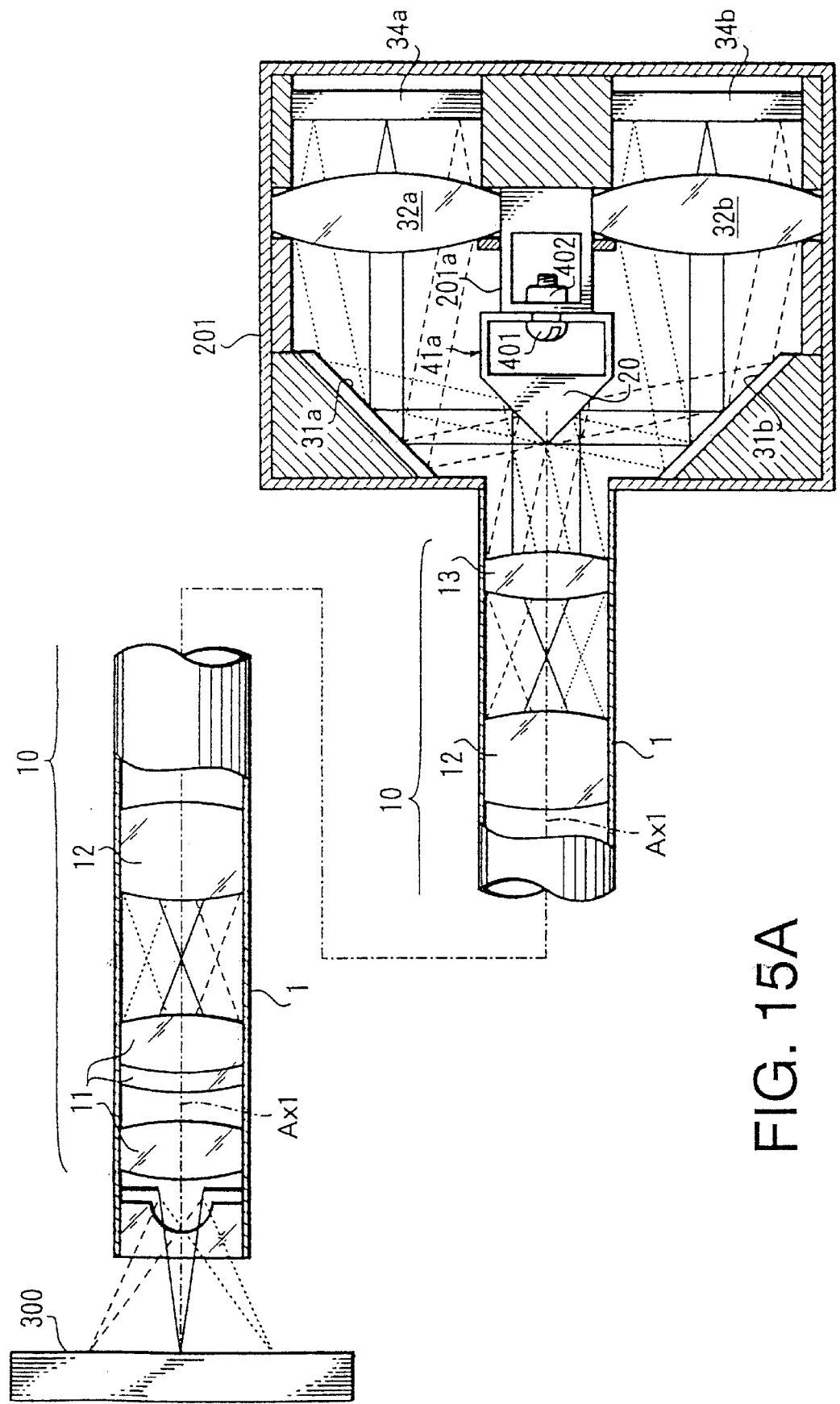
FIG. 15A shows a sectional view of a stereoscopic endoscope according to fourth embodiment of the present invention.

FIG. 15A shows a sectional view of a stereoscopic endoscope according to a fourth embodiment of the present invention. The fourth embodiment includes the insertion portion 1 and an observing portion 201.

The observing portion 201 is similar to the observing portion 2, with the common parts having the same reference numerals. However, in the fourth embodiment, the mirror block 20 is attached to a mounting frame 41a, which is attached to a holding wall 201a. A mounting screw 401 and nut 402 secure the mounting frame 41a to the holding wall 201a. The mounting screw 401 passes through a hole 201b of the holding wall 201a. The shape of the hole 201b is slightly oblong in the y direction, to allow the mounting screw to be offset from the center of the hole 201b in the y direction, as shown in FIG. 15B.

Figure 15B:
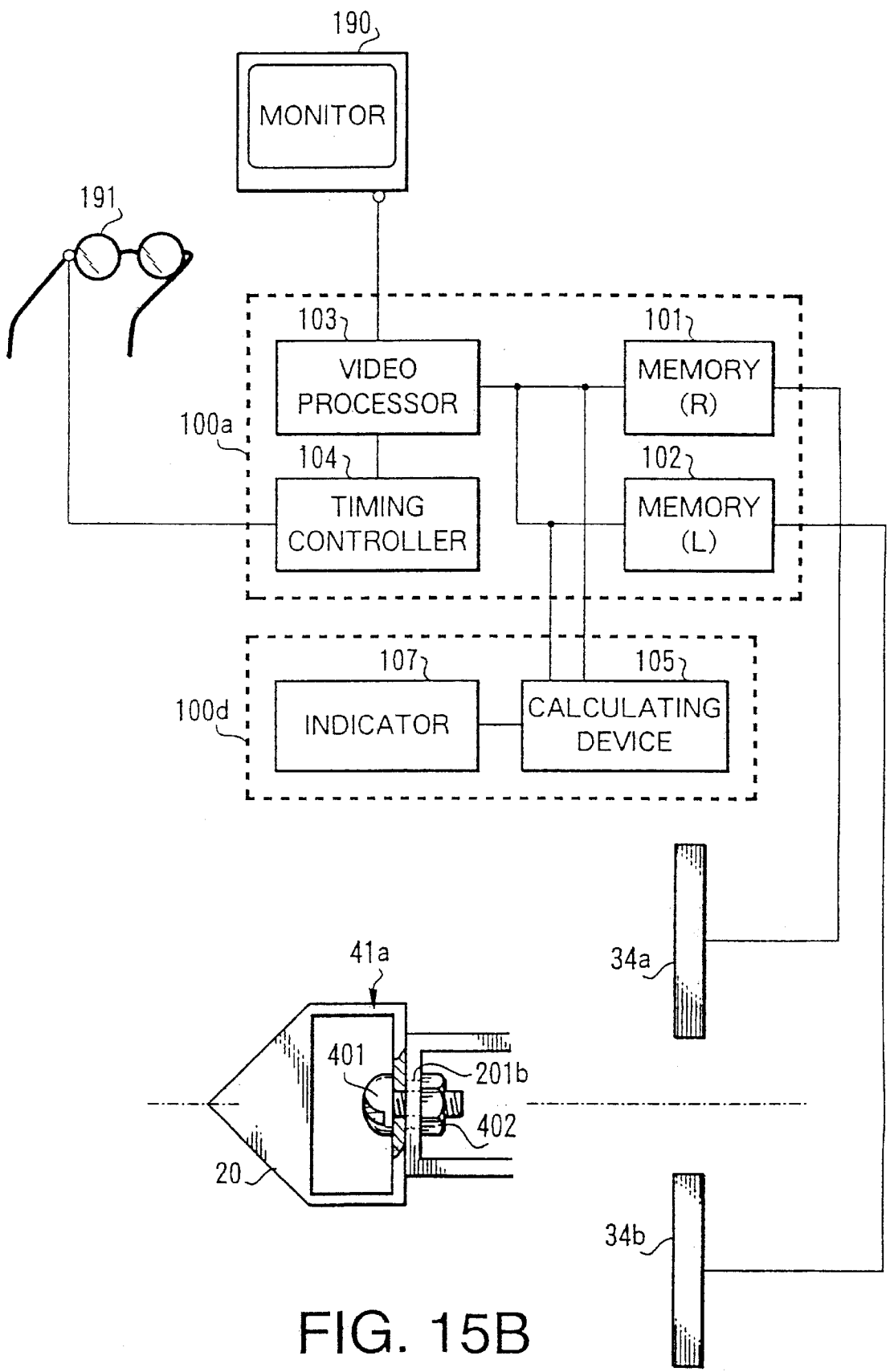
FIG. 15B shows a block diagram of the processing device used with the stereoscopic endoscope shown in FIG. 15A according to the fourth embodiment of the present invention.

As further shown in FIG. 15B, the observation processing device 100a has the same arrangement as the second embodiment. An adjustment processing device 100d is provided with the memories 101 and 102, the calculating device 105 and correction value indicator 107. The calculating device 105 determines the displacement of the mirror block 20 from the standard correct position based on the image data, and the indicator 107 displays the correction value for the y-axis direction as numerical information. The correction value refers to the direction and amount of movement required to position the mirror block 20 at the standard correct position.

Therefore, by using the numerical information, the mounting block can be manually positioned by adjusting the position of the mounting screw 401 with respect to the center of the hole 201b.

As described above, the fourth embodiment of the endoscope does not require a driving mechanism to move the mirror block 20 to the standard correct position, and therefore the number of parts and the cost of manufacturing the endoscope is reduced.

Fifth Embodiment

Figure 16:
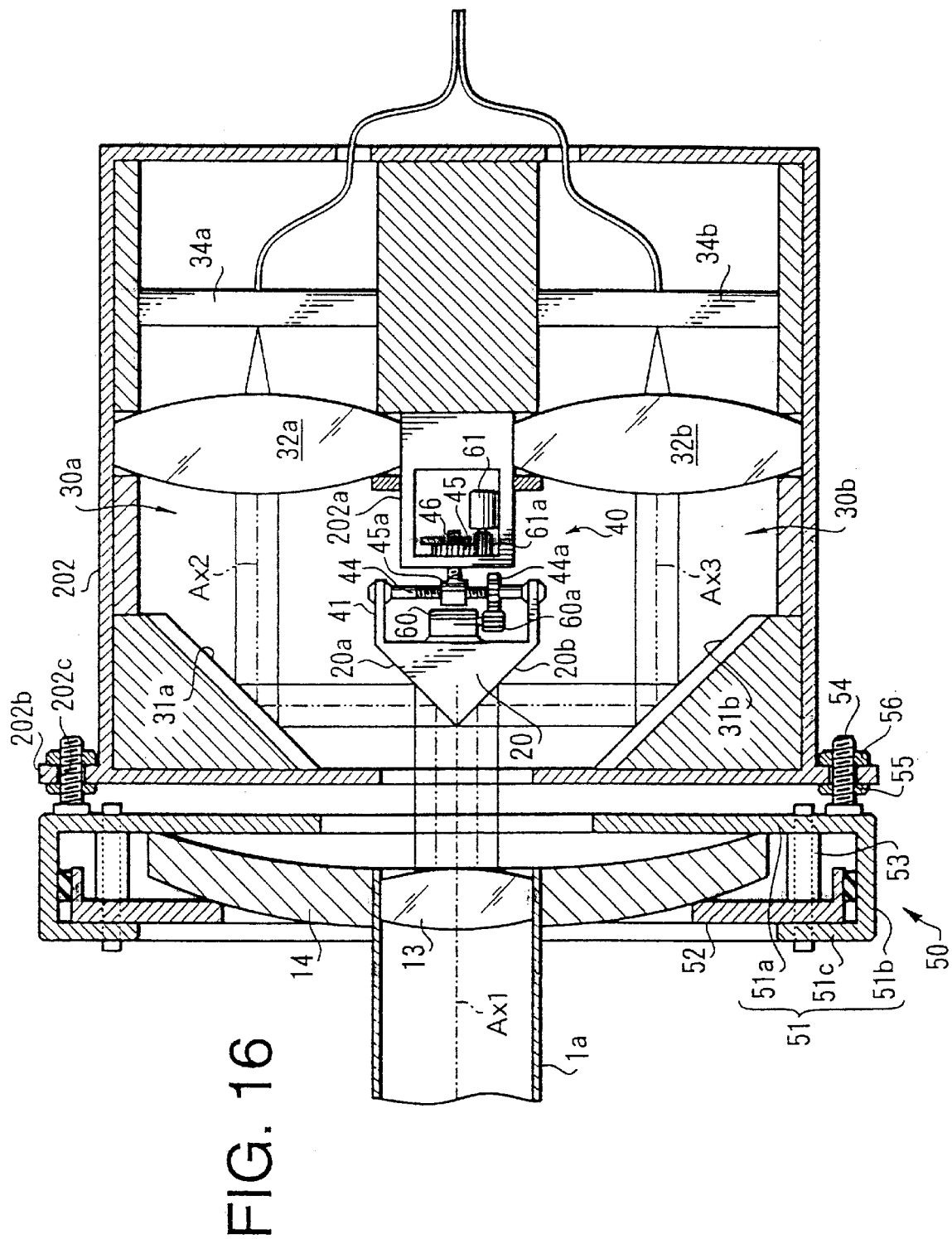
FIG. 16 shows a sectional view of an observing portion of a stereoscopic endoscope according to a fifth embodiment of the present invention.

FIG. 16 shows a sectional view of a stereoscopic endoscope according to a fifth embodiment of the present invention. The fifth embodiment includes an insertion portion 1a and an observing portion 202.

The observing portion 202 is similar to the observing portion 2, and the insertion portion 1a is similar to the insertion portion 1, with the adjustment mechanism 40 attached to a holding wall 202a and the other common parts having the same reference numerals. However, the insertion portion 1a is designed to be used with a non-stereoscopic endoscope, and is attached to the observing portion 202 using an adapter 50. The insertion portion 1a is normally provided with a hood 14 that is attached around the circumference of the image-side end of the insertion portion 1a. The hood 14 allows an observer to directly view the image formed by the insertion portion 1a, while preventing external ambient light from entering the observer's eye. The observing portion 202 is connected with the insertion portion 1a through the adapter 50 that is clamped on the hood 14.

The adapter 50 comprises a holding ring 51 that is attached to the hood 14 from the observing portion side. Clamps 52 are attached to the holding ring 51 using bolts 53. Further, the clamps 52 are positioned on the insertion portion side of the hood 14. By tightening the bolts 53, the space between the clamps 52 and the holding ring 51 is reduced, and the hood 14 is securely attached to the holding ring 51. In FIG. 16, each of the clamps 52 is shown attached to the holding ring 51 using a single bolt. However, three bolts should be used to in order to securely attach the hood 14 to the holding ring 51.

The holding ring 51 consists of a base plate portion 51a that has an opening to allow light to pass through, a cylindrical portion 51b that encloses the hood 14, and an inner flange portion 51c to which the clamps 52 are fixed. The hood 14 is clamped between the base plate portion 51a of the holding ring 51 and the clamps 52. In the preferred embodiment the clamps 52 are L-shaped.

The holding ring 51 is attached to an outer flange 202b of the observing portion 202 using at least three adjusting bolts 54.

The adjusting bolts 54 are fed through holes 202c and are fixed to the outer flange 202b by fastening nuts 55 and 56, which are positioned on either side of the outer flange 202b. Since the positions of the nuts 55 and 56 are changed together, the distance between the insertion portion 1 and the observing portion 202 along the adjusting bolt 54 changes. Therefore, the relative attitude of the insertion portion 1a and the observing portion 202 can be adjusted three-dimensionally by adjusting each of the adjusting bolts 54 independently.

Further, the adjusting mechanism 40 is more effective in the fifth embodiment, since the relative attitude of the insertion portion 1a and the observing portion 202 can be changed in the fifth embodiment.

Sixth Embodiment

Figure 17:
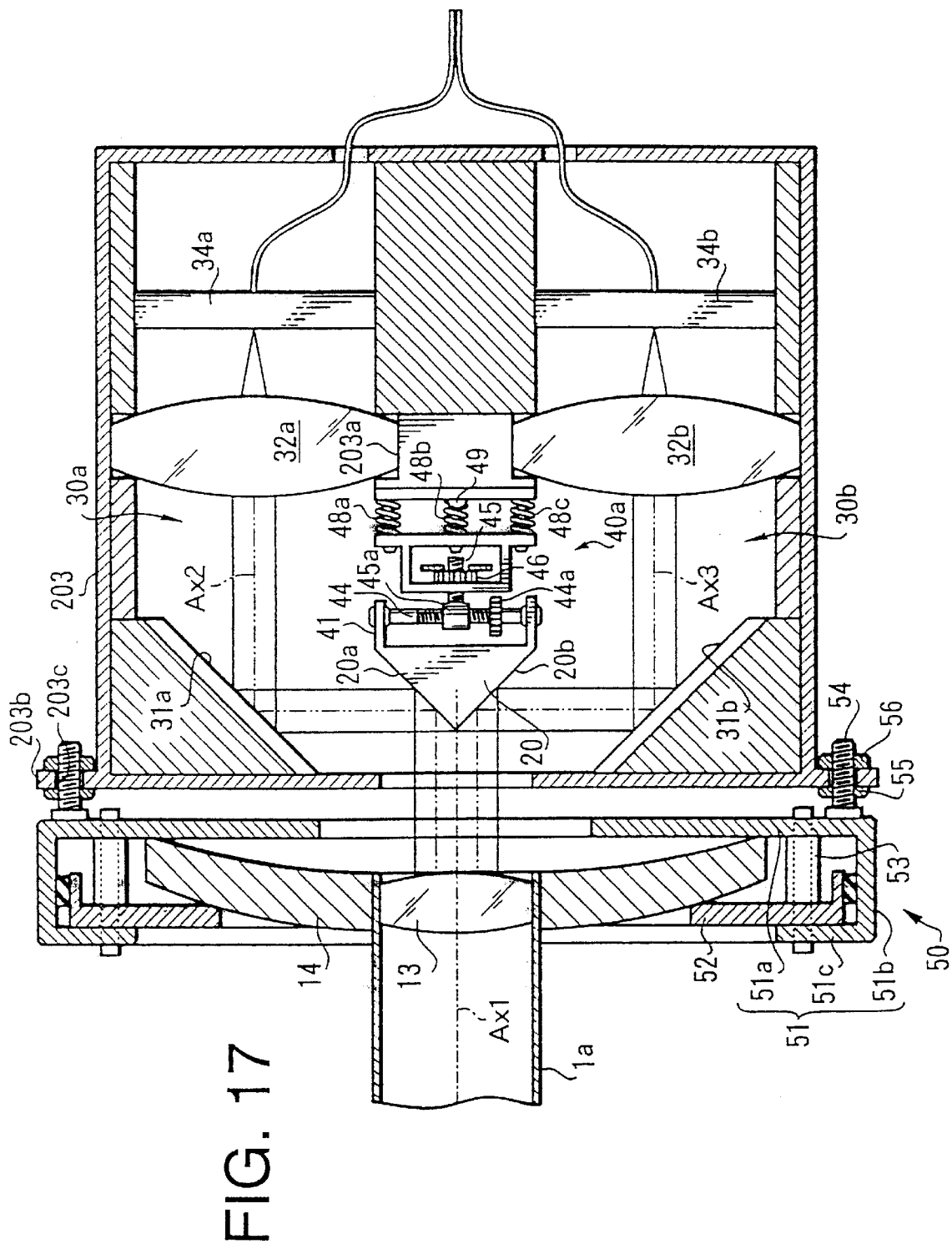
FIG. 17 shows a sectional view of an observing portion of a stereoscopic endoscope according to a sixth embodiment of the present invention.

FIG. 17 shows a sectional view of a stereoscopic endoscope according to a sixth embodiment of the present invention. The sixth embodiment includes the insertion portion 1*a* and an observing portion 203. The observing portion 203 is similar to the observing portion 202, with the common parts having the same reference numerals. In this case, the adapter 50 is attached to a flange 203*b* by the bolts 54 which pass through the holes 203*c* and are fastened using the nuts 55 and 56.

Figure 18A:
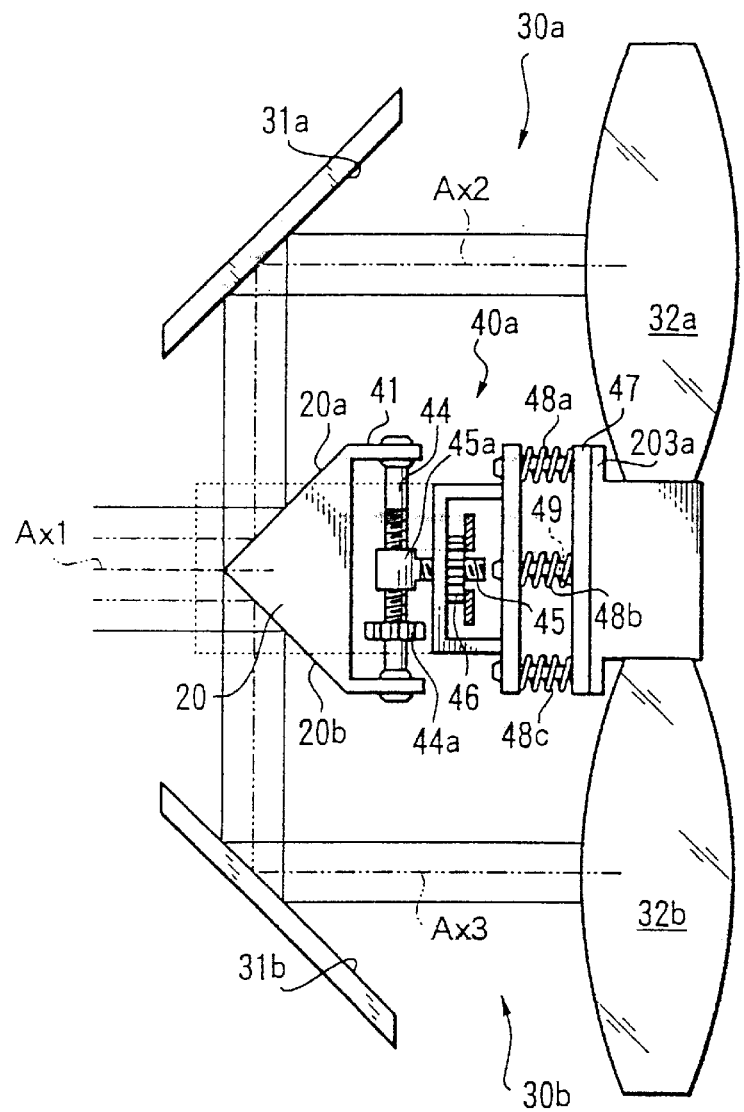
FIGS. 18A and 18B are enlarged views of a mirror block shown in FIG. 17.
Figure 18B:
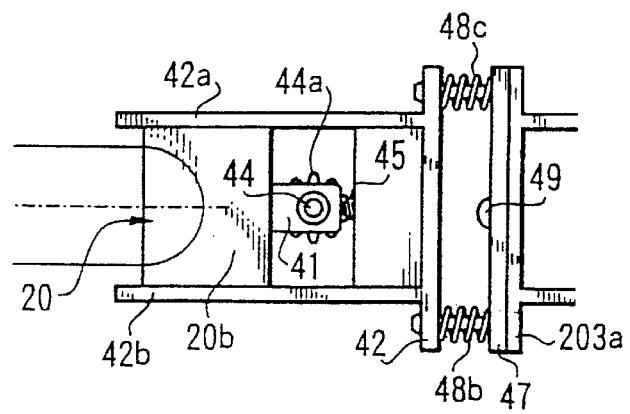

FIGS. 18A and 18B show an enlarged view of an adjustment mechanism 40*a* of the observing portion 203. The mechanism 40*a* includes a holding base 42 which holds the mirror block 20 and permits movement along the x-axis direction and the y-axis direction.

The holding base 42 is supported by a rotation plate 47 with three adjusting bolts 48*a*, 48*b* and 48*c*. The rotation plate 47 is attached to a holding wall 203*a* of the observing portion 203 by an axis pin 49 so as to permit rotation about the axis pin 49. Compression springs are arranged around the adjusting bolt 48*a*, 48*b* and 48*c* to maintain the attitude of the holding base 42.

The attitude of the holding base 42 changes by tightening or loosening the adjusting bolts 48*a*, 48*b* and 48*c*. Further, the adjustment of these bolts allows the mirror block 20 to be rotated about the y-axis and the z-axis. The adjustment of the rotation plate 47 allows the mirror block 20 to be rotated about the x-axis.

Therefore, as described above, the mirror block 20 can be adjusted along the 5 degrees of freedom.

Seventh Embodiment

Figure 19:
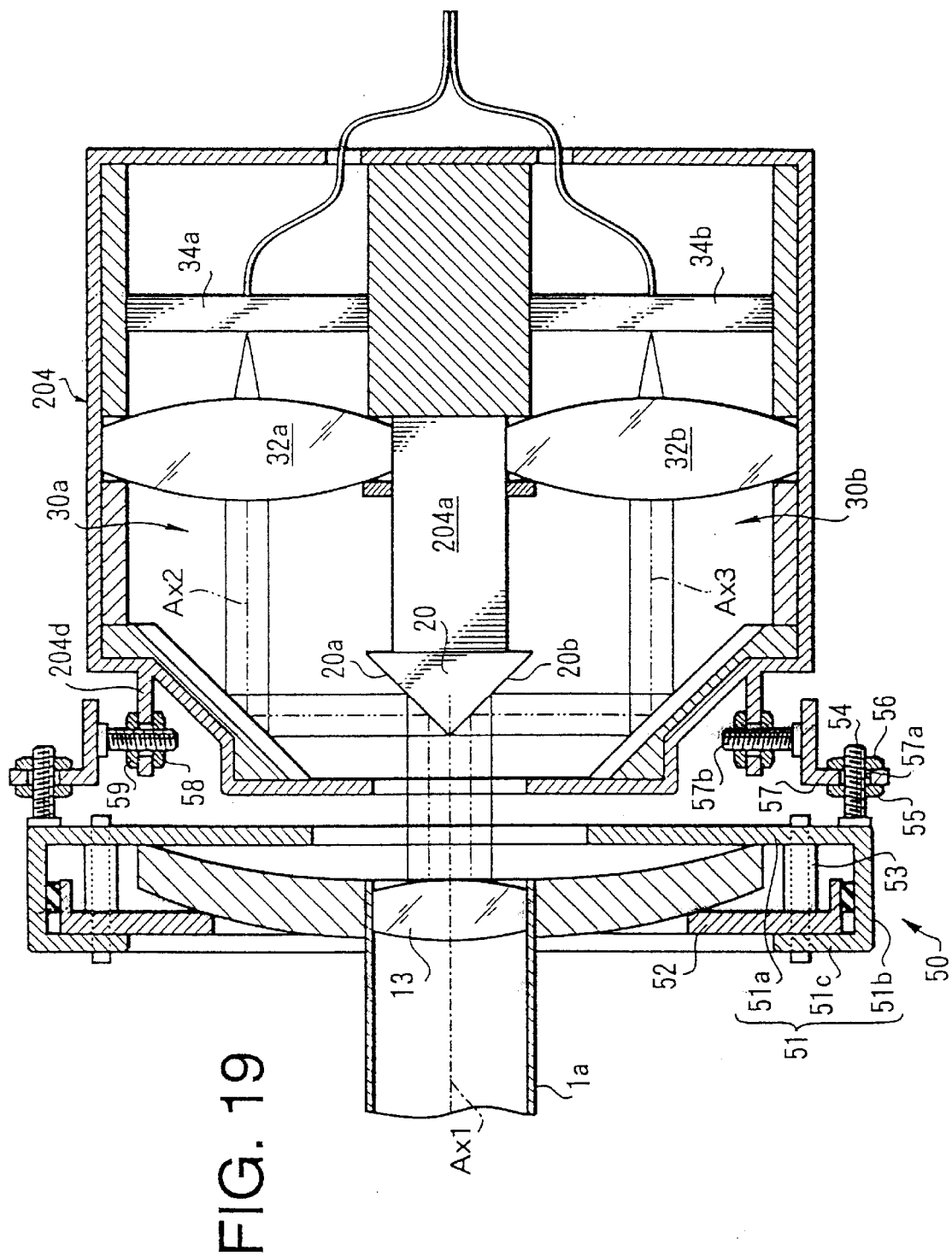
FIG. 19 shows a sectional view of an observing portion of a stereoscopic endoscope according to a seventh embodiment of the present invention.

FIG. 19 shows a sectional view of a stereoscopic endoscope according to a seventh embodiment of the present invention. The seventh embodiment includes the insertion portion 1*a* and an observing portion 204. The observing portion is similar to the observing portion 202, with the common parts having the same reference numerals. However, the mirror block 20 is directly attached to a holding wall 204*a* of the observing portion 204.

In the seventh embodiment, the adapter 50 is connected to the observing portion 204 through two L-shaped coupling plates 57. The mirror block 20 is fixed to the observing portion 204 such that its position cannot be adjusted.

The adapter 50 has the three adjusting bolts 54, with at least two of the adjusting bolts 54 being attached to the observing portion 204 through the coupling plates 57. The nuts 55 and 56 that are positioned on either side of each coupling plate 57, and secure one end of the coupling plate 57 to one of the adjusting bolts 54. The other end of the coupling plate 57 is provided with fixing screw 57*b*.

The coupling plate 57 is fastened to a fixing plate 204*d* of the observing portion 204 using nuts 58 and 59 which are fastened to the fixing screw 57*b* on both sides of the fixing plate 204*d*.

The adjustment of the nuts 58 and 59 allows the relative attitude of the insertion portion 1*a* to the observing portion 204 to be changed in the y-axis direction. Further, by adjusting the nuts 55 and 56 that are attached to the adjusting bolts 54, the relative attitude of the insertion portion 1*a* to the observing portion 204 may be changed in order to change the three-dimensional effect.

Therefore, as described above, the change in the three-dimensional effect of the image can be achieved without using the adjustment mechanism 40. This decreases the number of parts, and reduces the cost of manufacturing the stereoscopic endoscope.

Eighth Embodiment

Figure 20:
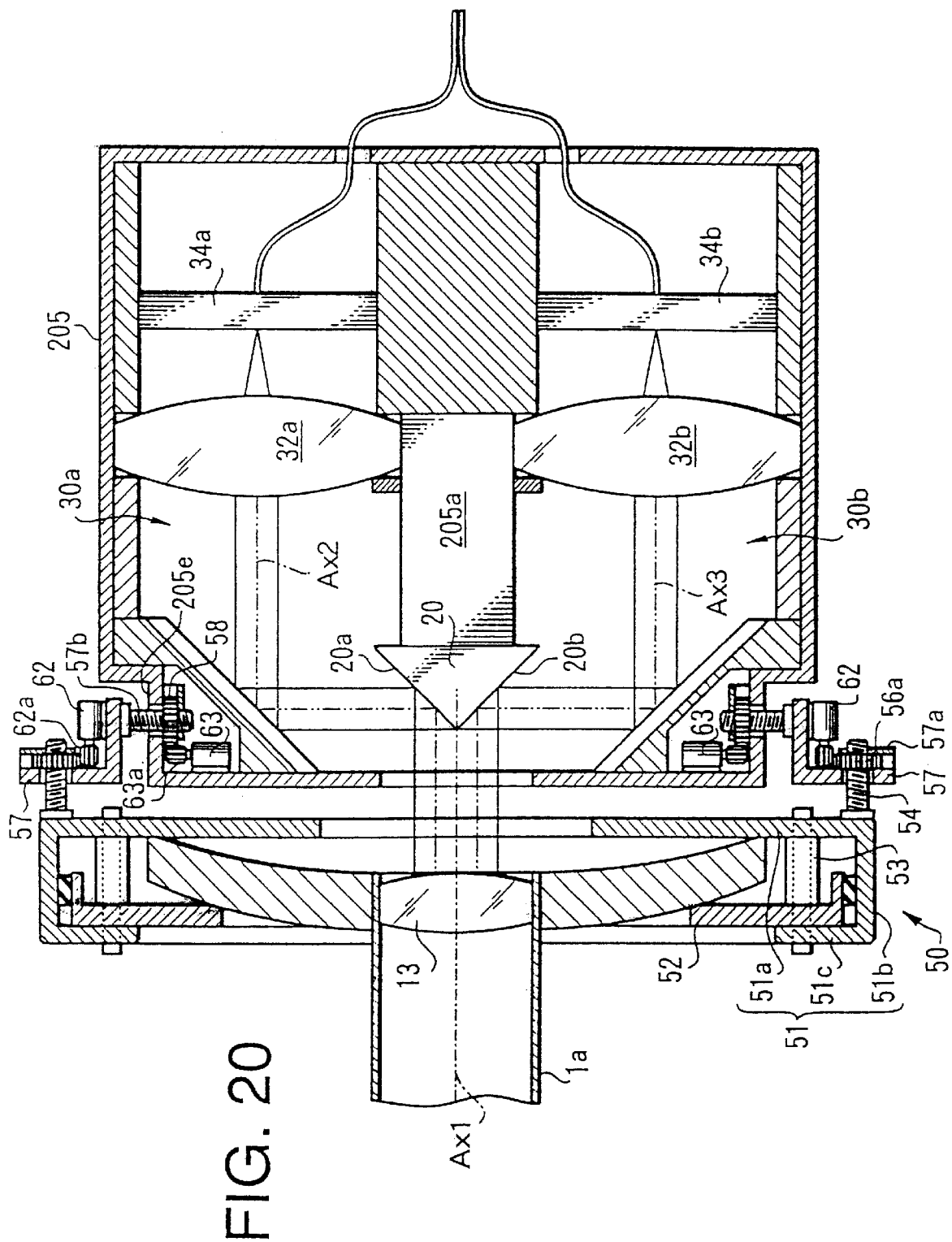
FIG. 20 shows a sectional view of an observing portion of a stereoscopic endoscope according to an eighth embodiment of the present invention.

FIG. 20 shows a sectional view of a stereoscopic endoscope according to an eighth embodiment of the present invention. The eighth embodiment includes the insertion portion 1*a* and an observing portion 205. The observing portion 205 is similar to the observing portion 204, with the mirror block 20 attached to a holding wall 205 and the other common parts having the same reference numerals. Thus, the eighth embodiment is similar to the seventh embodiment shown in FIG. 19, except for the construction around each coupling plate 57. In the eighth embodiment, two coupling plates are provided. The construction around one of the coupling plates 57 will be described below.

A first adjusting gear 56*a* is installed on the coupling plate 57 and rotates about an axis. The adjusting bolt 54 is screwed through the opening 57*a*. The first adjusting gear 56*a* is meshed with the adjusting bolt 54 and a first pinion 62*a* of a first motor 62. The first motor 62 is mounted on the coupling plate 57.

A second adjusting gear 58 is installed inside the observing portion 205, and rotates about an axis. The fixing screw 57*b* is screwed through an opening 205*e* formed in the observing portion 205. The second adjusting gear 58 is meshed with the fixing screw 57*b* and with a second pinion 63*a* of a second motor 63. The second motor 63 is mounted on an inside wall of the observing portion 205.

According to the construction shown in FIG. 20, since the two first motors 62 are driven simultaneously, the position of the insertion portion 1*a* along the y axis can be adjusted. Further as the two second motors 63 are driven simultaneously, the position of the insertion portion 1*a* can be adjusted in the x-axis direction.

Therefore, the three-dimensional effect on the observed image can be controlled by driving the pair of first motors 62 and the pair of second motors 63.

Ninth Embodiment

Figure 21A:
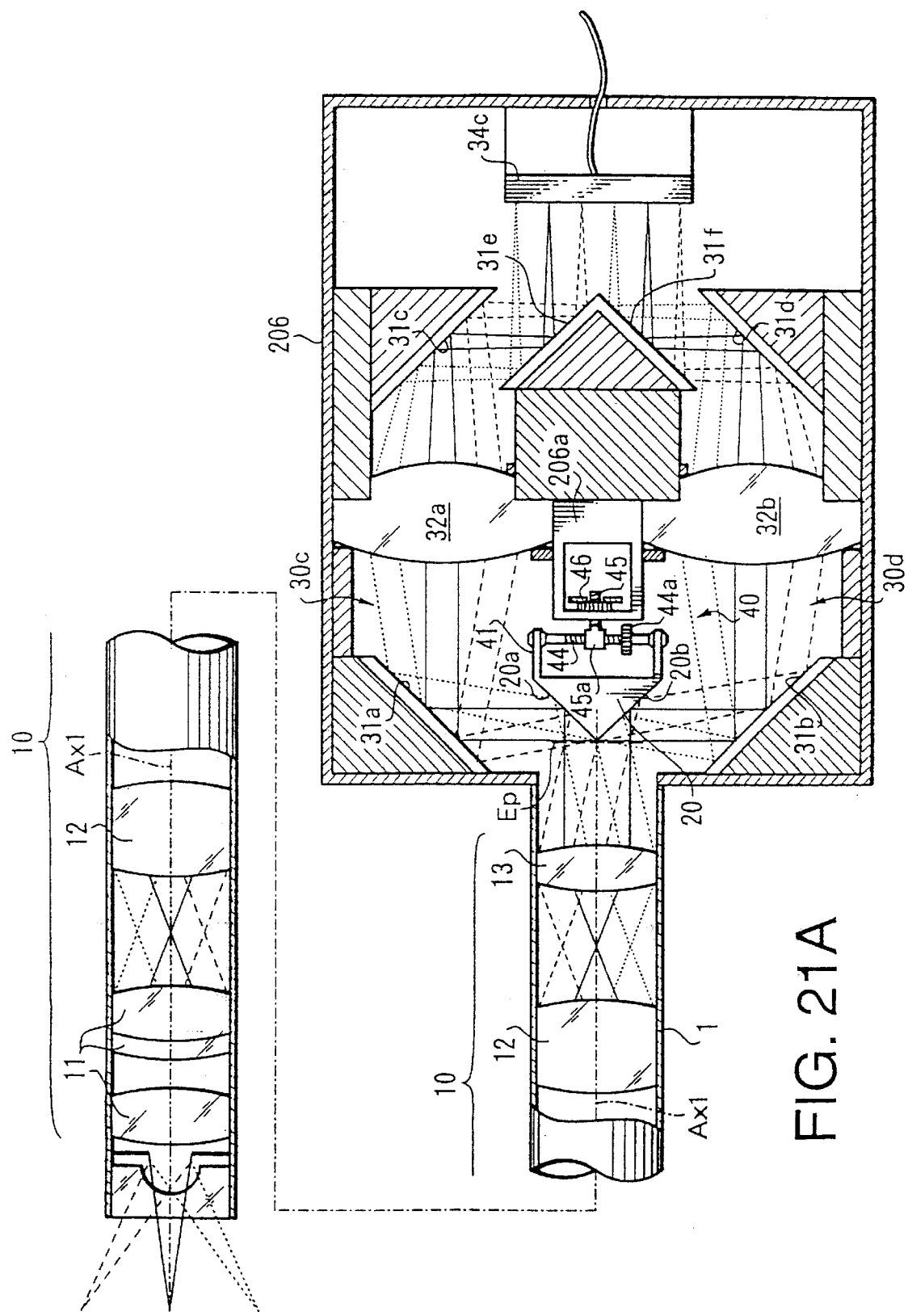
FIG. 21A shows a sectional view of a stereoscopic endoscope according to a ninth embodiment of the present invention.

FIG. 21A shows a sectional view of a stereoscopic endoscope according to a ninth embodiment of the present invention. The ninth embodiment includes the insertion portion 1 and an observing portion 206. The observing portion 206 is similar to the observing portion 2 shown in FIG. 1A, with the adjustment mechanism 40 attached to a holding wall 206*a*, and the other common parts having the same reference numerals. However, the observing portion 206 has a single imaging device 34*c*, and two secondary optical systems 30*c* and 30*d*. The secondary optical systems 30*c* and 30*d* are similar to the secondary optical systems 30*a* and 30*b* but include a pair of imaging lenses 32*c* and 32*d*, a second pair of mirrors 31*c* and 31*d*, and a third pair of mirrors 31*e* and 31*f*.

As shown in FIG. 21A, the light divided by the mirror block 20 is transmitted by the pair of the secondary optical systems 30*c* and 30*d*, and a pair of images are formed on the imaging device 34*c*. The images are formed on separate areas of the imaging device 34*c* and do not overlap each other.

Figure 21B:
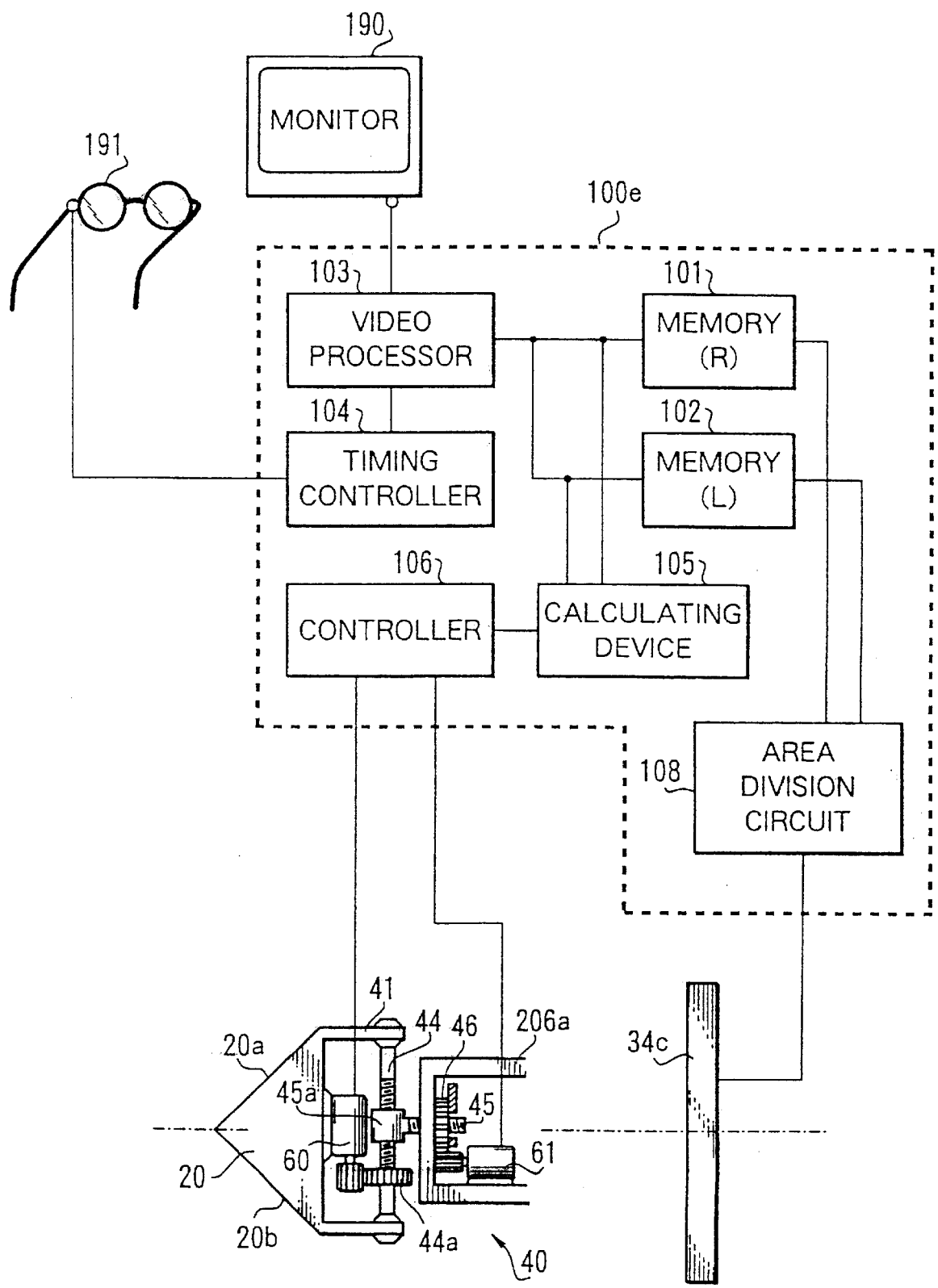
FIG. 21B shows a block diagram of a processing device used with the stereoscopic endoscope shown in FIG. 21A according to the ninth embodiment of the present invention.

The output data from the imaging device 34*c* is input into a processing device 100*e* that processes the data to display a picture of the object on the monitor 190, as shown in FIG. 21B. The processing device 100*e* is similar to the processing device 100*a*, with similar parts having common reference numerals.

The output data from the imaging device 34*c*, which is the combined data of the left and right pictures, is separated by an area division circuit 108 into a pair of images that correspond to the left and right image formed by each the secondary optical system 30*c* and 30*d*. The separated picture data are stored into the picture memories 101 and 102 and are alternatively displayed in time sequence on the monitor 190, as described above.

Therefore, in the ninth embodiment, only a single imaging device is required, and thus the cost of manufacturing the stereoscopic endoscope can be reduced.

Tenth Embodiment

Figure 22A:
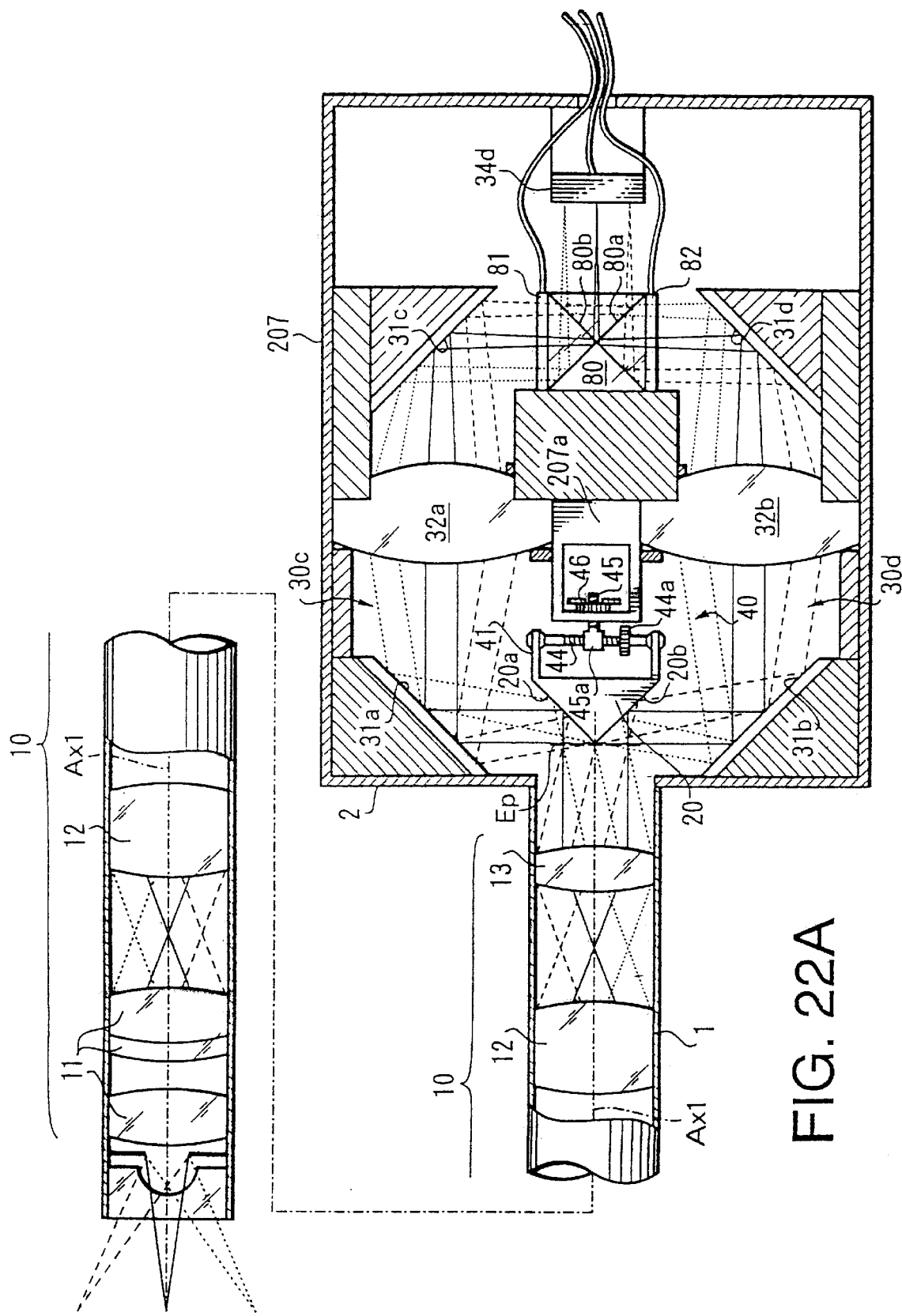
FIG. 22A shows a sectional view of a stereoscopic endoscope according to a tenth embodiment of the present invention.

FIG. 22A shows a sectional view of a stereoscopic endoscope according to a tenth embodiment of the present invention. The tenth embodiment includes the insertion portion 1 and an observing portion 207.

The observing portion 207 is similar to the observing portion 206 shown in FIG. 21, with the adjustment mechanism 40 attached to a holding wall 207a, and the other common parts having the same reference numerals. However, in the observing portion 206 the images of the pair of the secondary optical systems 30c and 30d are formed in the same area of an imaging device 34d. As a result, the imaging device 34d of the tenth embodiment is only half the size of the imaging device 34c used in the ninth embodiment. Further, a half mirror prism 80 replaces the third pair of mirrors 31e and 31f. Each of the half mirrors 80a and 80b receives light through one of a pair of liquid crystal shutters 81 and 82.

Since the images formed by both of the secondary optical systems 30c and 30d, completely overlap on the imaging device 34d, then one of the left and right images must be blocked while the other image is detected in order to independently receive the left and right images. Therefore, the liquid crystal shutters 81 and 82 alternatively transmit light reflected from the second mirrors 31c and 31d, to the half mirror prism 80.

Figure 22B:
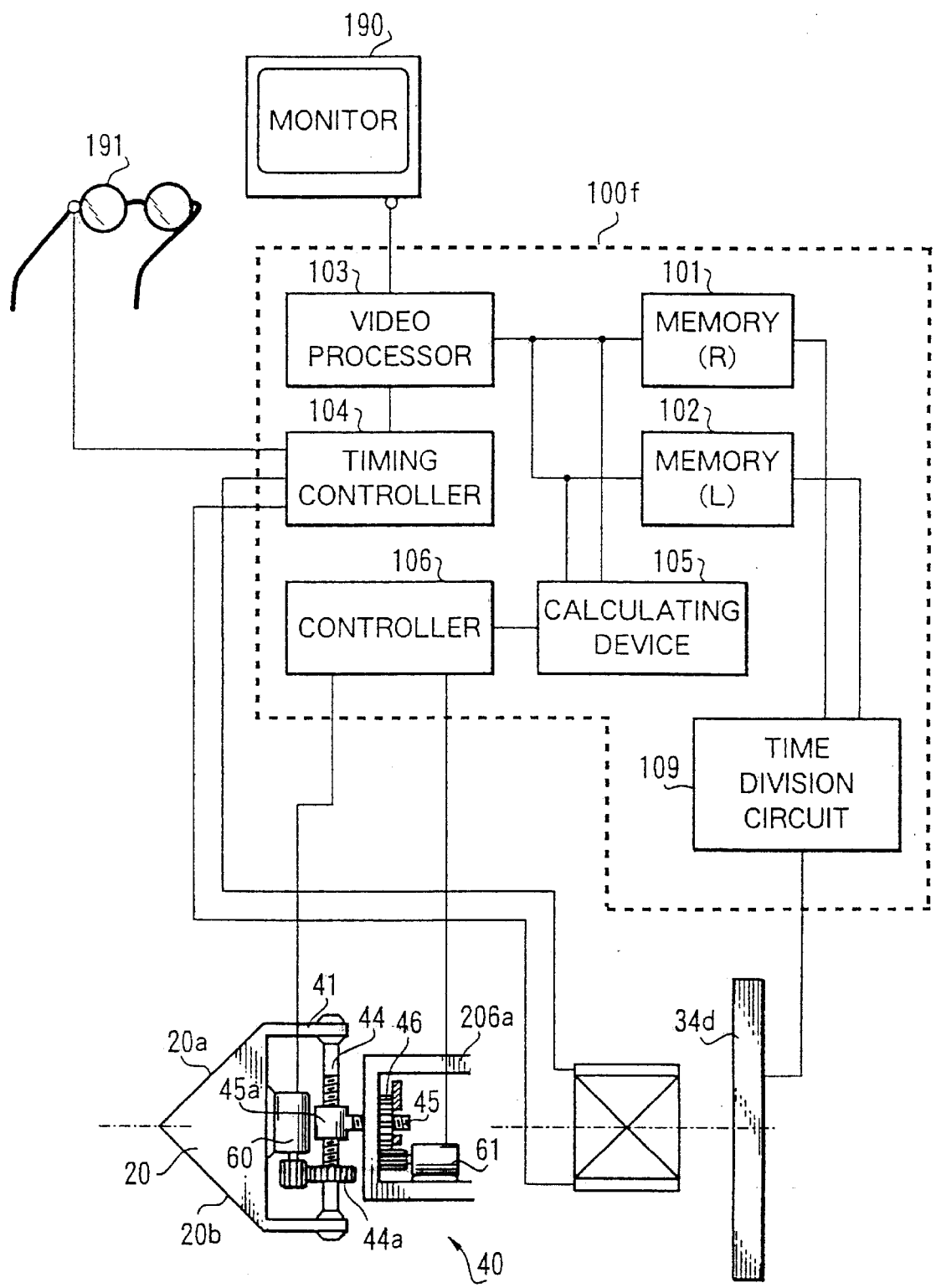
FIG. 22B shows a block diagram of a processing device used with the stereoscopic endoscope shown in FIG. 22A according to the tenth embodiment of the present invention.

As shown in FIG. 22B, a processing device 100f may be provided which is similar to the processing device 100 and which has the timing controller 104 which controls the liquid crystal shutters 81 and 82, a time division circuit 109, and the shutters of the glasses 191, to operate in synchronism, thereby ensuring that the proper image is seen by the corresponding eye. The output data of the imaging device 34d is divided into the left and right picture data by the time division circuit 109 with each picture being separately stored into the memories 101 and 102, respectively. The video processor 103 alternatively displays the left and right pictures according to clock signal from the timing controller 104 and the shutters of the glasses 191 are driven synchronously with the switching of the picture on the monitor 190.

Eleventh Embodiment

Figure 23:
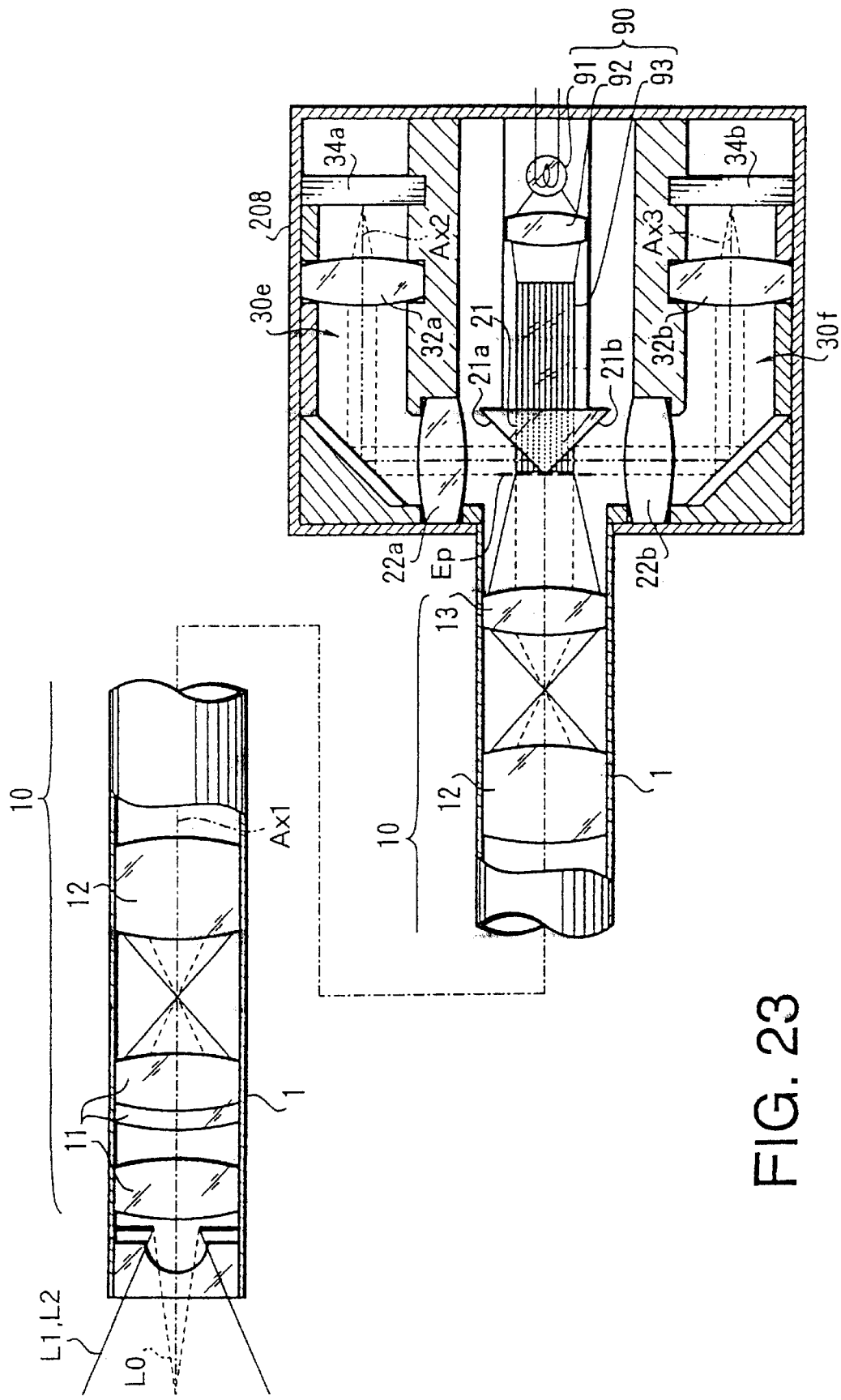
FIG. 23 shows a sectional view of a stereoscopic endoscope of a eleventh embodiment of the present invention.

FIG. 23 shows a sectional view of a stereoscopic endoscope according to an eleventh embodiment of the present invention. The eleventh embodiment of the stereoscopic endoscope includes the insertion portion 1, and an observing portion 208. The observing portion 208 has a mirror block 21, a pair of secondary optical system 30e and 30f, and an illumination unit 90, used to illuminate the object being observed with the endoscope.

The secondary optical systems 30e and 30f are similar to the secondary optical systems 30a and 30b of the observing portion 2, except that imaging lenses 22a and 22b are used instead of the imaging lenses 35a and 35b. The imaging lenses 22a and 22b are positioned between the mirror block 21 and the mirrors 31a and 31b, respectively. Further, the mirror block 21 is fixed in position.

The illumination unit 90 includes a light source 91a, condenser lens 92 and an optical fiber bundle 93. Two light beams L1 and L2 emitted from the illumination unit 90 are transmitted through the insertion portion 1 to the object to be viewed. The illumination unit 90 is arranged so that the light beam emitted from the light source 91 does not interfere with the light beam incident on the mirror block 21 that is reflected by the object.

Figure 24:
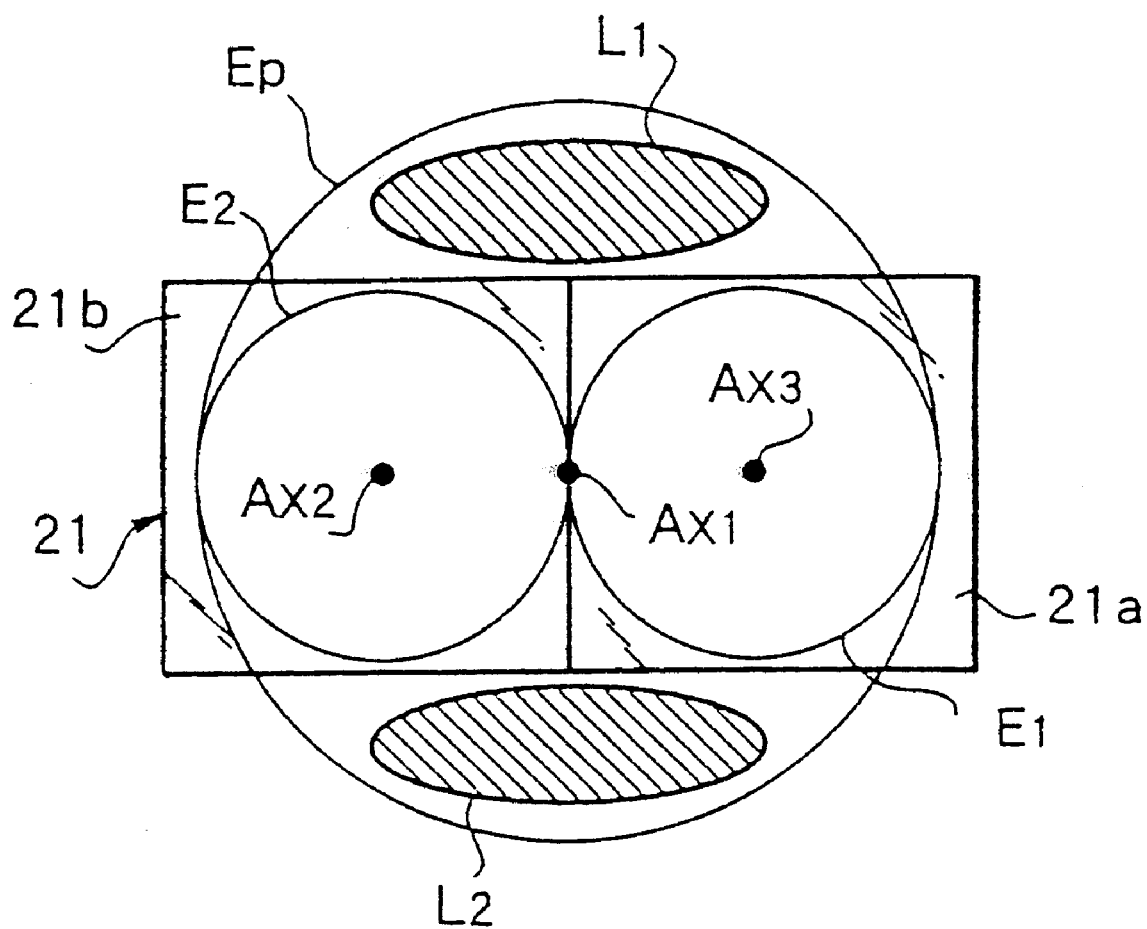
FIG. 24 is a front view of a mirror block viewed from an object side, showing a relationship between an illumination light beam and an observing field of an exit pupil of a primary optical system of the stereoscopic endoscope shown in FIG. 23.

FIG. 24 is a front view of the mirror block 21 viewed from the object side, showing a relationship of the illuminating light beams L1 and L2, and the observing fields E1 and E2 on the exit pupil Ep of the primary optical system 10. As shown in FIG. 24, the illuminating light beams L1 and L2 do not overlap the observing fields E1 and E2.

Therefore, as described above, an optical fiber is not required to transmit the illuminating light to the end of the insertion portion 1. Therefore, the cost of manufacturing the stereoscopic endoscope can be reduced.

Twelfth Embodiment

Figure 25:
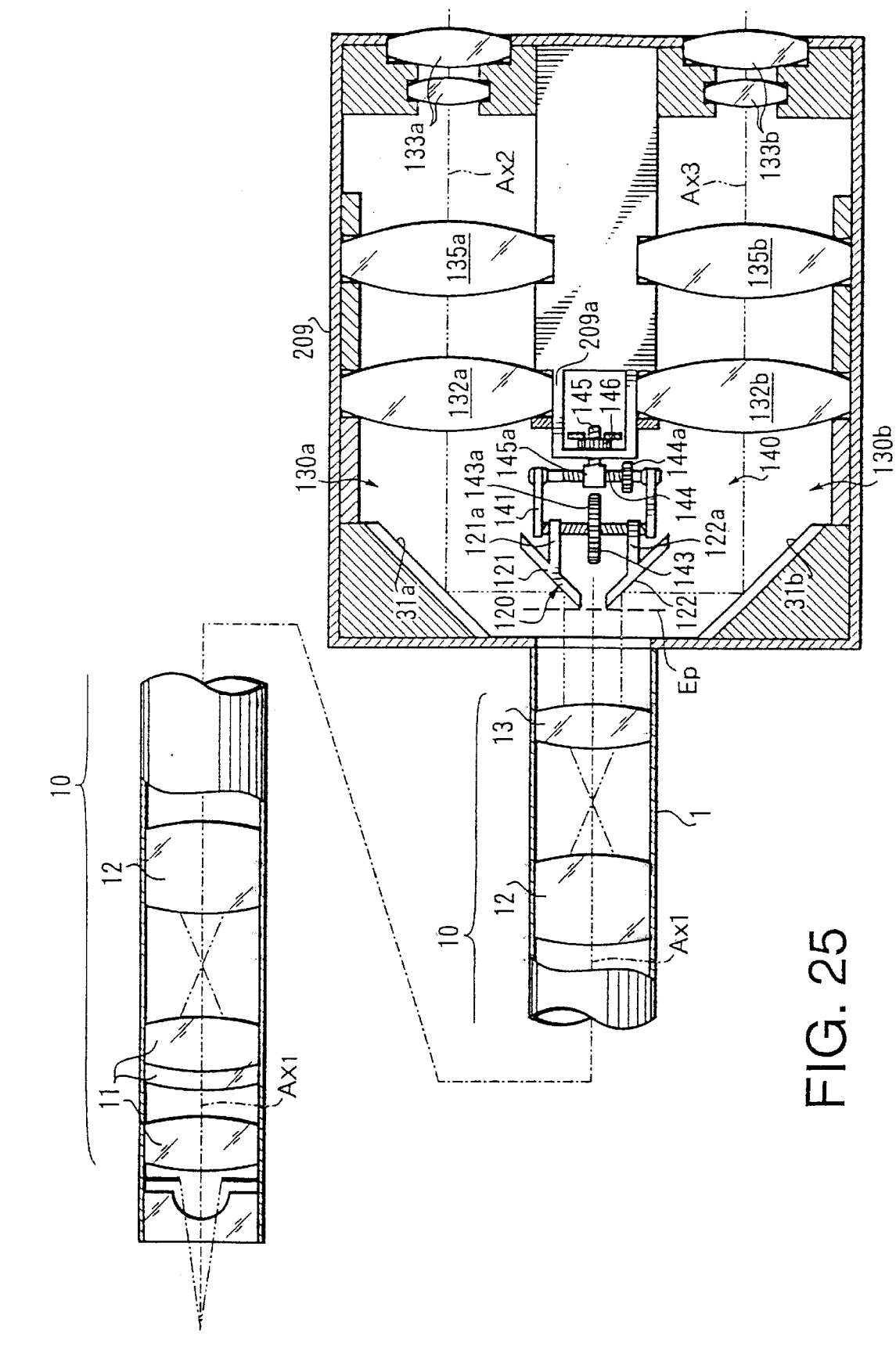
FIG. 25 is a sectional view of a stereoscopic endoscope according to a twelfth embodiment of the present invention.

FIG. 25 shows a sectional view of a stereoscopic endoscope according to a twelfth embodiment of the present invention. The twelfth embodiment includes the insertion portion 1 and an observing portion 209.

The observing portion 209 is similar to the observing portion 2 of the first embodiment, and includes a pupil dividing mechanism 120, a first secondary optical system 130a and a second secondary optical system 130b. The pupil dividing mechanism 120 consists of two mirrors 121 and 122. A distance between the two mirrors 121 and 122 can be changed in the y-axis direction (i.e., the left-right direction), by an adjusting mechanism 140.

The first secondary optical systems 130a includes mirrors 31a, imaging lenses 132a and 135a, and an eyepiece lens 133a. The secondary optical systems 130b includes mirrors 31b, imaging lenses 132b and 135b, and an eyepiece lens 133b. The eyepiece lenses 133a and 133b allow an observer to directly view the object.

The adjusting mechanism 140 includes a holding frame 141, which is formed on a base portion of the pupil dividing mechanism 120, and a first screw 144, which is fitted into the holding frame 141. A first gear 144A is meshed with the first screw 144. By rotating the first gear 144A, the first screw 144 is moved in the y direction.

A second screw 145 is fitted through a holding wall 209a of the observing portion 209. A nut portion 145a formed on the head of the second screw 145 is engaged with the first screw 144. A second gear 146 which is meshed with the second screw 145, is installed inside the holding wall 209a. By rotating the second gear 146 the screw 145 is moved in the x direction.

A third adjusting screw 143 is also supported by the holding frame 141. Stems 121a and 122a that are formed behind the mirrors 121 and 122 have threaded through holes, and are threaded with the third adjusting screw 143.

Figure 26A:
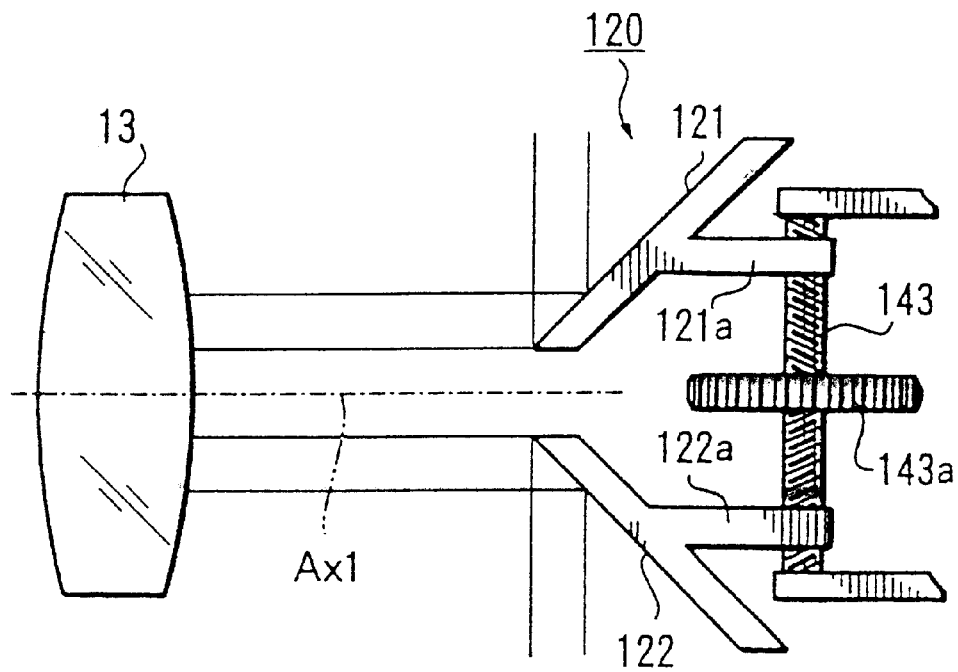
FIG. 26A is an enlarged top view of a pupil dividing mechanism of the stereoscopic endoscope shown in FIG. 25.
Figure 26B:
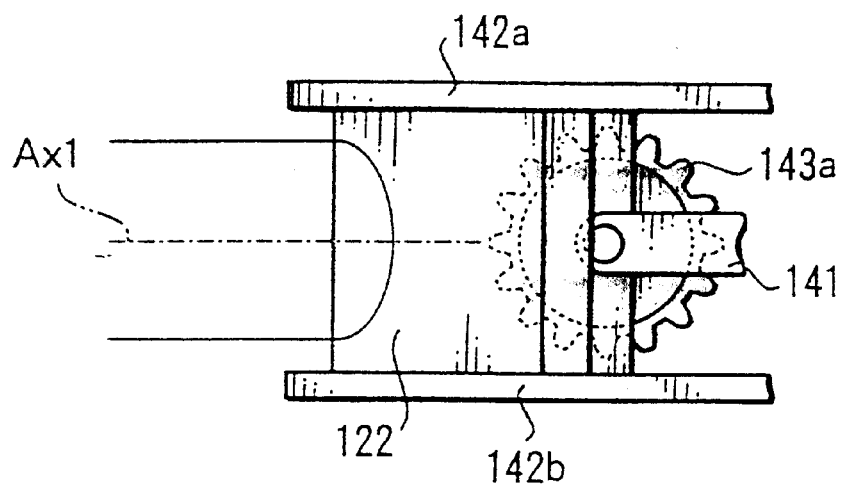
FIG. 26B is an enlarged side view of the pupil dividing mechanism of the stereoscopic endoscope shown in FIG. 25.

As shown in FIG. 26A, a third adjusting gear 143a is formed at the center of the third adjusting screw 143. Further, the third adjusting screw 143 is formed such that a direction of the threading of the adjusting screw 143 on one side of the adjusting gear 143a is opposite to a direction of the threading of the adjusting screw 143 on the other side of the adjusting gear 143a. FIG. 26B shows a side view of the pupil dividing mechanism 120. The pupil dividing mechanism 120 is arranged between guide plates 142a and 142b so that the rotation of adjusting gear 143a results in the linear movement of the mirrors 121 and 122 along the axis of the screw 143, as described above.

The position of the mirrors 121 and 122 are changed synchronously, in the x-axis direction and the y-axis direction by rotating the first and second adjusting gears 144a and 146, respectively. When the positions of each of the mirrors 121 and 122 are correctly adjusted, a tip 121b of the mirror 121 and a tip 122b of the mirror 122 coincide with the optical axis Ax1 of the primary optical system 10 and a plane which includes the exit pupil.

The distance between the mirrors 121 and 122 is adjusted by rotating the third adjusting gear 143a. When the third adjusting gear 143a is rotated in one direction, the mirrors 121 and 122 are separated from each other. When the third adjusting gear 143a is rotated in the opposite direction, the mirrors 121 and 122 are moved closer together. The third adjusting gear 143a may be driven manually or by using a motor.

As described above, light travels from the exit pupil Ep and is incident on the mirrors 121 and 122. By changing the distance between the mirrors 121 and 122, a distance traveled by the light from the exit pupil Ep to the mirrors 121 and 122, will change. The three-dimensional effect of the stereoscopic image viewed in the observing portion 209 varies according to the distance that the light has traveled. The effect of the change in the distance that the light has traveled will be described below.

Figure 27A:
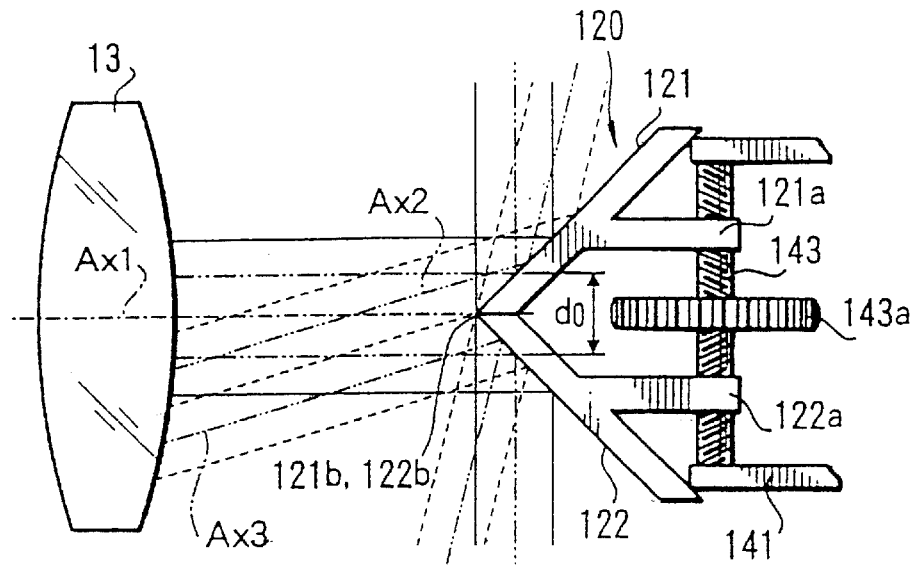
FIG. 27A is a top view of mirrors of the pupil dividing mechanism showing light paths when the mirrors are positioned closest to each other.
Figure 27B:
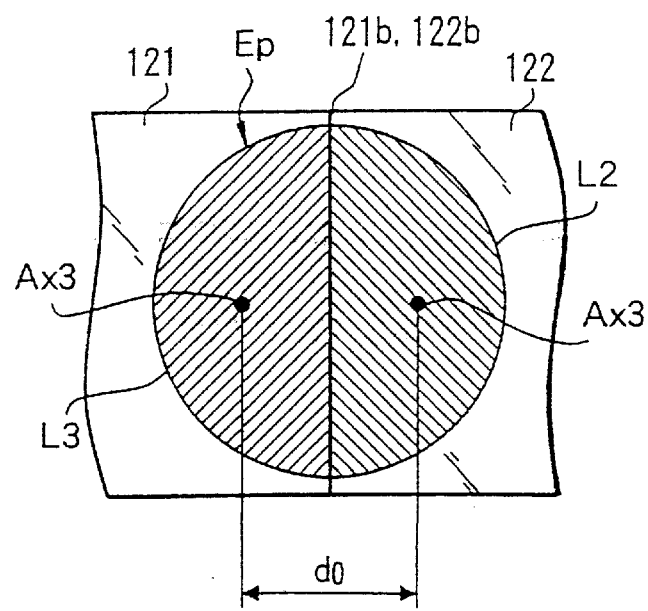
FIG. 27B is a front view of the mirrors shown in FIG. 27A viewed from an object side.

FIG. 27A is a top view of the mirrors 121 and 122 showing a path of the light incident on the mirrors 121 and 122 when the tips 121b and 122b of the mirrors 121 and 122 contact each other. FIG. 27B is a front view of the mirrors 121 and 122 when the tips 121b and 122b of the mirrors 121 and 122 contact each other. Under this condition, since the distance traveled by the light is equal to the minimum value do, the three-dimensional effect on the observed image is small. This is preferable for viewing an object that is located at a point near to the objective lens 11. Further, the amount light that is transmitted to the secondary optical systems 130a and 130b is a maximum, and therefore, a bright image is observed.

Figure 28A:
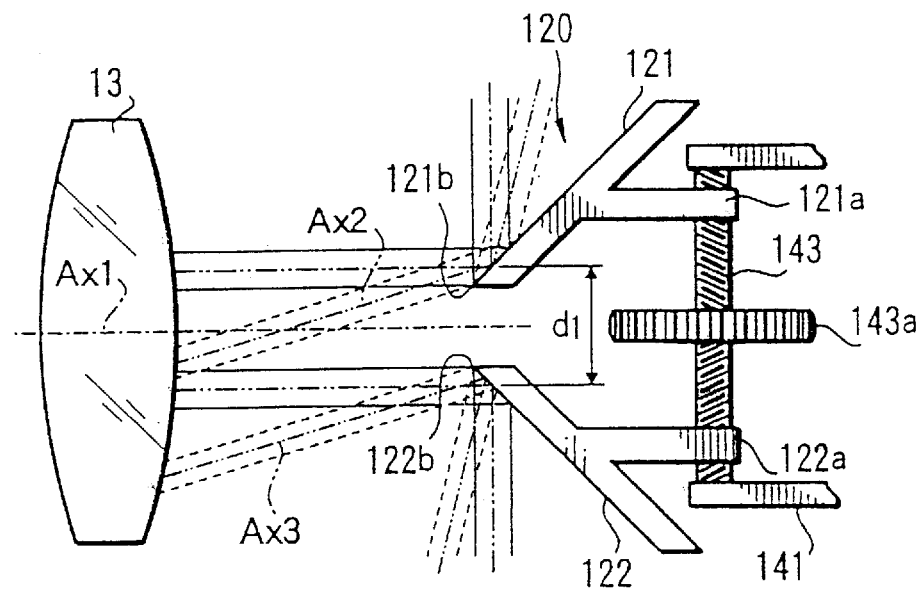
FIG. 28A is a top view of the mirrors of the pupil dividing mechanism showing light paths when the mirrors are positioned furthest apart.
Figure 28B:
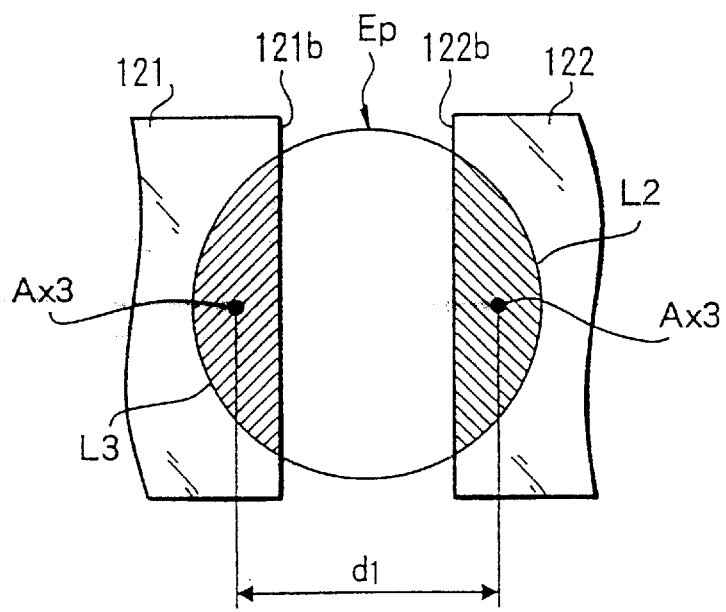
FIG. 28B is a front view from an object side under the condition shown in FIG. 28A.

FIG. 28A is a top view of the mirrors 121 and 122 when the tips 121b and 122b of the mirrors 121 and 122 are farthest apart. FIG. 27B is a front view of the mirrors 121 and 122 when the tips 121b and 122b of the mirrors 121 and 122 are farthest apart. Under this condition, since the distance that the light has traveled is equal to the maximum value d1, the three-dimensional effect on the observed image is large. This is preferable for viewing an object that is located at a point far away from the objective lens 11.

As described above, the twelfth embodiment allows a observer to adjust the three-dimensional effect on the image observed.

Thirteenth Embodiment

Figure 29:
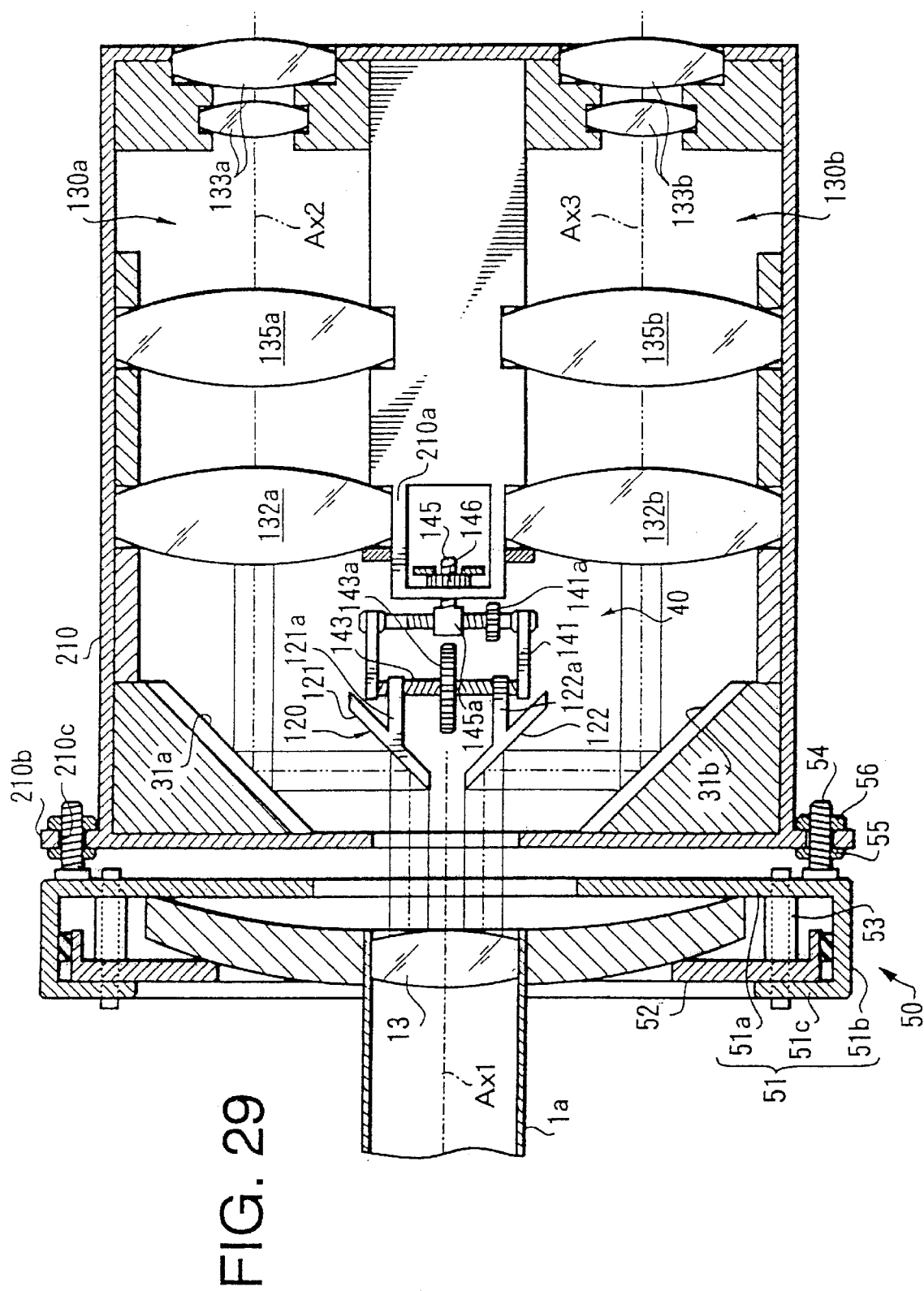
FIG. 29 is a sectional view of an observing portion of a thirteenth embodiment according to the present invention.

FIG. 29 shows a sectional view of the observing portion 210 of a stereoscopic endoscope according to a thirteenth embodiment of the present invention. The observing portion 210 is similar to the observing portion 209 shown in FIG. 25 with the adjustment mechanism 140 attached to a holding wall 210a, and the other common parts having the same reference numerals.

The thirteenth embodiment also includes the insertion portion 1a shown in FIG. 16, and described above for the fifth embodiment. Thus, the insertion portion 1a is attached to the hood 14 and the adapter 50. The adapter 50 is then attached to a flange 210b of the observing portion 210 by passing the adjusting bolts 54 through holes 210c and securing the adjusting bolts 54 with nuts 55 and 56.

Therefore, in the thirteenth embodiment, an insertion portion for a non-stereoscopic endoscope can be used with the observing portion of the stereoscopic endoscope.

Fourteenth Embodiment

Figure 30:
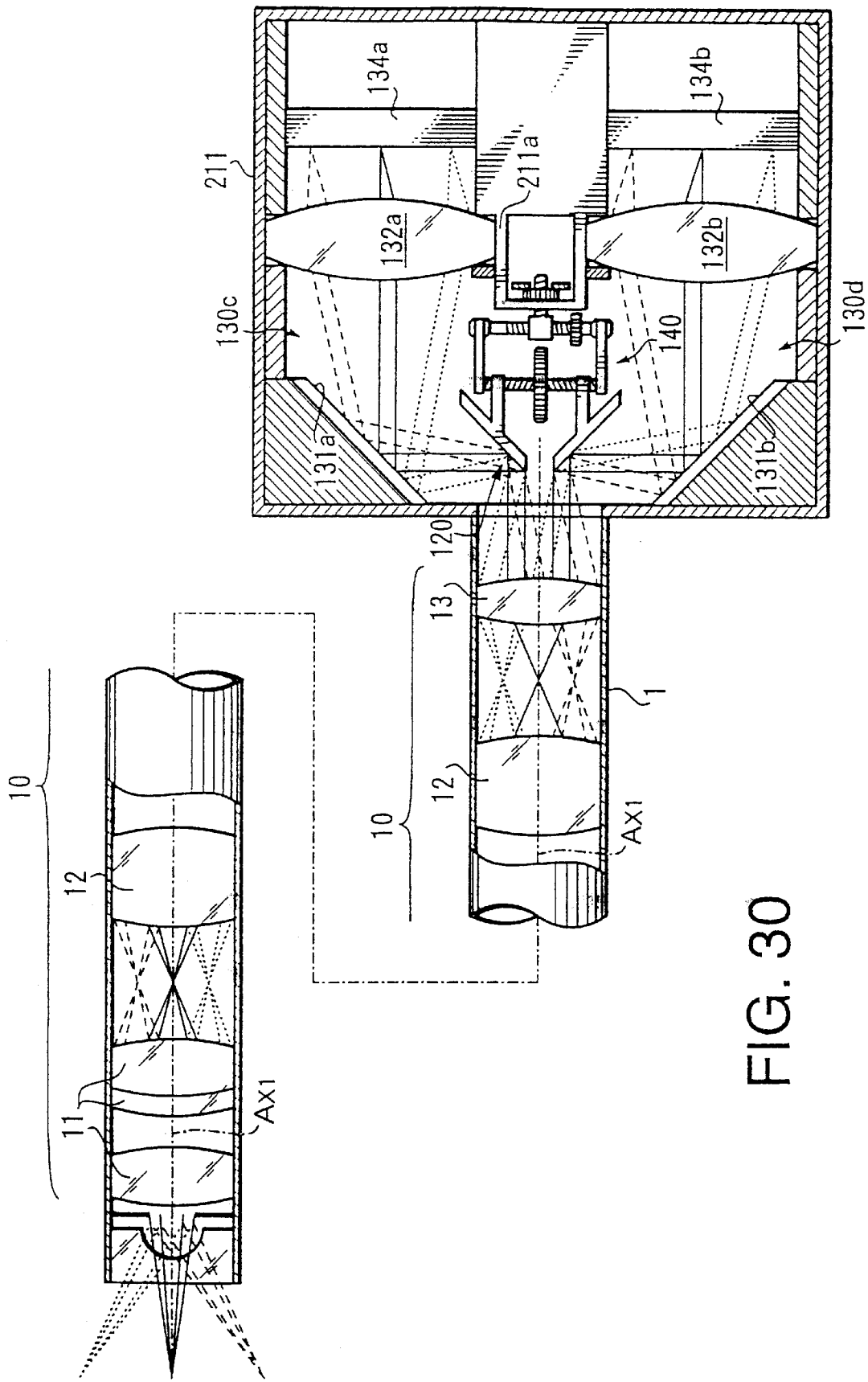
FIG. 30 is a sectional view of a stereoscopic endoscope according to a fourteenth embodiment of the present invention.

FIG. 30 shows a sectional view of a stereoscopic endoscope according to a fourteenth embodiment of the present invention. An observing portion 211 of the fourteenth embodiment includes the pupil dividing mechanism 120 and the adjustment mechanism 140 which is attached to a holding wall 211a. However, the observing portion 211 has a first secondary optical system 130c and a second secondary optical system 130d. The first and second secondary optical systems 130c and 130d are similar to the optical systems 130a and 130b described above, except that the imaging devices 134a and 134b replace the imaging lenses 135a, 135b and eyepiece lenses 133a and 133b, respectively.

Therefore, the imaging devices 134a and 134b output an image signal representative of the right and left images, respectively. The output image can be processed by the processing device 100 and viewed using the monitor 190 and the pair of glasses 191, as described for the first embodiment.

Further, the processing device 100 can also be used to determine a direction and amount of movement of the pupil dividing mechanism 120 in order to improve the three-dimensional effect, in a similar manner to the process described for the movement of the mirror block 20 in the fourth embodiment.

Fifteenth Embodiment

Figure 31:
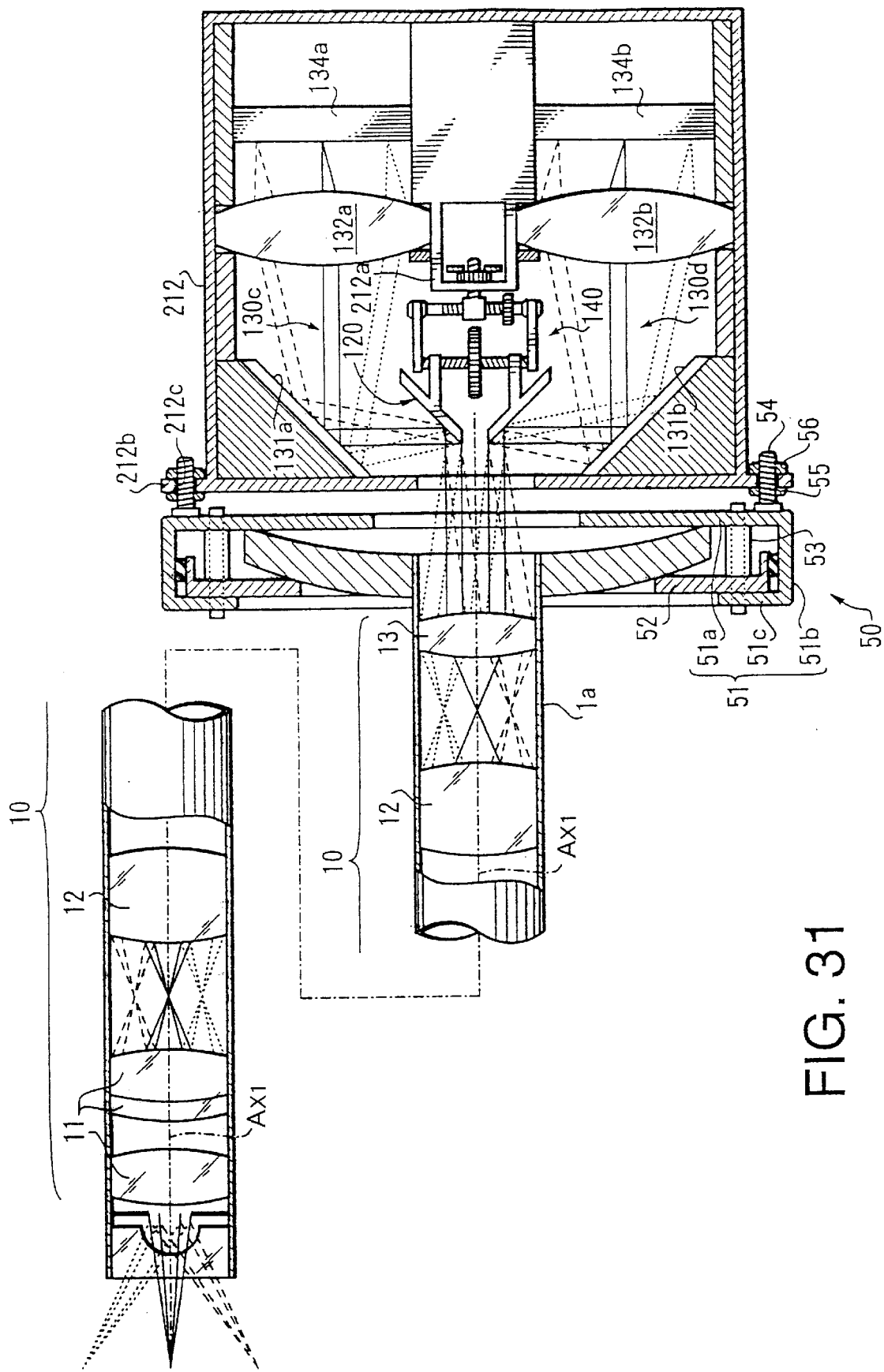
FIG. 31 is a sectional view of a stereoscopic endoscope according to a fifteenth embodiment of the present invention.

FIG. 31 shows a sectional view of a stereoscopic endoscope according to a fifteenth embodiment of the present invention. The fifteenth embodiment includes an observing portion 212 and the insertion portion 1a. The observing portion 212 is similar to the observing portion 211 of the fourteenth embodiment with the adjustment mechanism 140 being attached to a holding wall 212a, and the other common parts having the same reference numerals.

Thus, the insertion portion 1a is attached to the hood 14 and the adapter 50. The adapter 50 is then attached to a flange 212b of the observing portion 212 by passing the adjusting bolts 54 through holes 212c and securing the adjusting bolts 54 with nuts 55 and 56, in a similar manner to that described in the fifth embodiment, and shown in FIG. 16.

Therefore, in the fifteenth embodiment, an insertion portion for a non-stereoscopic endoscope can be used with the observing portion of the stereoscopic endoscope.

Sixteenth Embodiment

Figure 32:
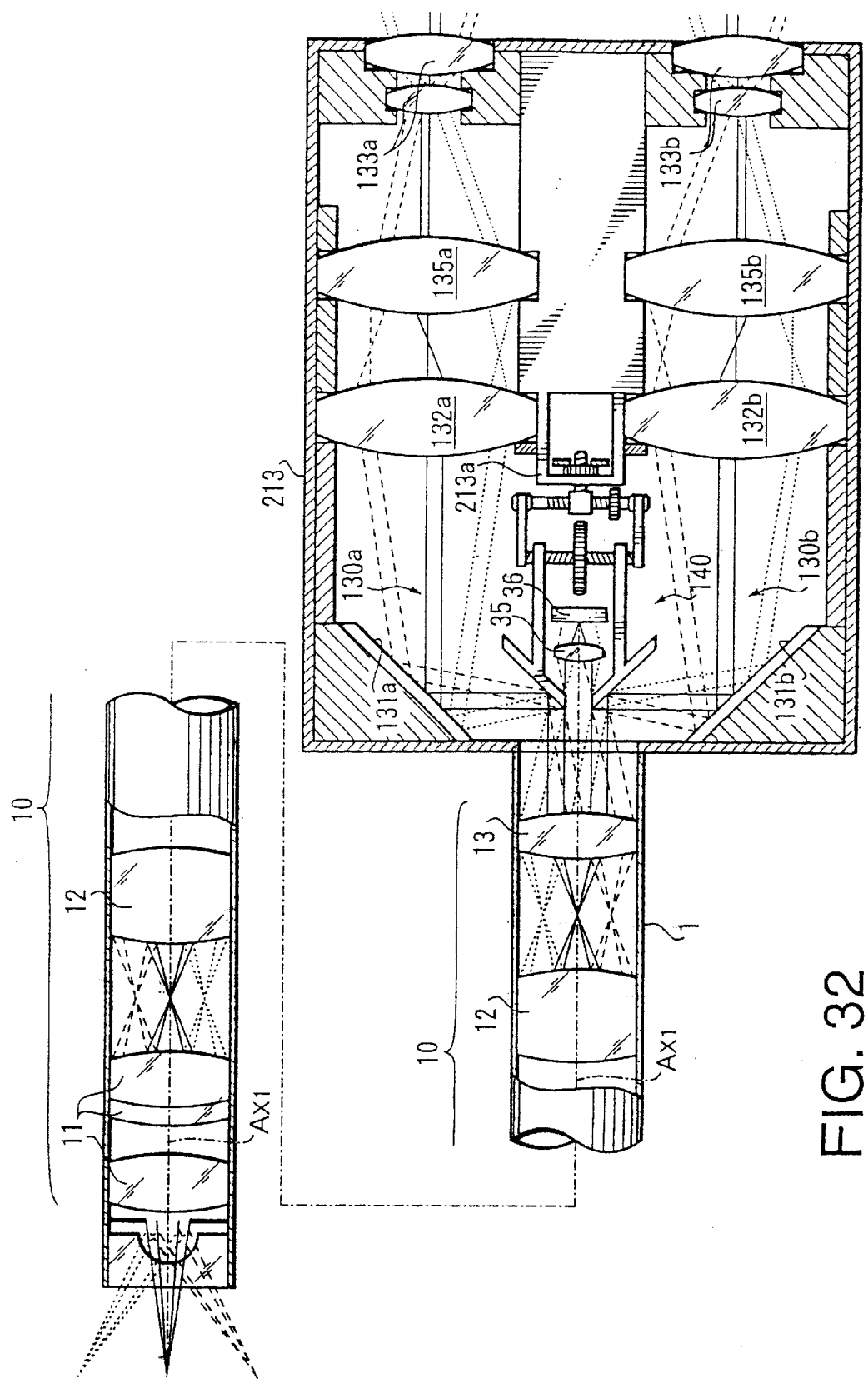
FIG. 32 is a sectional view of a stereoscopic endoscope according to a sixteenth embodiment of the present invention.

FIG. 32 shows a sectional view of a stereoscopic endoscope according to a sixteenth embodiment of the present invention. The sixteenth embodiment includes the insertion portion 1 and an observing portion 213. The observing portion 213 is similar to the observing portion 209 of the twelfth embodiment with the adjustment mechanism 140 being attached to a holding wall 213a, and the other common parts having the same reference numerals.

However, in the sixteenth embodiment, an imaging lens 35 and an imaging device 36 (such as a CCD) are located in between the mirrors 121 and 122. Therefore, when the mirrors 121 and 122 are separated, a portion of the light transmitted through the primary optical system 10 will be incident on the imaging lens 35, and an image will be formed on the imaging device 36. The imaging device 36 outputs an image signal which can be processed by a processing device such as the processing device 100, and shown on the monitor 190. With this construction, a three-dimensional image can be viewed through the eyepiece lenses 133a and 133b. Further, a regular two dimensional image can be viewed on an external monitor.

Seventeenth Embodiment

Figure 33:
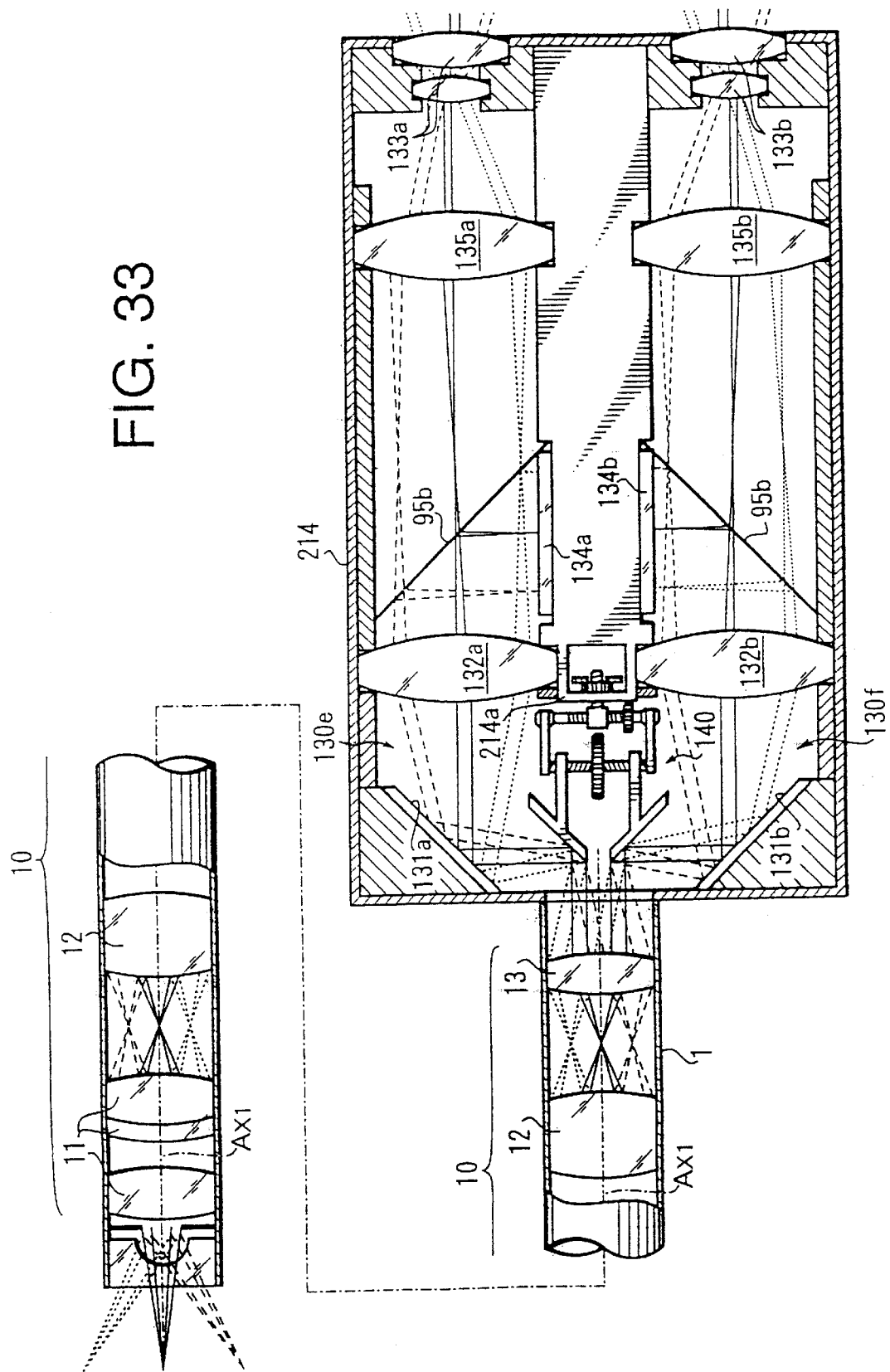
FIG. 33 is a sectional view of a stereoscopic endoscope according to a seventeenth embodiment of the present invention.

FIG. 33 shows a sectional view of a stereoscopic endoscope according to a seventeenth embodiment of the present invention, in which a three-dimensional image can be viewed through the eyepiece lenses as well as displayed on a monitor.

The seventeenth embodiment has an observing portion 214, which is similar to the observing portion 209 of the twelfth embodiment. However, the adjustment mechanism 140 is attached to a holding wall 214a. Further, the observing portion 214 has a first secondary optical system 130e and a second secondary optical system 130f. The first secondary optical system 130e and the second secondary optical system 130f are similar to the first secondary optical system 130c and the second secondary optical system 130d of the previous embodiment, but also include a first half mirror 95a located between the lenses 132a and 135a, and a second half mirror 95b located between the lenses 132b and 135b, as well as a pair of imaging devices 134a and 134b, respectively.

The first half mirror 95a transmits a portion of the light to the eyepiece lens 133a, and transmits the remaining portion of the light to the imaging device 134a. The second half mirror 95b transmits a portion of the light to the eyepiece lens 133b, and transmits the remaining portion of the light to the imaging device 134b. The imaging devices 134a and 134b output left and right image signals to a processing device such as the processing device 100 shown in FIG. 1. Therefore, a three-dimensional image can be observed on the monitor 190 by wearing the pair of glasses 191 of the first embodiment.

Eighteenth Embodiment

Figure 34:
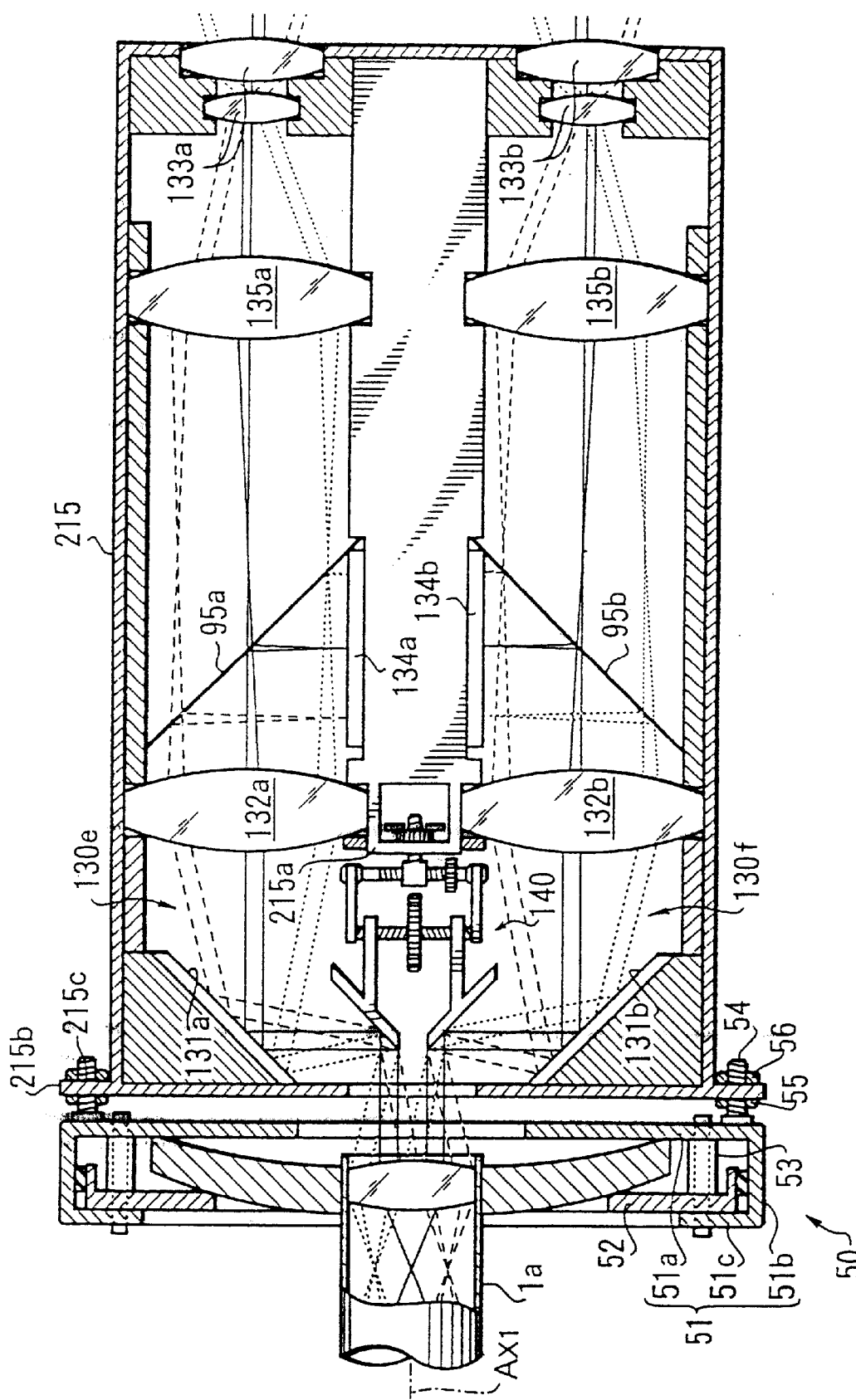
FIG. 34 is a sectional view of a stereoscopic endoscope according to an eighteenth embodiment of the present invention.

FIG. 34 shows a sectional view of a stereoscopic endoscope according to an eighteenth embodiment of the present invention. The eighteenth embodiment includes an observing portion 215 and the insertion portion 1a. The observing portion 215 is similar to the observing portion 214 with the adjustment mechanism 140 being attached to a holding wall 215a, and the other common parts having the same reference numerals.

Thus, the insertion portion 1a is attached to the hood 14 and the adapter 50. The adapter 50 is then attached to a flange 215b of the observing portion 215 by passing the adjusting bolts 54 through holes 215c and securing the adjusting bolts 54 with nuts 55 and 56, in a similar manner to that described in the fifth embodiment, and shown in FIG. 16.

In the twelfth through eighteenth embodiments described above, the adjustment of the pupil dividing mechanism 120 can be automatically done using a combination of motors and image processing in a manner described for the first embodiment. Therefore, a processing device such as the processing device 100 can receive image information either directly through the imaging devices 134a and 134b, or by attaching an imaging device to each of the eyepiece lenses 133a, 133b. Then, the amount and direction of movement required to move the pupil dividing mechanism 120 to its standard correct position can be determined.

Nineteenth Embodiment

FIG. 35 shows a sectional view of a stereoscopic endoscope according to a nineteenth embodiment of the present invention. The nineteenth embodiment includes an observing portion 216 and the insertion portion 1.

Light transmitted from the insertion portion 1 to the observing portion 216 is divided into left and right light beams by a half mirror 396, a mirror 323 and a mirror 324.

One half of the light beam transmitted through the half mirror 396 is reflected by the mirror 323 and transmitted through a first secondary optical system 330a and viewed by an observer. The first secondary optical system 330a includes a mirror 331a, an imaging lenses 332a and an eyepiece lens 333a.

The other half of light beam transmitted through the half mirror 396 is incident on a separator lens 337a that forms the right picture on the imaging device 334a.

Similarly, one half of the light beam reflected by the half mirror 396 is reflected by the mirror 324, and is transmitted through a second secondary optical system 330b and viewed by an observer. The second secondary optical system 330b includes an imaging lenses 332b and an eyepiece lens 333b.

The other half of the beam reflected by the half mirror 396 is incident on a separator lens 337b that forms the left picture on the imaging device 334b.

The imaging devices 334a and 334b output left and right image signals respectively, to a processing device, such as the processing device 100 described above. Alternate left and right images are then displayed on a monitor and viewed wearing special glasses, such as the pair of glasses 191.

Further, the eyepiece lenses 333a and 333b have inverting optics, thereby forming an erect image.

As described above, the stereoscopic endoscope according to the nineteenth embodiment allows direct three-dimensional viewing of the object, as well as three-dimensional viewing using a monitor, and a special pair of glasses. Therefore, many people can view the three-dimensional image simultaneously.

Twentieth Embodiment

Figure 36:
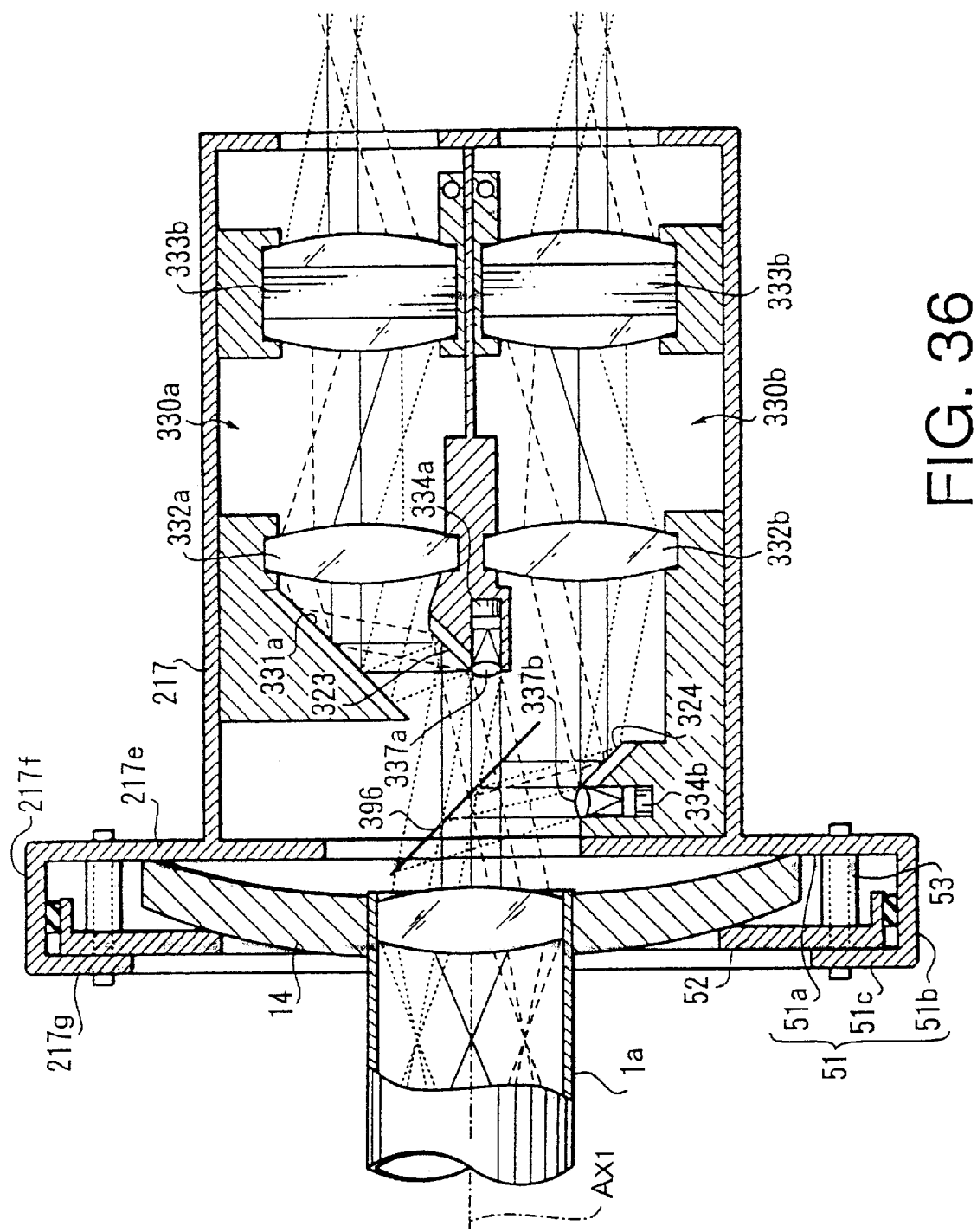
FIG. 36 is a sectional view of a stereoscopic endoscope according to a twentieth embodiment of the present invention.

FIG. 36 shows a sectional view of a stereoscopic endoscope according to a twentieth embodiment of the present invention. The twentieth embodiment includes an observing portion 217 and the insertion portion 1a.

The observing portion 217 is similar to the observing portion 216 described above, with common parts having the same reference numerals. The observing portion 217 has a base flange 217e, a cylindrical portion 217f and a top flange 217g. The base flange 217e has an opening to allow light from the insertion portion 1a to be transmitted to the observing portion 217. The insertion portion 1a is attached to the hood 14 in a similar manner to that described for the fifth embodiment above. The hood 14 is securely fastened between the base flange 217e and the top flange 217g using clamps 52 and bolts 53.

Twenty-first Embodiment

Figure 37:
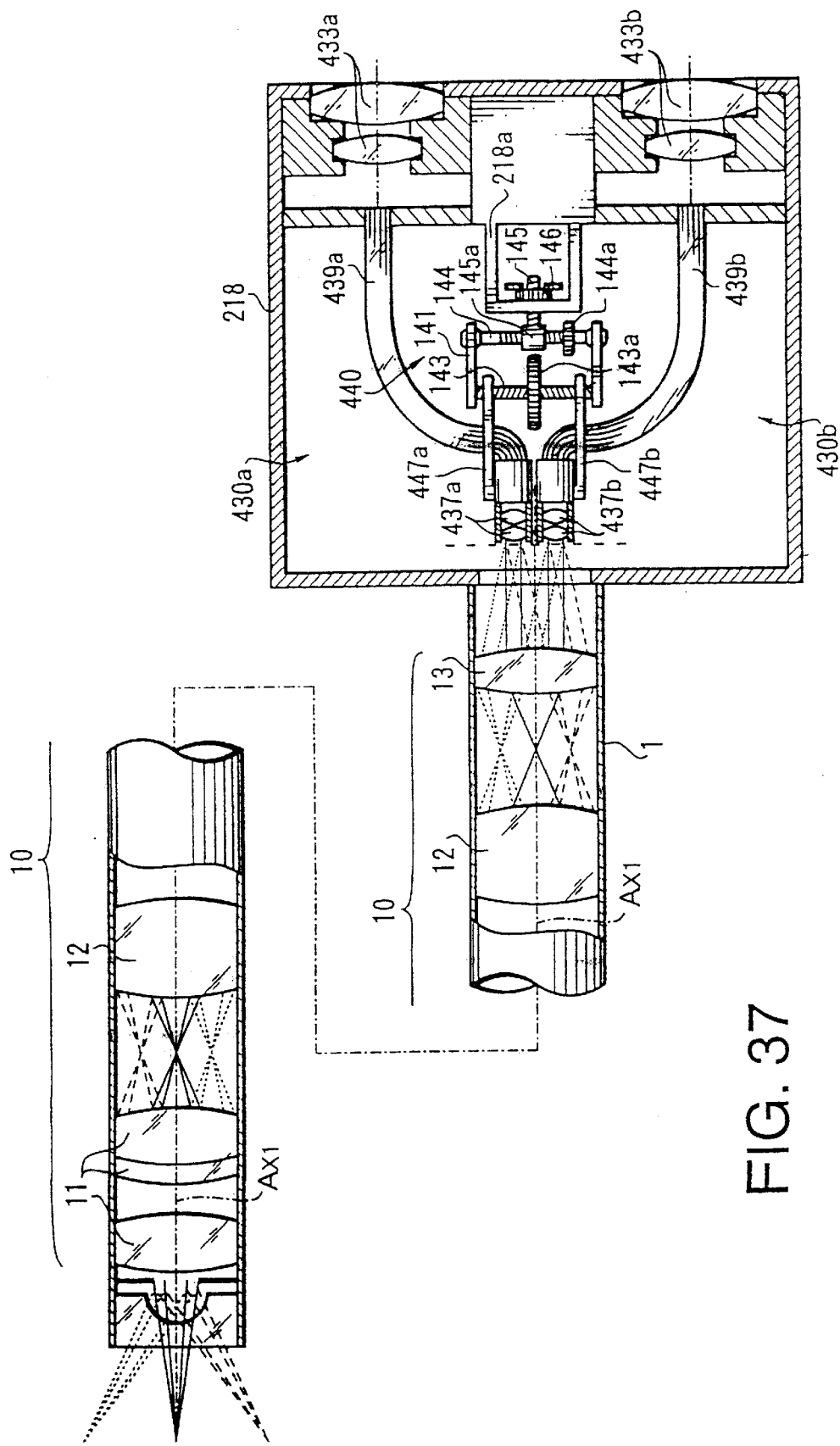
FIG. 37 is a sectional view of a stereoscopic endoscope according to a twenty-first embodiment of the present invention.

FIG. 37 shows a sectional view of a stereoscopic endoscope according to a twenty-first embodiment of the present invention. The twenty-first embodiment includes an observing portion 218 and the insertion portion 1. The observing portion 218 includes a first secondary optical system 430a and a second secondary optical system 430b, and an adjustment mechanism 440. The first secondary optical system 430a has a separator lens 437a, a fiber bundle 439a and an eyepiece lens 433a. Similarly, the second secondary optical system 430b has a separator lens 437b, a fiber bundle 439b and an eyepiece lens 433b.

The separator lenses 437a and 437b are located in the exit pupil Ep (see e.g., FIG. 38A) of the primary optical system 10 and form the left and right picture images at a first end surface of each of the fiber bundles 439a and 439b, respectively. The fiber bundles 439a, 439b transmit the images to a second end surface thereof. The observer can then view the images through the eyepiece lenses 433a and 433b.

The adjustment mechanism 440 is similar to the adjustment mechanism 140 of the twelfth embodiment. Common parts have the same reference numbers and will not be described in detail below.

The adjustment mechanism 440 has a first support 447a and a second support 447b, each having a threaded through-hole. The third adjusting screw 143 is threaded through each of the through holes. The separator lens 437a and the first end portion of the fiber bundle 439a are fixed to the first support 447a, while the separator lens 437b and the first end portion of the fiber bundle 439b are fixed to the second support 447b. The second ends of each of the fiber bundles 439a and 439b are fastened to the observing portion 218.

The third adjusting screw 143 is supported by the holding frame 144 at which the first adjusting screw 144 is fitted. The first adjusting gear 144a is fasten to the first adjusting screw 44 and the second adjusting screw 145 is fitted through holding wall 218a of the observing portion 218. The nut portion 145a formed on the top end of the second adjusting screw 145 is engaged with the first adjusting screw 144. The second adjusting gear 146 that is meshed with the second adjusting screw 145, is installed inside the holding wall 218a.

The third adjusting gear 143a is formed at the center of the third adjusting screw 143. Further, the direction of the threads on the third adjusting screw 143 on one side of the adjusting gear 143 are opposite the direction of the threads on the third adjusting screw 143 formed on the other side adjusting gear 143.

By rotating the first and second adjusting gears 144a and 146, the position of the separator lenses 437a and 437b in the x-axis and the y-axis directions can be changed simultaneously.

The distance between the separator lenses 437a and 437b is adjusted by rotating the third adjusting gear 143a. When the third adjusting gear 143a is rotated in one direction, the lenses 437a and 437b are gradually separated, and by rotating the third adjusting gear 143a in the other direction, the lenses 437a and 437b are moved closer together. The fiber bundles 439a and 439b are flexible, and therefore bend when the first and second supports 447a and 447b are moved.

The change of the distance between the lenses 437a and 437b varies the distance between the viewing fields, and therefore changes the three-dimensional effect of the image.

Figure 38A:
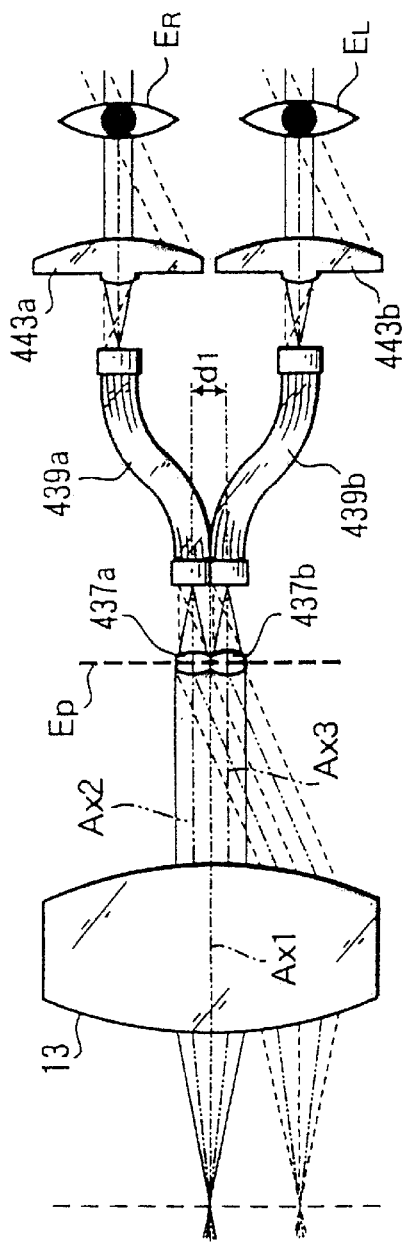
FIG. 38A is a top view of separator lenses of a pupil dividing mechanism of the twenty-first embodiment showing light paths when the separator lenses are positioned closest to each other.

FIG. 38A shows the light path as seen by the right and left eyes $E_R$ and $E_L$, respectively, when the separator lenses 437a and 437b contact each other. Under this condition, since the distance between the lenses 437a and 437b is equal to the minimum value d1, the three-dimensional effect of the view fields is small. This condition is preferable for observing an object that is located at a point near to the objective lens 11.

Figure 38B:
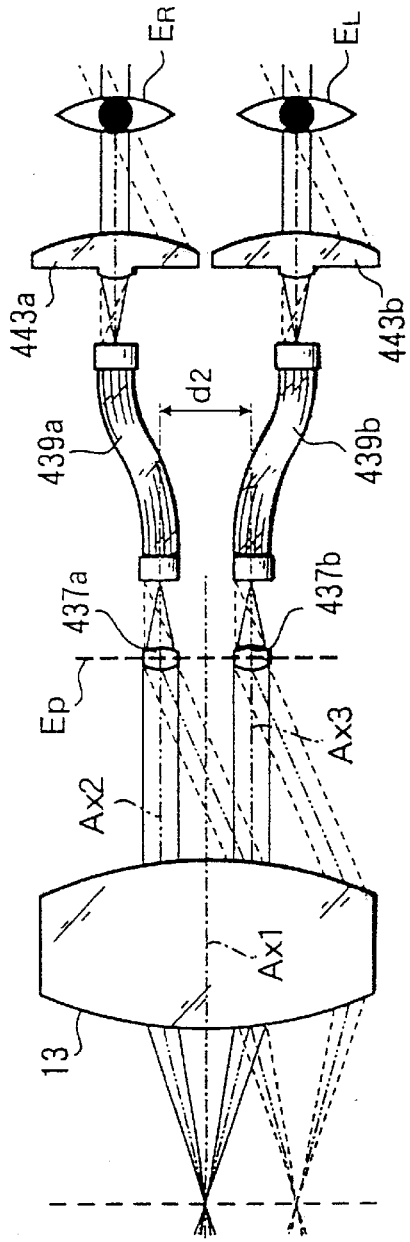
FIG. 38B is a top view of the separator lenses of the pupil dividing mechanism of the twenty-first embodiment showing light paths when the separator lenses are positioned farthest apart.

FIG. 38B shows the light path when the separator lenses 437a and 437b are furthest apart. Under this condition, since the distance between the lenses 437a and 437b is equal to the maximum value d2, the three-dimensional effect of the view fields is large. This condition is preferable for observing an object that is located at a point far away from the objective lens 11.

FIGS. 39A and 39B show one modification to the twenty-first embodiment. In this modification, the separator lenses 437a and 437b are arranged to contact each other. A shading plate 425 is located in the center of the exit pupil and shades the central portion of the light beam that is incident on the separator lenses 437a and 437b.

The incident axes distance between the incident axes is equal to d3 when the shading plate 425 is removed, as shown in FIG. 39A. When the shading plate 425 is present, the distance between the incident axes is equal to d4, as shown in FIG. 39B. In this modification, d4 is larger than d3.

Figure 40A:
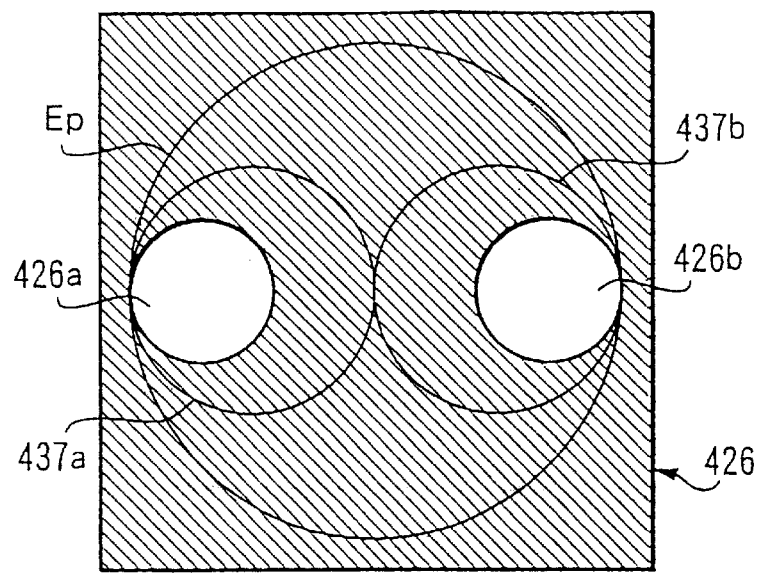
FIG. 40A is a top view of a shading plate used in the pupil dividing mechanism according to the modification of the twenty-first embodiment.
Figure 40B:
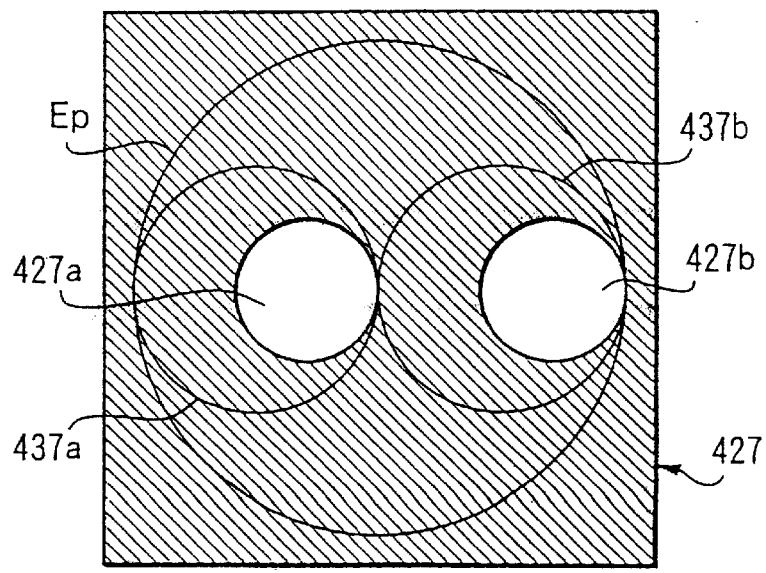
FIG. 40B is a top view of a modification of the shading plate used in the pupil dividing mechanism according to the modification of the twenty-first embodiment.

FIGS. 40A and 40B show two shading plates 426 and 427 which are modifications of the shading plate 425. Each of the shading plates 426 and 427 has apertures that define which areas of the light beams are to be incident on the separator lenses 437a and 437b.

The shading plate 426 in FIG. 40A, has a pair of apertures 426a and 426b that are arranged symmetrically about the optical axis Ax1 of the primary optical system 10, and lie along the exit pupil Ep. The shading plate 427 has a pair of apertures 427a and 427b which are not arranged symmetrically, as shown in FIG. 40B.

As described above by using fiber bundles in the secondary optical systems, the number of parts which require precision positioning such as mirrors, can be reduced.

Twenty-second embodiment

Figure 41:
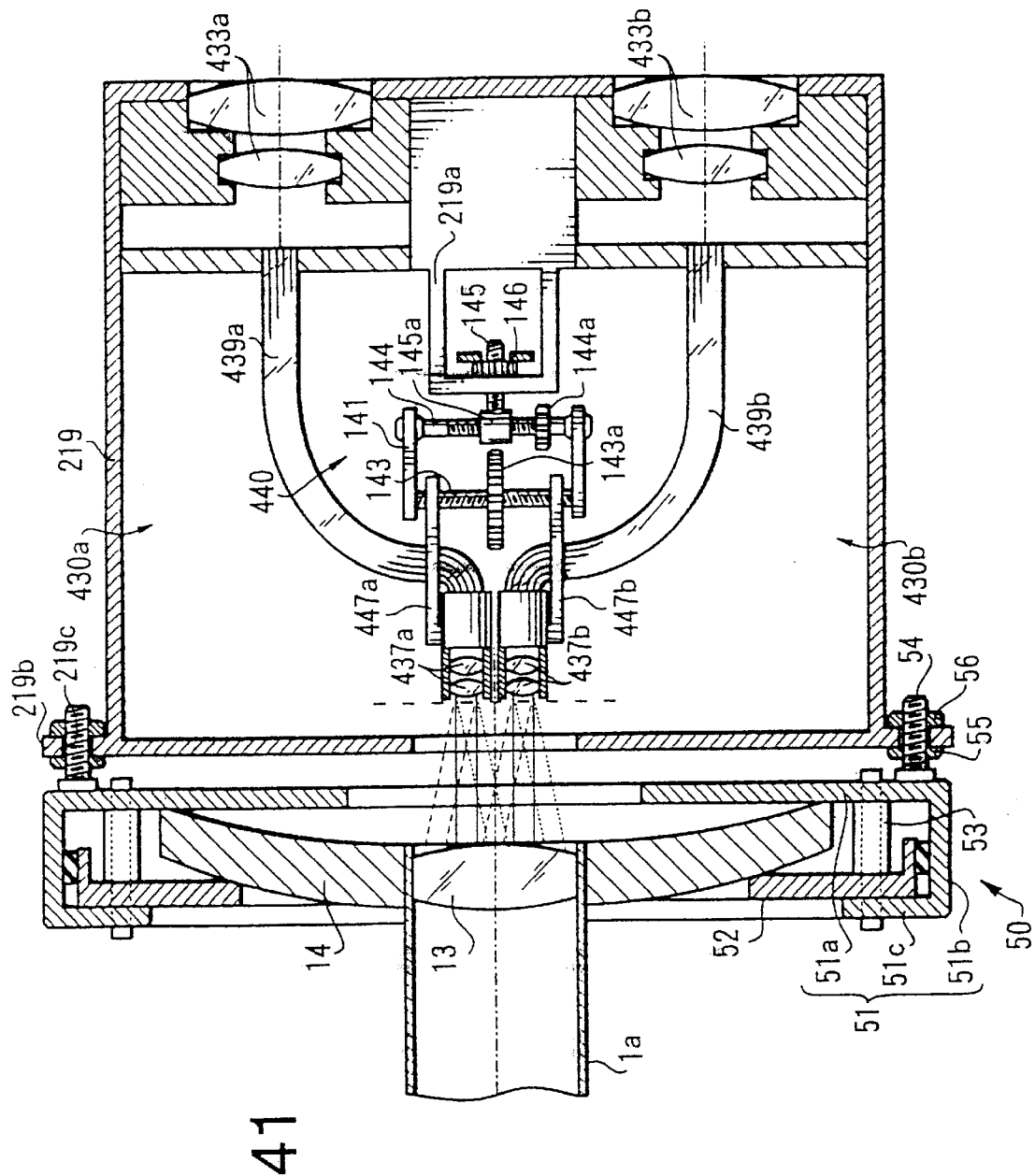
FIG. 41 is a sectional view of a stereoscopic endoscope according to a twenty-second embodiment of the present invention.

FIG. 41 shows a sectional view of a stereoscopic endoscope according to a twenty-second embodiment of the present invention. The twenty-second embodiment has an observing portion 219 and the insertion portion 1a. The observing portion 219 is similar to the observing portion 218 of the twenty-first embodiment described above, with the adjustment mechanism 440 being attached to a holding wall 219a, and the other common parts having the same reference numerals.

Thus, the insertion portion 1a is attached to the hood 14 and the adapter 50. The adapter 50 is then attached to a flange 219b of the observing portion 219 by passing the adjusting bolts 54 through holes 219c and securing the adjusting bolts 54 with nuts 55 and 56, in a similar manner to that described in the fifth embodiment above.

Twenty-third Embodiment

FIG. 42A shows an enlarged portion of an observing portion 220 of a stereoscopic endoscope according to a twenty-third embodiment of the present invention. The observing portion is similar to the observing portion 219 of the twenty-first embodiment, with the common parts having the same reference numerals. Further, the twenty-third embodiment also includes the insertion portion 1, used in the first embodiment.

As shown in FIG. 42A, the observing portion 220 includes an illumination unit 490 used to illuminate an object to be viewed. The illumination unit 490 comprises the light source 491, the condenser lens 492 and the fiber bundles 493A, 493B. The emitted light beam from the illumination unit 490 is transmitted through the exit pupil Ep and insertion unit 1 to be incident on the object to be viewed. The illumination unit 490 is arranged so that the light beam emitted from the light source 491 does not interfere with the light beam that is reflected by the object and incident on the separator lenses 437a and 437b.

FIG. 42B is a front view of the exit pupil observed from the object side, and shows a relationship of illumination light beams L1 and L2, and effective fields E1 and E2 of the separator lenses 437a and 437b, respectively. As shown in FIG. 42B, the illumination light beams L1 and L2 do not interfere with the effective fields E1 and E2 of the separator lenses 437a and 437b.

Twenty-fourth Embodiment

Figure 43:
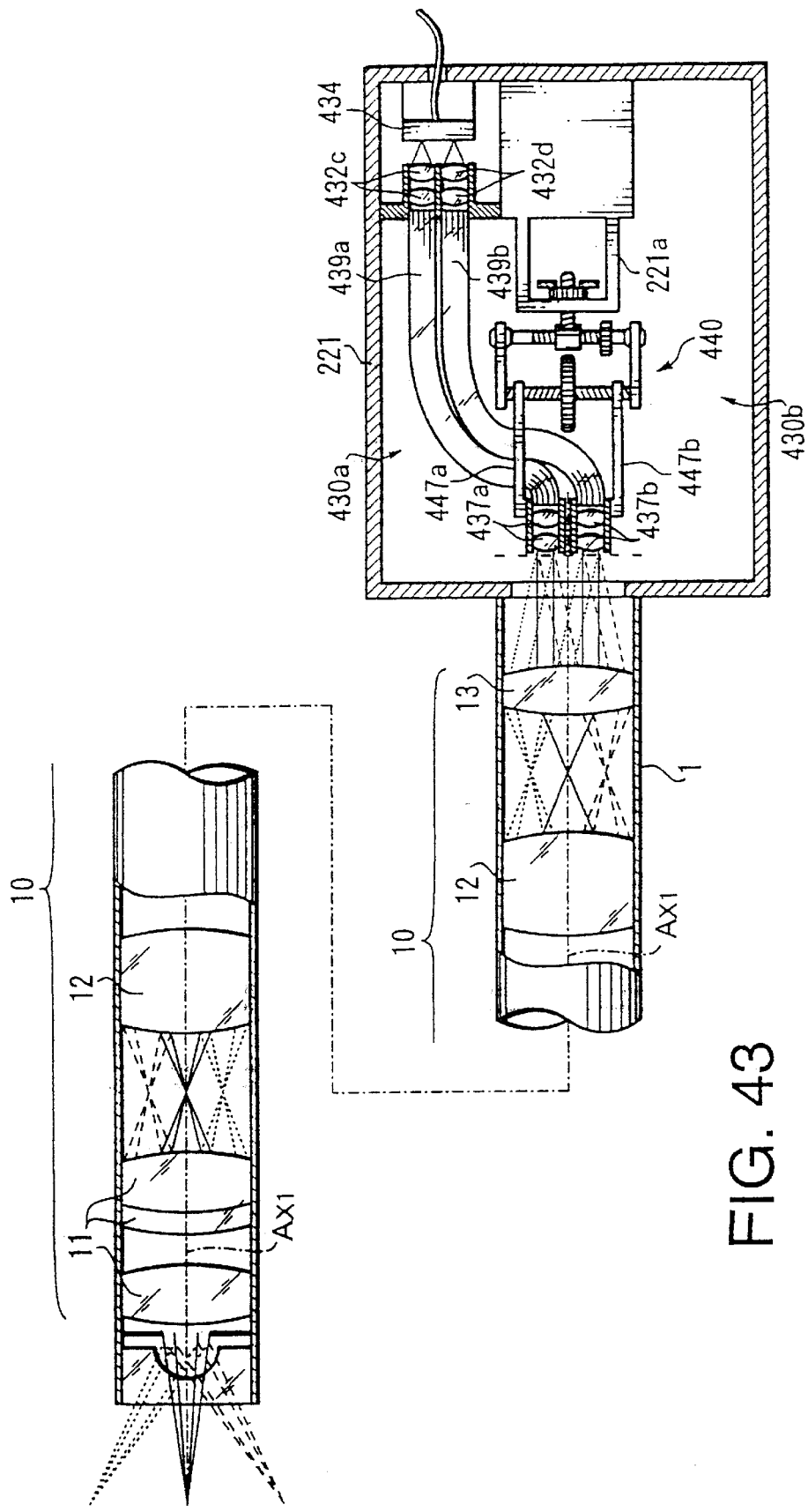
FIG. 43 is a sectional view of a stereoscopic endoscope according to a twenty-fourth embodiment of the present invention.

FIG. 43 shows a sectional view of a stereoscopic endoscope according to a twenty-fourth embodiment of the present invention. The twenty-fourth embodiment has the insertion portion 1 and an observing portion 221. The observing portion 221 is similar to the observing portion 218 of the twenty-first embodiment with the adjustment mechanism 440 being attached to a holding wall 221a, and the other the common parts having the same reference numerals.

The observing portion 221 includes an imaging device 434 instead of the eyepiece lenses 434a and 434b. The images transmitted by the fiber bundles 439a and 439b are formed on the imaging device 434 by the imaging lenses 432c and 432d.

In the twenty-fourth embodiment, the imaging lens 432c forms an image on a first area of the imaging device 434, while the imaging lens 432d forms an image on a second area of the imaging device 434. The first area and second area do not overlap each other.

The output data from the imaging device 434 is input into processing device, such as the processing device 100 of the first embodiment in FIG. 11, that processes the input data to display a three-dimensional picture of the object on the monitor. The output data from the imaging device 434 includes imaging data for both the left and right images. The imaging data is separated into the left and right picture data corresponding to the left and right images formed by each the imaging lens 432c and 432d respectively. The left and right picture data are alternatively displayed on the monitor, and viewed using the pair of glasses 191. This permits the viewing of a three-dimensional image.

Twenty-fifth Embodiment

Figure 44:
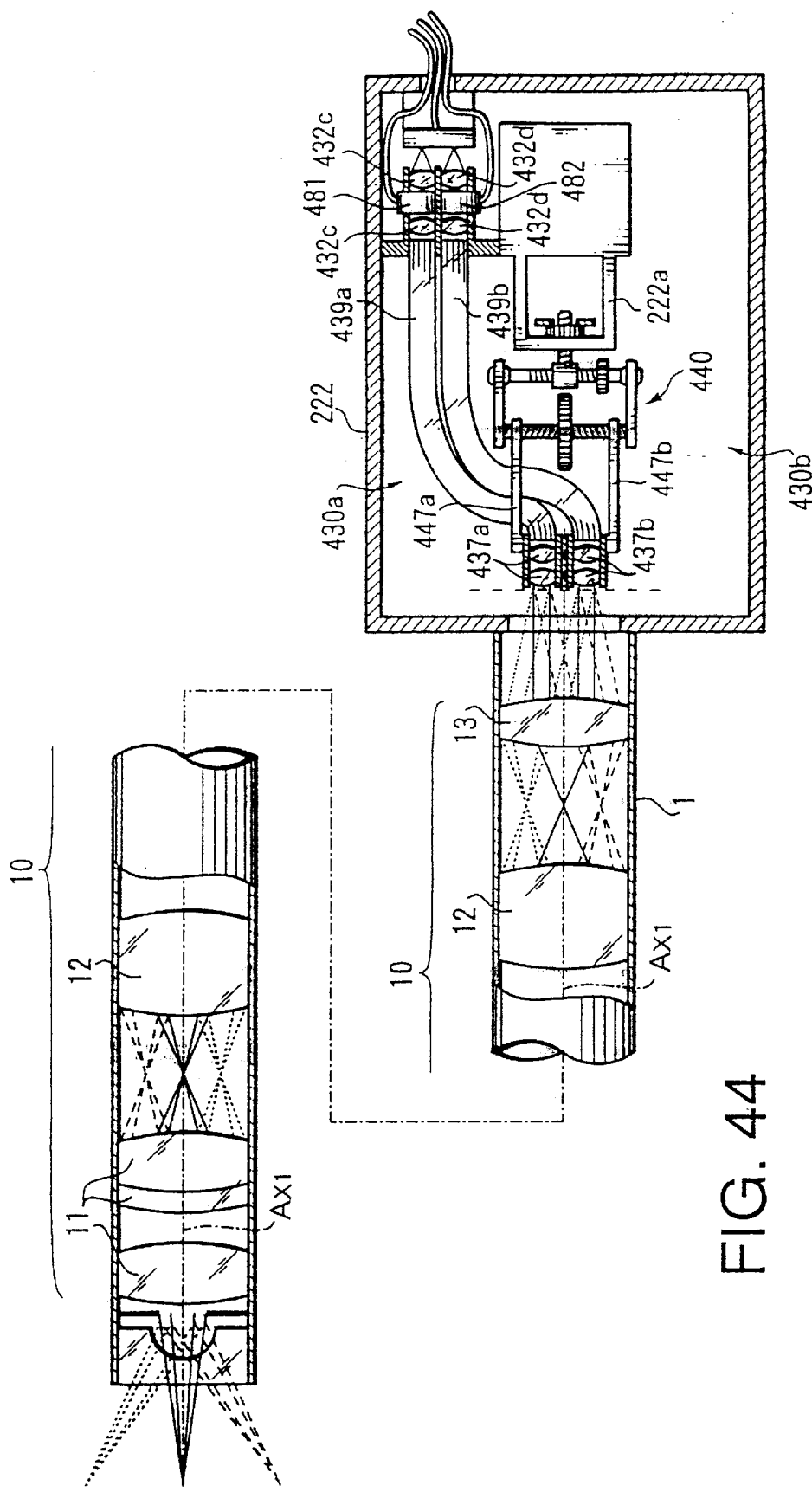
FIG. 44 is a sectional view of a stereoscopic endoscope according to a twenty-fifth embodiment of the present invention.

FIG. 44 shows a sectional view of a stereoscopic endoscope according to a twenty-fifth embodiment of the present invention. The twenty-fifth embodiment has the insertion portion 1 and an observing portion 222. The observing portion 222 is similar to the observing portion 221 of the twenty-fourth embodiment with the adjustment mechanism 440 being attached to a holding wall 222a, and the other the common parts having the same reference numerals.

The observing portion 222 includes a pair of liquid crystal shutters 481 and 482 which are located between the two lenses of each of the imaging lenses 432c and 432d, respectively.

In the twenty-fifth embodiment, the images formed by the imaging lenses 432c and 432d on the imaging device 434 are partially overlapped. Therefore, when the right image is to be formed on the imaging device 434, the left image is blocked by controlling the liquid crystal shutter 482 to be opaque. Similarly, when the left image is to be formed on the imaging device 434, the right image is blocked by controlling the liquid crystal shutter 481 to be opaque. This process results in the imaging device 434 outputting separate left and right image data. The left and right image data can then be processed by a processing device such as the processing device 100 of the first embodiment, and a three dimension image can be viewed on the monitor 190 using the pair of glasses 191.

In the twenty-first, twenty-second, twenty-fourth and twenty-fifth embodiments described above, the positioning of the separator lenses 437a and 437d can be achieved manually. However, by adding two motors, which are similar to the first and second motors of the first embodiment, and a processing device which is similar to the processing device 100, the positioning of the separator lenses 437a and 437d can be done automatically, in a manner similar to that described for the first embodiment. Further, in the twenty-fourth and twenty-fifth embodiments, the use of fiber bundles 439a and 439b and the imaging device 434, can reduce the overall size and number of parts required to manufacture the stereoscopic endoscope. Furthermore, the reduced number of parts can improve the accuracy of the imaging provided by the stereoscopic endoscope.

Twenty-sixth Embodiment

Figure 45:
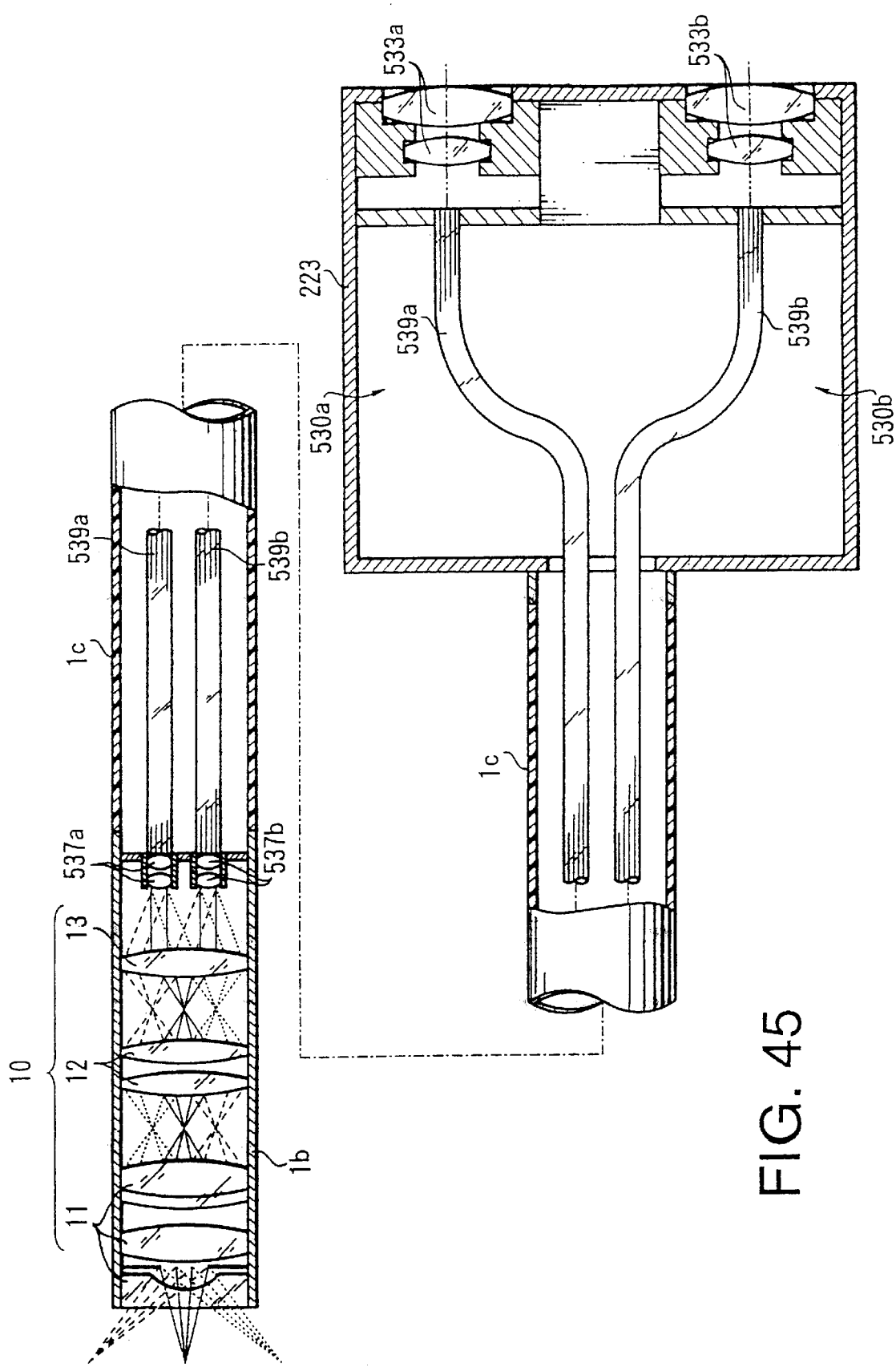
FIG. 45 is a sectional view of a stereoscopic endoscope according to a twenty-sixth embodiment of the present invention.

FIG. 45 shows a sectional view of a stereoscopic endoscope according to a twenty-sixth embodiment of the present invention. The twenty-sixth embodiment includes an insertion portion 1b, an extension portion 1c, and an observing portion 223. The extension portion 1c is flexible and provides a physical and optical connection between the insertion portion 1b and the observing portion 223.

The insertion portion 1b is similar to the insertion portion 1 of the first embodiment. The common parts have the same reference numerals. However, separator lenses 537a and 537b are mounted in the insertion portion 1b at the location of the exit pupil.

The observing portion 223 has a first secondary optical system 530a and a second secondary optical system 530b. The first secondary optical system 530a includes a fiber bundle 539a and an eyepiece lens 533a. The second secondary optical system 530a includes a fiber bundle 539b and an eyepiece lens 533b. A first end of each of the fiber bundles 539a and 539b, that are located inside the observing portion 226, is held in a fixed position. The fiber bundles 539a and 539b extend through the extension portion 1c, and into the insertion portion 1b. A second end of each of the fiber bundles 539a and 539b, located in the insertion portion 1b, is also held in a fixed position. The second ends of the fiber bundles 539a and 539b contact the separator lenses 537a and 537b, respectively, such that the image formed by the separator lenses 537a and 537b is transmitted through the fiber bundles 539a and 539b and viewed through the eyepiece lenses 533a and 533b.

As described above, since the extension portion 1c is flexible, it is possible to observe an object through a narrower opening, than is possible using only a rigid insertion portion.

Twenty-seventh Embodiment

Figure 46:
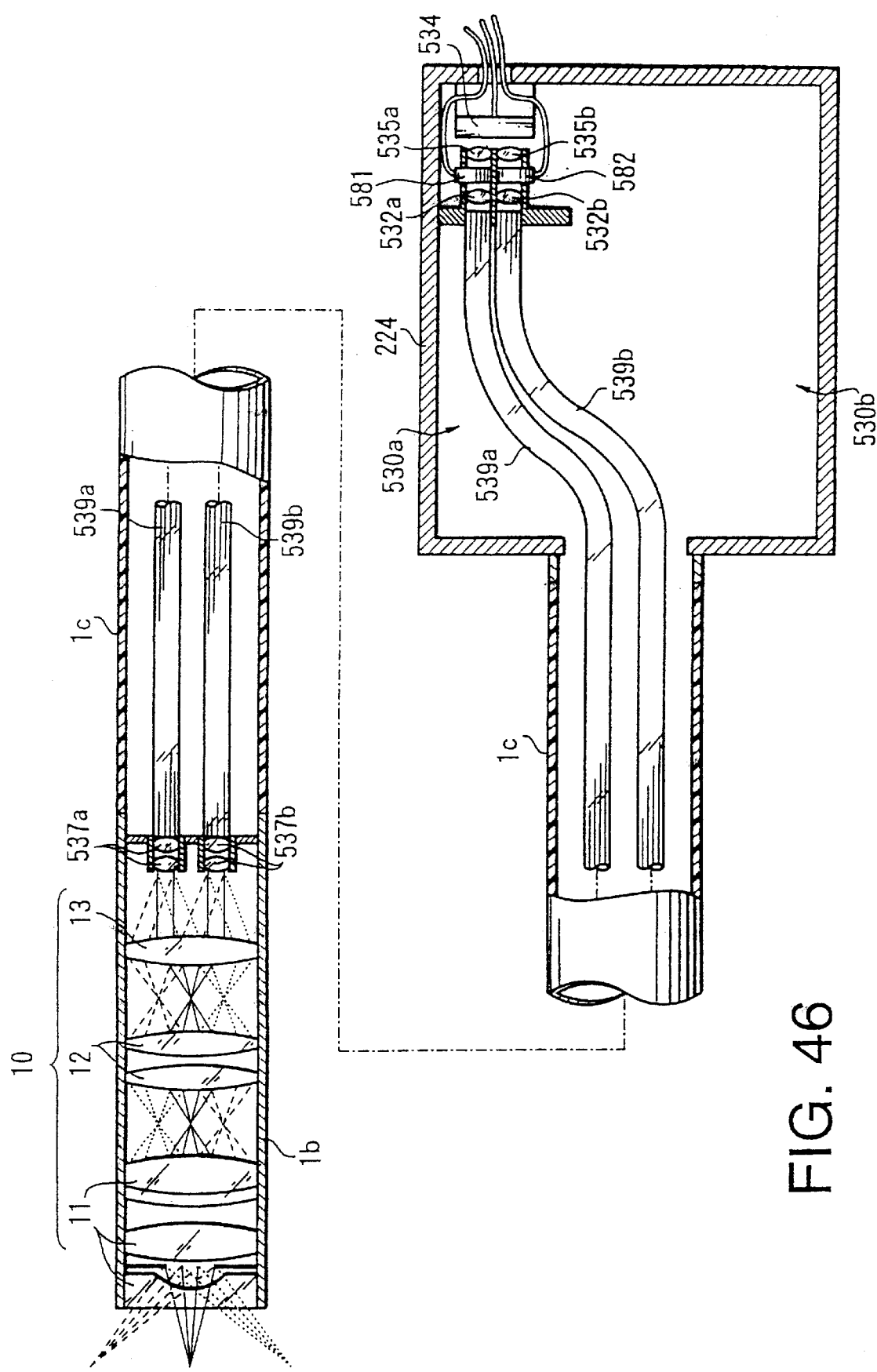
FIG. 46 is a sectional view of a stereoscopic endoscope according to a twenty-seventh embodiment of the present invention.

FIG. 46 shows a sectional view of a stereoscopic endoscope according to a twenty-seventh embodiment of the present invention. The twenty-seventh embodiment includes the insertion portion 1b, the extension portion 1c and an observing portion 224.

The observing portion 224 is similar to the observing portion 223 described above. However, the eyepiece lens 533a is replaced with imaging lenses 532a and 535a, and a first liquid crystal shutter 581, and the eyepiece lens 533b is replaced with imaging lenses 532b and 535b, and a second liquid crystal shutter 582. Further, images formed by the imaging lenses 532a, 535a, 532b and 535b are detected by an imaging device 534.

In the twenty-seventh embodiment, the image formed by the imaging lenses 532a, 535a and the image formed by the imaging lenses 532b, 535b on the image sensing element 534 are partially overlapped.

Therefore, when the right image is to be formed on the imaging device 534, the left image is blocked by controlling the second liquid crystal shutter 582 to be opaque. Similarly, when the left image is to be formed on the imaging device 534, the right image is blocked by controlling the first liquid crystal shutter 581 to be opaque. This process results in the imaging device 534 outputting separate left and right image data. The left and right image data can then be processed by a processing device such as the processing device 100 of the first embodiment, and a three-dimensional image can be viewed on the monitor 190 using the pair of glasses 191.

Twenty-eighth embodiment

Figure 47:
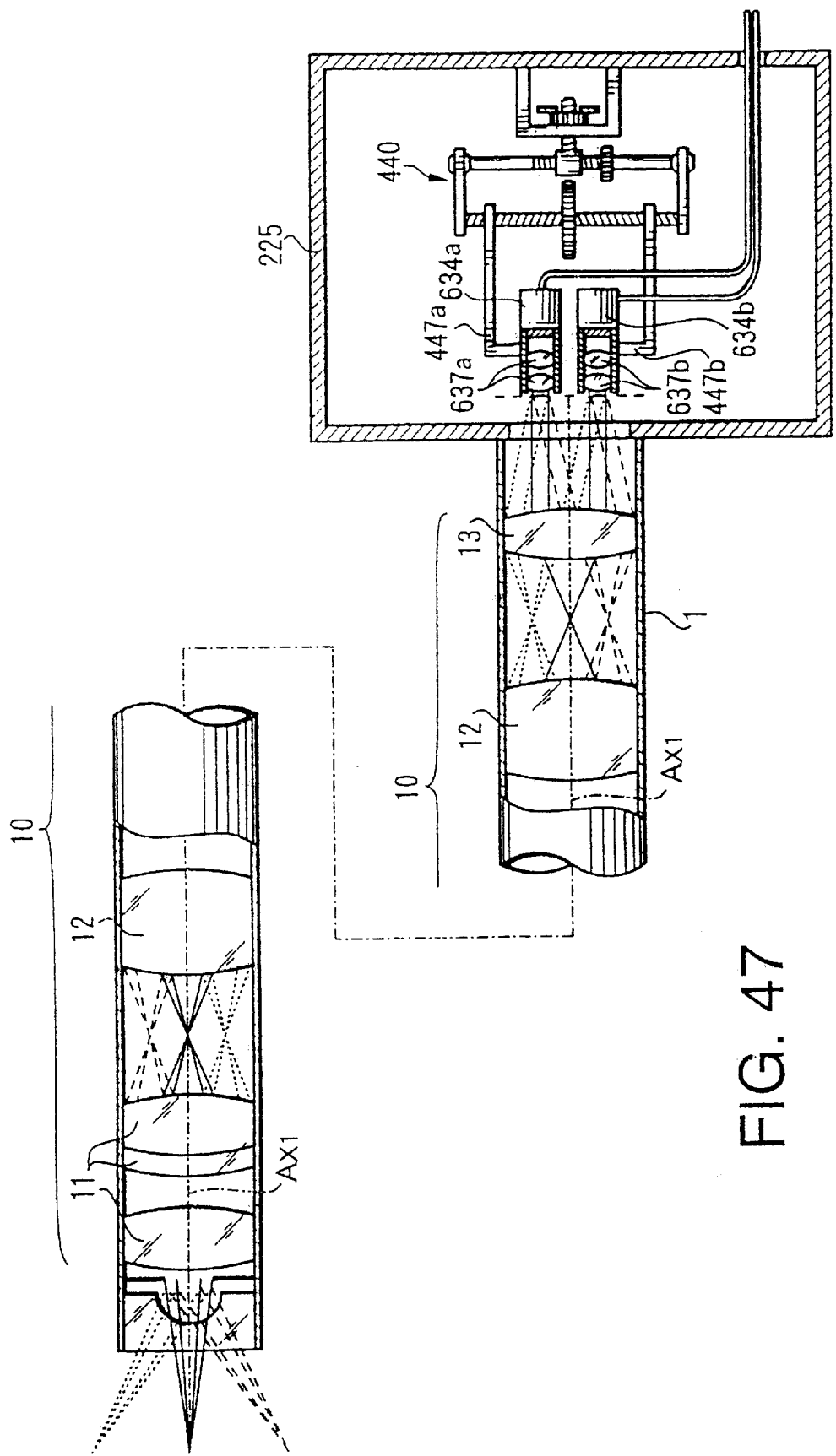
FIG. 47 is a sectional view of a stereoscopic endoscope according to a twenty-eighth embodiment of the present invention.

FIG. 47 shows a sectional view of a stereoscopic endoscope according to a twenty-eighth embodiment of the present invention. The twenty-eighth embodiment has the insertion portion 1a and an observing portion 225. The observing portion 225 includes the adjustment mechanism 440, described above in the twenty-first embodiment, separator lenses 637a and 637b, and imaging devices 634a and 634b.

As shown in FIG. 47, the separator lens 637a and the imaging device 634a are mounted on the support 447a. Similarly, the separator lens 637b and the imaging device 634b are mounted on the support 447b. The separator lens 637a receives light from the left side of the insertion portion 1a, while the separator lens 637b receives light from the right side of the insertion portion 1a. Therefore, by rotating the first and second adjusting gears 144a and 146, the position of the separator lenses 637a and 637b in the x-axis and y-axis directions can be changed simultaneously.

The distance between the separator lenses 637a and 637b is adjusted by rotating the third adjusting gear 143a. When the third adjusting gear 143a is rotated in one direction, the lenses 637a and 637b are gradually separated, and by rotating the third adjusting gear 143a in the other direction, the lenses 637a and 637b are moved closer together.

The change of the distance between the lenses 637a and 637b varies the distance between the viewing fields, and therefore changes the three-dimensional effect of the image.

Twenty-ninth Embodiment

Figure 48:
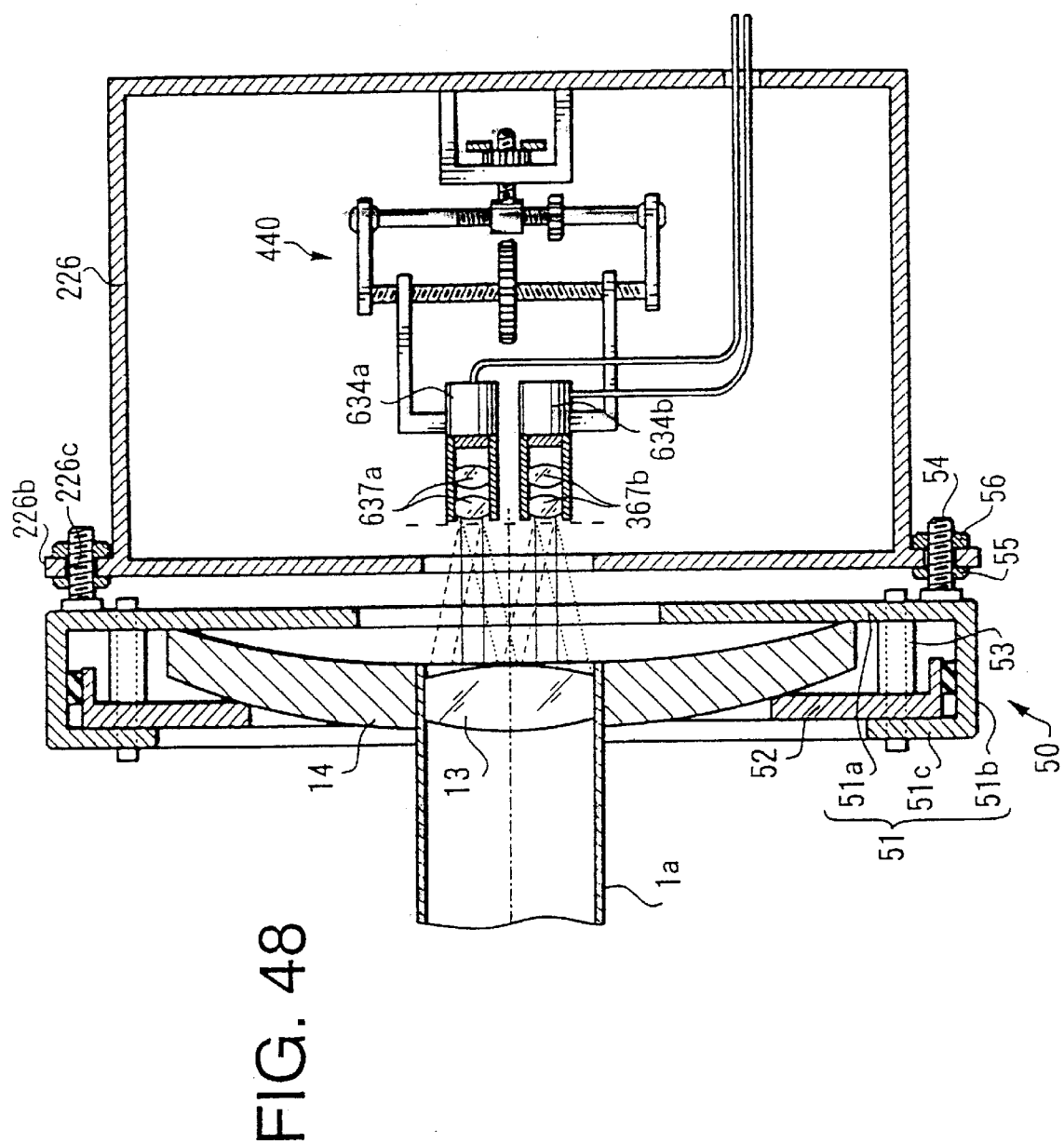
FIG. 48 is a sectional view of an observing portion of a stereoscopic endoscope according to a twenty-ninth embodiment of the present invention.

FIG. 48 shows a sectional view of a stereoscopic endoscope according to a twenty-ninth embodiment of the present invention. The twenty-ninth embodiment has an observing portion 226 and the insertion portion 1a. The observing portion 226 is similar to the observing portion 225 of the twenty-eighth embodiment described above, with common parts having the same reference numerals.

Thus, the insertion portion 1a is attached to the hood 14 and the adapter 50. The adapter 50 is then attached to a flange 226b of the observing portion 226 by passing the adjusting bolts 54 through holes 226c and securing the adjusting bolts 54 with nuts 55 and 56, in a similar manner to that described in the fifth embodiment above.

Thirtieth Embodiment

Figure 49:
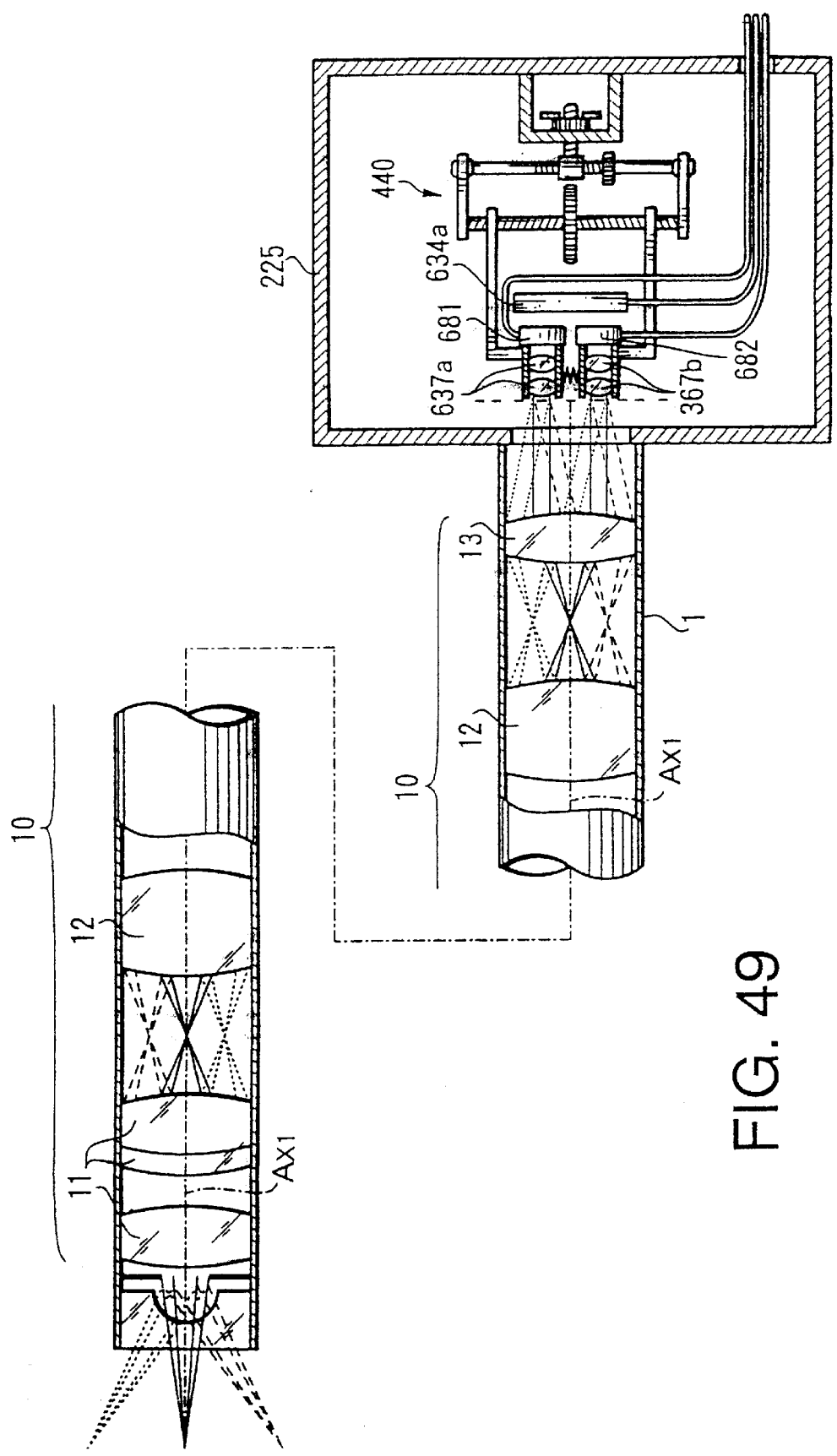
FIG. 49 is a sectional view of a stereoscopic endoscope according to a thirtieth embodiment of the present invention.

FIG. 49 shows a sectional view of a stereoscopic endoscope according to a thirtieth embodiment of the present invention. The thirtieth embodiment has an observing portion 227 and the insertion portion 1. The observing portion 227 is similar to the observing portion 226 of the twenty-ninth embodiment described above, with the common parts having the same reference numerals.

In the observing portion 227, a single imaging device 634a receives the images formed by the separator lenses 637a and 637b. Further, the observing portion 227 includes a pair of liquid crystal shutters 681 and 682 which are located between the each of the separator lenses 637a and 637b, respectively, and the imaging device 634.

In the thirtieth embodiment, the images formed by the separator lenses 637a and 637b on the imaging device 634 may be partially overlapped, in the case that the distance between the incident axes of the left and right images is small. Therefore, when the right image is to be formed on the imaging device 634, the left image is blocked by controlling the liquid crystal shutter 682 to be opaque. Similarly, when the left image is to be formed on the imaging device 634, the right image is blocked by controlling the liquid crystal shutter 681 to be opaque. This process results in the imaging device 634 outputting separate left and right image data. The left and right image data can then be processed by a processing device such as the processing device 100 of the first embodiment, and a three-dimensional image can be viewed on the monitor 190 using the pair of glasses 191.

If the adjustment device 440 increases the distance between the separator lenses 637a and 637b, then the distance between the incident axes of the left and right images is large, and the images formed on the imaging device 634 will not overlap.

Thirty-first Embodiment

Figure 50A:
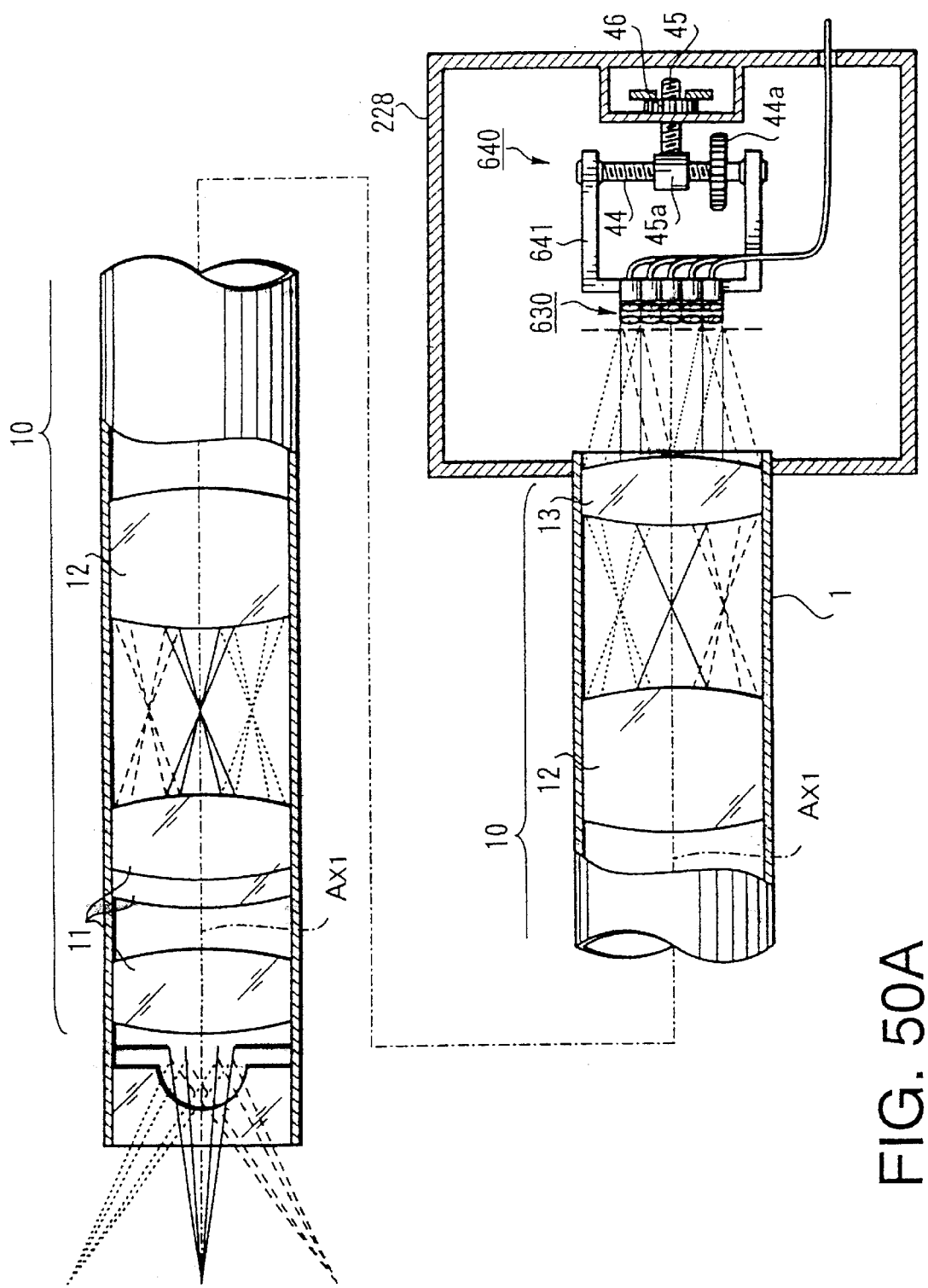
FIG. 50A is a sectional view of a stereoscopic endoscope according to a thirty-first embodiment of the present invention.

FIG. 50A shows a sectional view of a stereoscopic endoscope according to a thirty-first embodiment of the present invention. The thirty-first embodiment includes the insertion portion 1 and an observing portion 228. The observing portion 228 includes a secondary optical system 630 and an adjustment mechanism 640 having a mounting frame 641 which supports the secondary optical system 630. The adjustment mechanism 640 is similar to the adjustment mechanism 40, with the common parts having the same reference numerals.

Figure 50B:
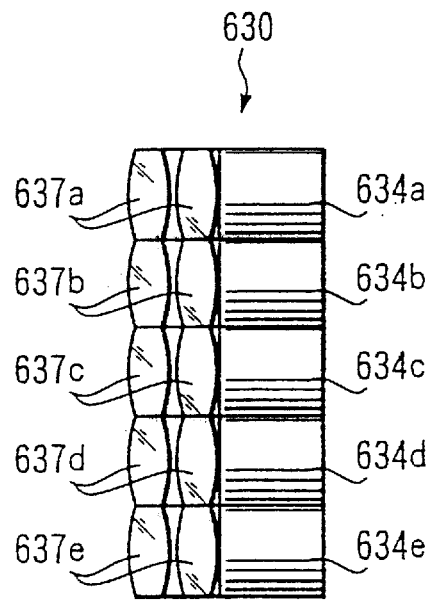
FIG. 50B is an enlarged view of a pupil dividing mechanism of an observing unit of the stereoscopic endoscope shown in FIG. 50A.

The secondary optical system 630 includes five separator lenses 637a, 637b, 637c, 637d, and 637e, and five imaging devices 634a, 634b, 634c, 634d, and 634e, as shown in FIG. 50B. The incident surfaces of the five separator lenses 637a, 637b, 637c, 637d, and 637e are arranged to be coincident with the plane of the exit pupil. However, by rotating the first and second adjusting gears 44a and 46, the position of the secondary optical system 630 in the x-axis and y-axis directions can be changed simultaneously.

Figure 50C:
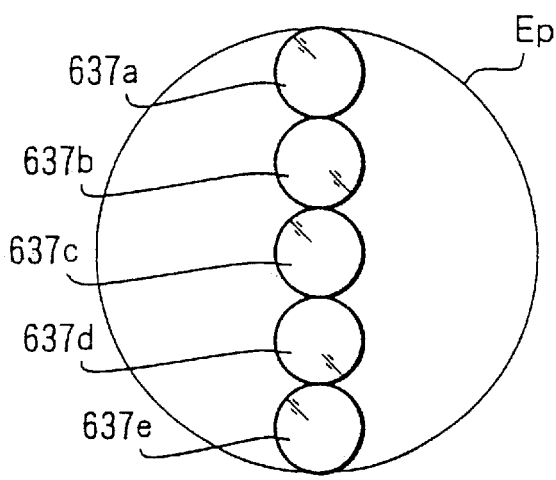
FIG. 50C shows a front view of an arrangement of separator lenses of the pupil dividing mechanism shown in FIG. 50B, with respect to an exit pupil of a primary optical system of the stereoscopic endoscope shown in FIG. 50A.

FIG. 50C shows the view field for each of the five separator lenses 637a through 637e, and their corresponding imaging devices, with respect to the exit pupil Ep. As shown in FIG. 50C, by selecting an appropriate separator lens and its corresponding imaging device, the three-dimensional effect of the image can be varied.

If, for example, the output of the imaging devices 634a and 634e were selected, then the distance between the incident axis of the left image (detected by the imaging device 634a) and the incident axis of the right image (detected by the imaging device 634e) will be a maximum. Therefore, the three-dimensional effect on the image is large. This condition is preferable for observing an object that is located at a point far way from the insertion portion 1.

Conversely, if, for example, the output of the imaging devices 634b and 634d were selected, then the distance between the incident axis of the left image (detected by the imaging device 634b) and the incident axis of the right image (detected by the imaging device 634d) will be a minimum. Therefore, the three-dimensional effect on the image is small. This condition is preferable for observing an object that is located at a point near to the insertion portion 1.

Therefore, a change in the three-dimensional effect can be achieved by selecting the appropriate pair of imaging devices in order to process the output image data. This is accomplished without the need for moving the separator lenses 637a through 637e relative to each other.

Further, by selecting adjacent pairs of imaging devices, the output image data representative of either the left or the right image can be displayed. Thus, in order to display the left image, the imaging devices 634a and 634b should be selected. Similarly, in order to display the right image, the imaging devices 634d and 634e should be selected.

Figure 51:
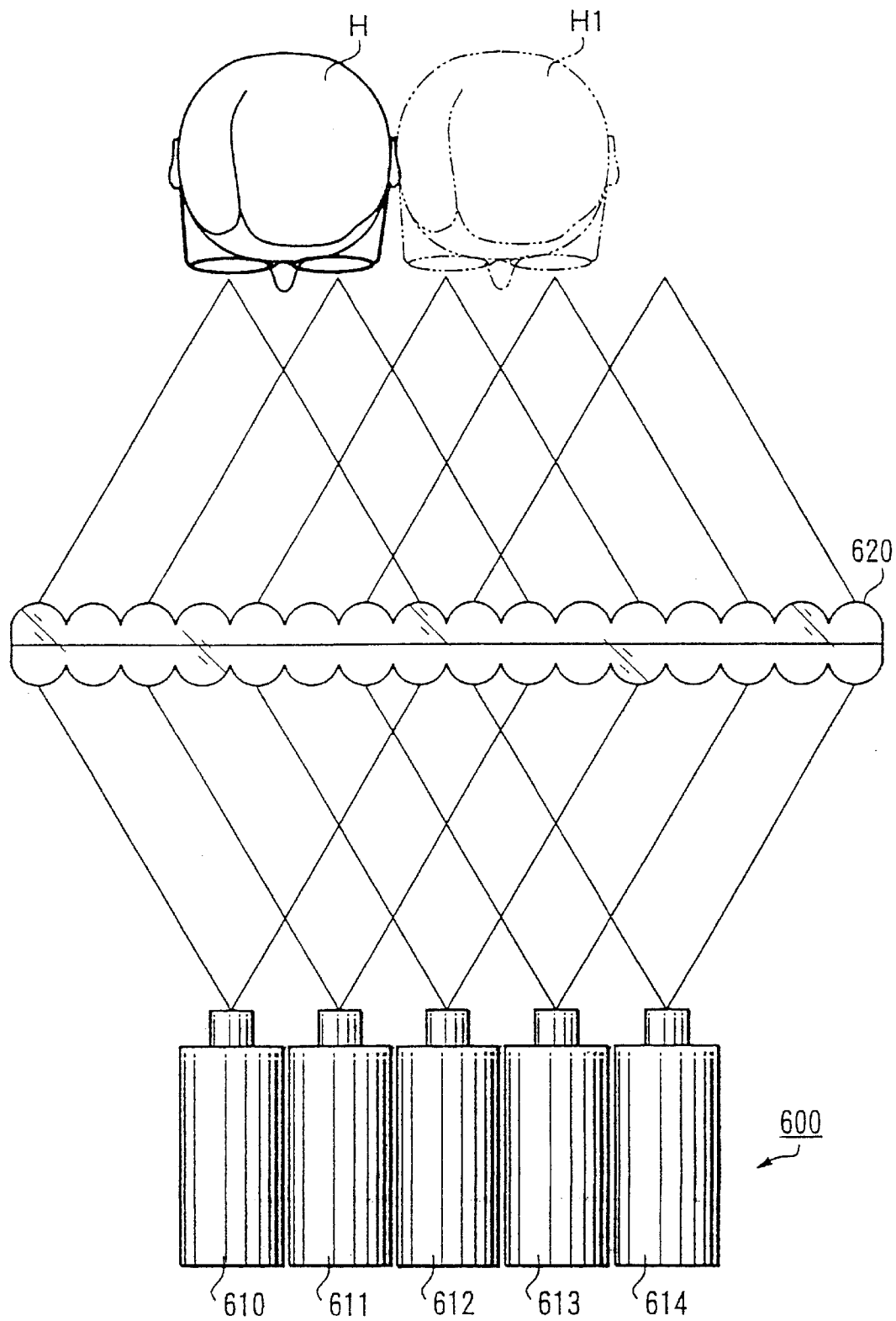
FIG. 51 shows a block diagram of an apparatus that uses a lenticular screen to display three-dimensional images of images viewed using a stereoscopic endoscope.

FIG. 51 shows a projection device 600 used to display a three-dimensional image of the object viewed in the stereoscopic endoscope. The projection device 600 includes a lenticular screen 620 and five projectors 610, 611, 612, 613 and 614 that project light beams toward the rear side of the lenticular screen 620 to form the images taken by the imaging devices 634a, 634b, 634c, 634d and 634e respectively. The projectors are aligned along a horizontal direction Dh.

The lenticular screen 620 is composed of many parallel cylinders having generatrixes which are aligned in the vertical direction (i.e., in a direction out of the drawing). The lenticular screen 620 defines the directions of the light beams transmitted therethrough. The directions of the transmitted light beams depend on the angles of incidence of the light beams projected from the projectors 610 through 614 to the lenticular screen 620.

The light beams from each of the projectors 610 through 614 is projected onto a limited area of the lenticular screen 620. Further, the projected light beams partially overlap each other, in the horizontal direction Dh. As a result, the left and right eyes of the observer looks at the images formed by the different projectors. This forms a three-dimensional image.

Further, the observing direction changes according to a change in the view point of the observer in the horizontal direction Dh. For example, when the head H of the observer is located at the position H1, the right eye sees the image formed primarily by the second projector 611, and the left eye sees the image formed primarily by the third projector 612.

However, when the head H is moved to a position H2, the right eye sees the image formed primarily by the fourth projector 613 and the left eye sees the image formed primarily by the fifth projector 614.

Therefore by moving his head H in the horizontal direction, the observer can change his view point and see a different portion of the image.

Thirty-second Embodiment

Figure 52:
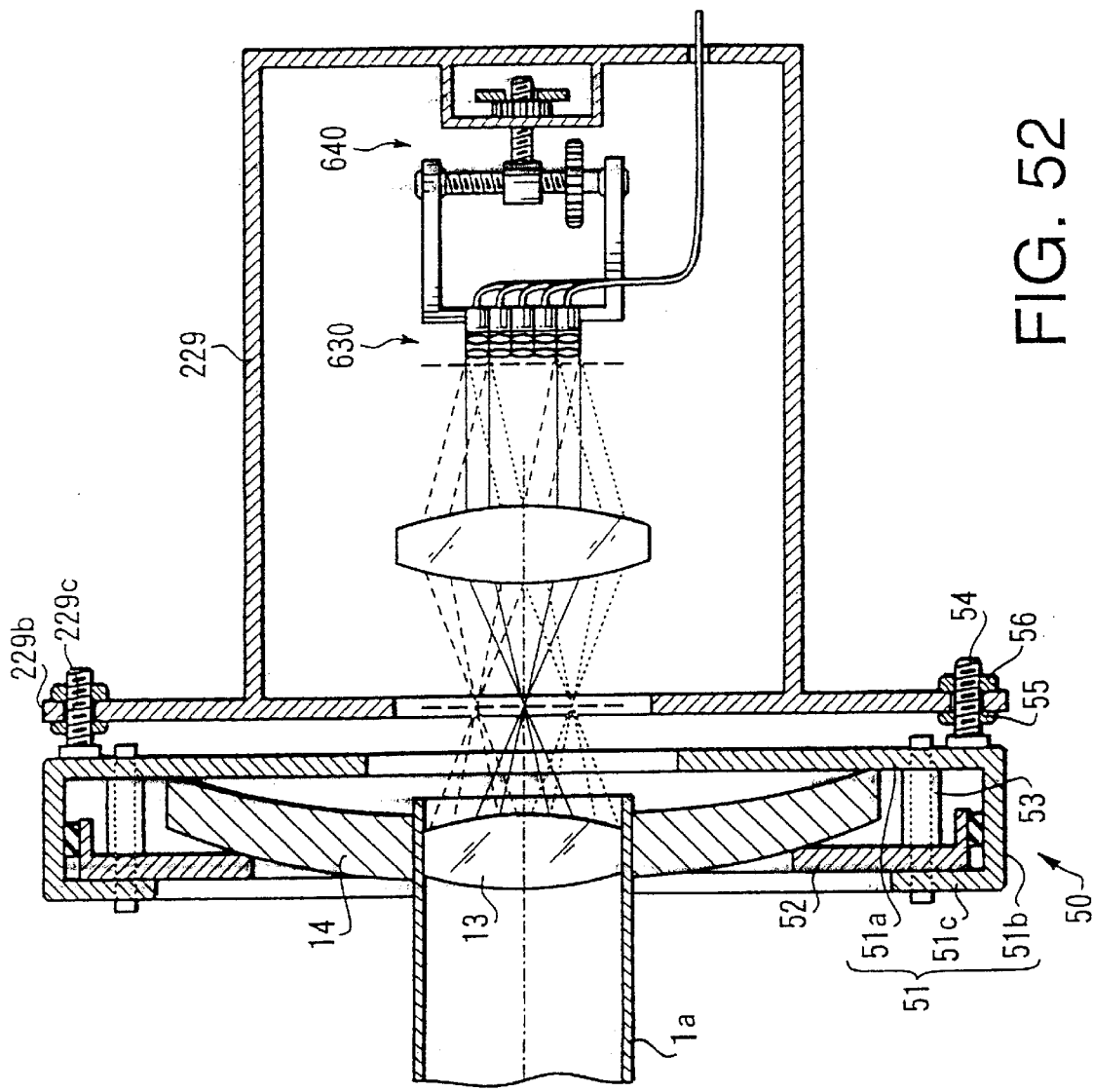
FIG. 52 shows a sectional view of an observing portion of a stereoscopic endoscope according to a thirty-second embodiment of the present invention.

FIG. 52 shows a sectional view of a stereoscopic endoscope according to a thirty-second embodiment of the present invention. The thirty-second embodiment includes the insertion portion 1a and an observing portion 229.

The observing portion 229 is similar to the observing portion 228 described above, with the common parts having the same reference numerals. The observing portion 229 has a base flange 229b. The base flange 229b has an opening to allow light from the insertion portion 1a to be transmitted to the observing portion 229.

Thus, the insertion portion 1a is attached to the hood 14 and the adapter 50. The adapter 50 is then attached to the flange 229b of the observing portion 229 by passing the adjusting bolts 54 through holes 229c and securing the adjusting bolts 54 with nuts 55 and 56, in a similar manner to that described for the fifth embodiment above.

Thirty-third Embodiment

Figure 53:
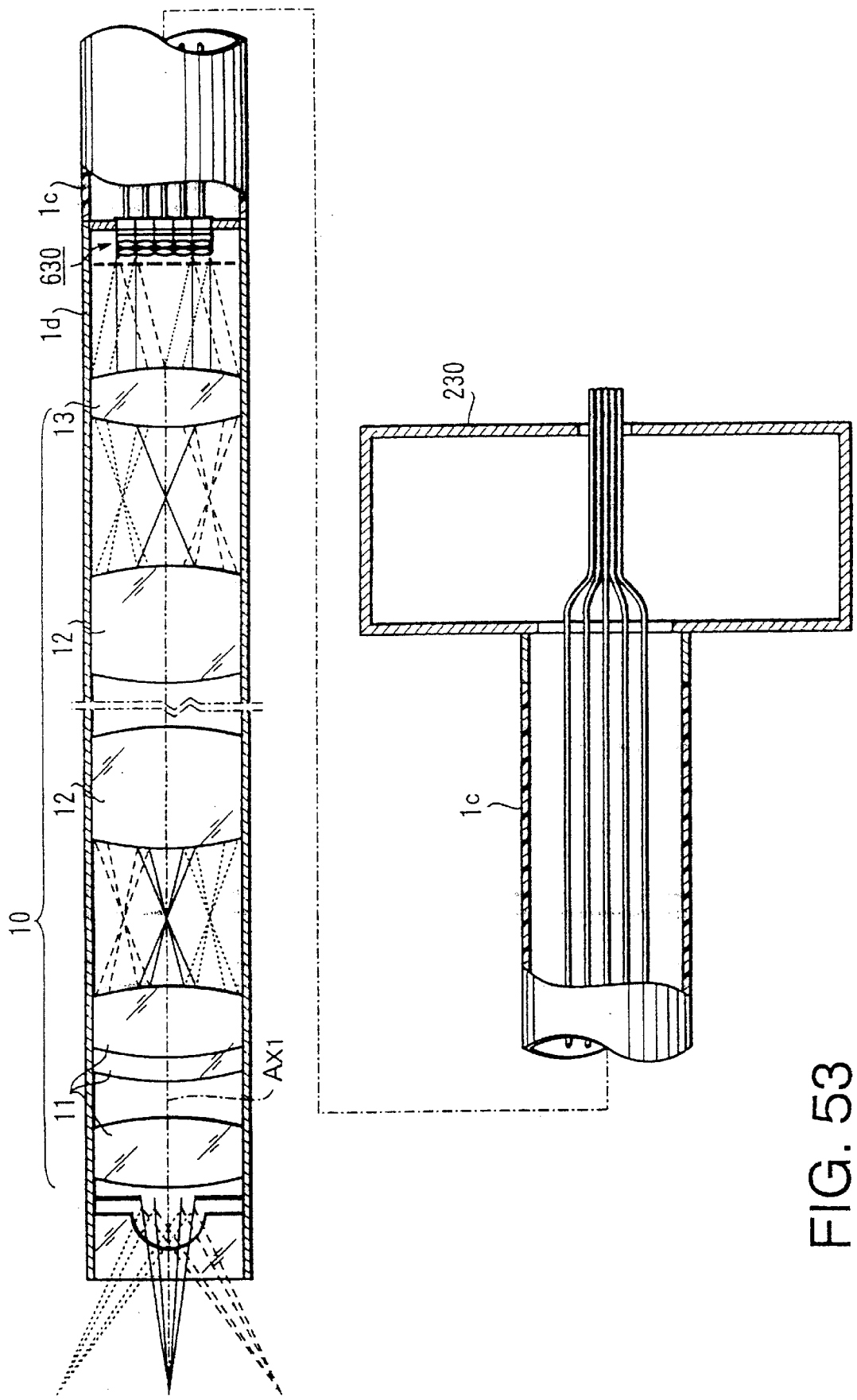
FIG. 53 shows a sectional view of a stereoscopic endoscope according to a thirty-third embodiment of the present invention.

FIG. 53 shows a sectional view of a stereoscopic endoscope according to a thirty-third embodiment of the present invention. The thirty-third embodiment includes an insertion portion 1d, the extension portion 1c, and an observing portion 230.

The insertion portion 1d is similar to the insertion portion 1, with common parts having the same reference numerals. However, the secondary optical system 630 described above, is positioned within the insertion portion 1d. Therefore, the image data output from the secondary optical system 630 is supplied to the observing unit 230, and then processed, by a processing device, such as the processing device 100 for viewing on a monitor.

Thirty-fourth Embodiment

Figure 54:
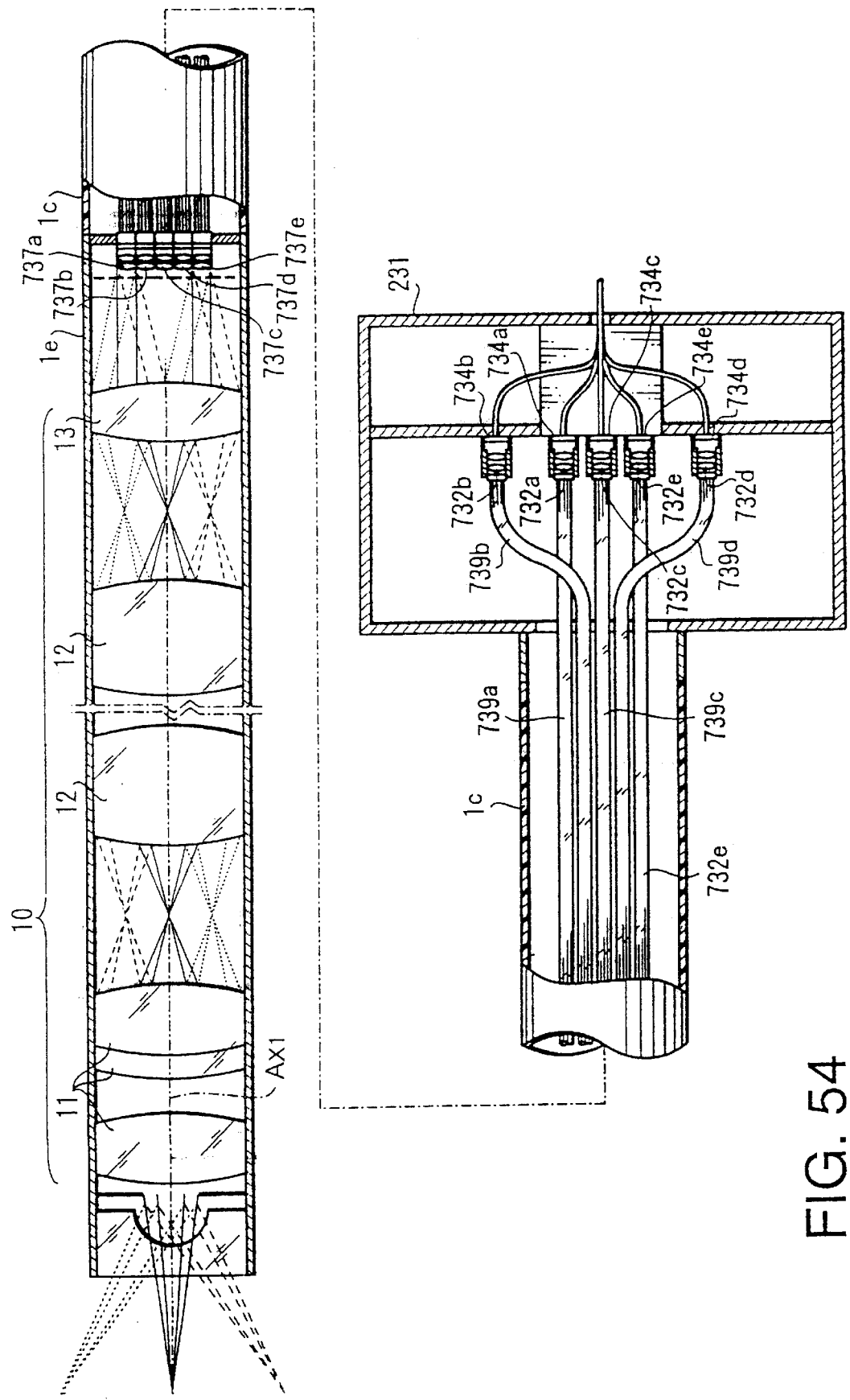
FIG. 54 shows a sectional view of a stereoscopic endoscope according to a thirty-fourth embodiment of the present invention.

FIG. 54 shows a sectional view of a stereoscopic endoscope according to a thirty-fourth embodiment of the present invention. The thirty-fourth embodiment includes an insertion portion 1e, the extension portion 1c and an observing portion 231.

The insertion portion 1e is similar to the insertion portion 1 shown in FIG. 1. However, five separator lenses 737a, 737b, 737c, 737d and 737e are attached to the insertion portion 1e, such that an incident surface of each of the separator lenses 737a through 737e is coincident with a plane of the exit pupil.

Five first ends of five fiber bundles 739a, 739b, 739c, 739d and 739e are attached to the insertion portion 1e, such that each of the first ends contacts a corresponding one of the five separator lenses 737a through 737e. The fiber bundles 739a through 739e transmit the images formed by the separator lenses 737a through 737e to the observing unit 231.

The observing unit 231 includes imaging lenses 732a, 732b, 732c, 732d and 732e, and imaging devices 734a, 734b, 734c, 734d and 734e. The imaging devices 732a through 732e receive light from the fiber bundles 739a through 739e, respectively, and form an image on the imaging devices 734a through 734e, respectively. Image data is output from imaging devices 734a through 734e to a processing device, such as the processing device 100, where a three-dimensional of the image is generated and viewed through a monitor.

Thirty-fifth Embodiment

Figure 55:
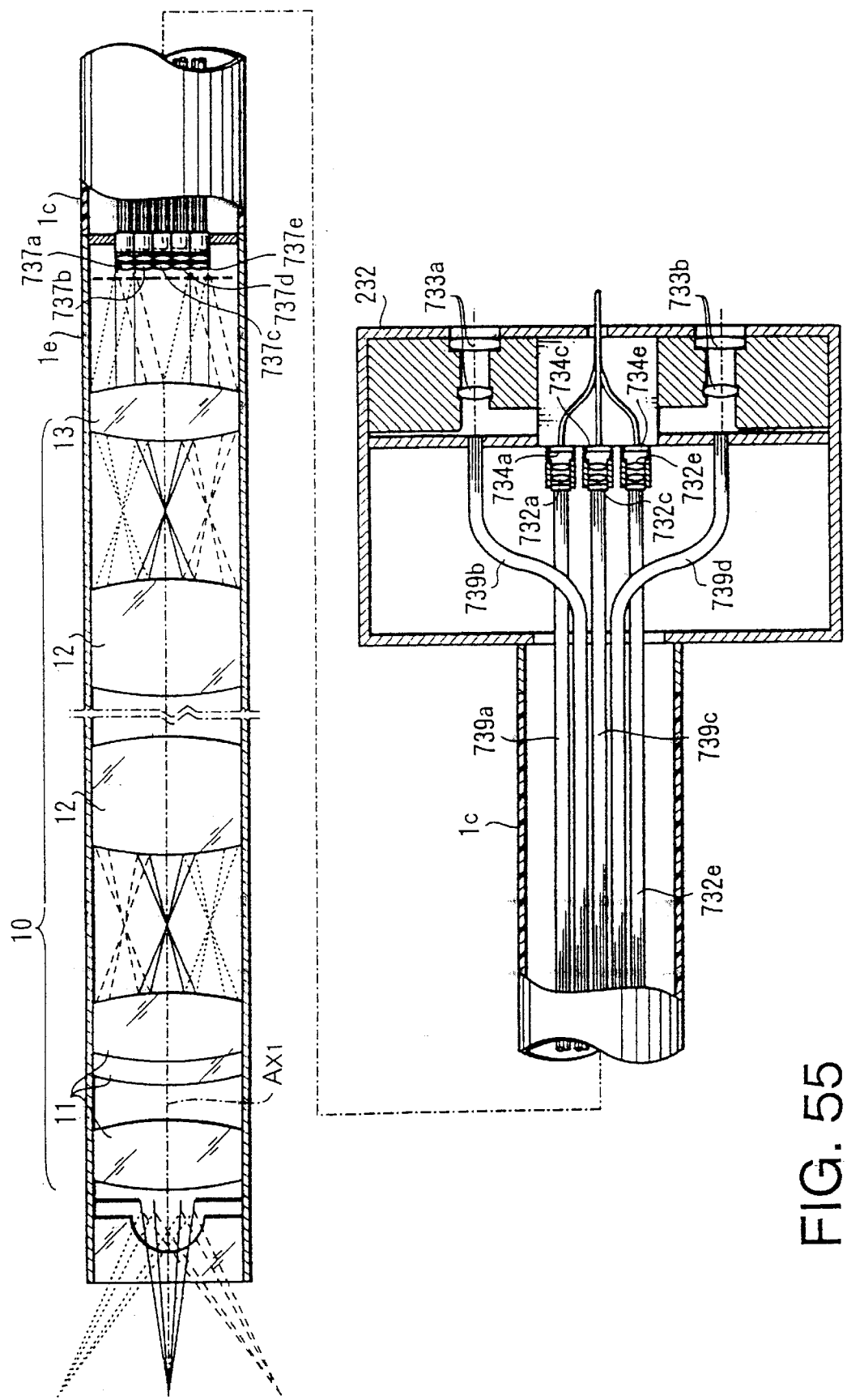
FIG. 55 shows a sectional view of a stereoscopic endoscope according to a thirty-fifth embodiment of the present invention.

FIG. 55 shows a sectional view of a stereoscopic endoscope according to a thirty-fifth embodiment of the present invention. The thirty-fifth embodiment includes the insertion portion 1e, the extension portion 1c and an observing portion 232.

The observing portion 232 is similar to the observing portion 231 described above. However, only the three central separator lenses 732b, 732c and 732d and corresponding imaging devices 734b, 734c and 734d are used.

The images transmitted by the two fiber bundles 739b and 739d are observed by the observer using eyepiece lenses 733a and 733b. Therefore, direct viewing of a three-dimensional image is possible through the eyepiece lenses 733a and 733b. Further, the image signal output by the three imaging devices 734b, 734c and 734d may be processed and viewed on an external monitor.

Thirty-sixth Embodiment

Figure 56A:
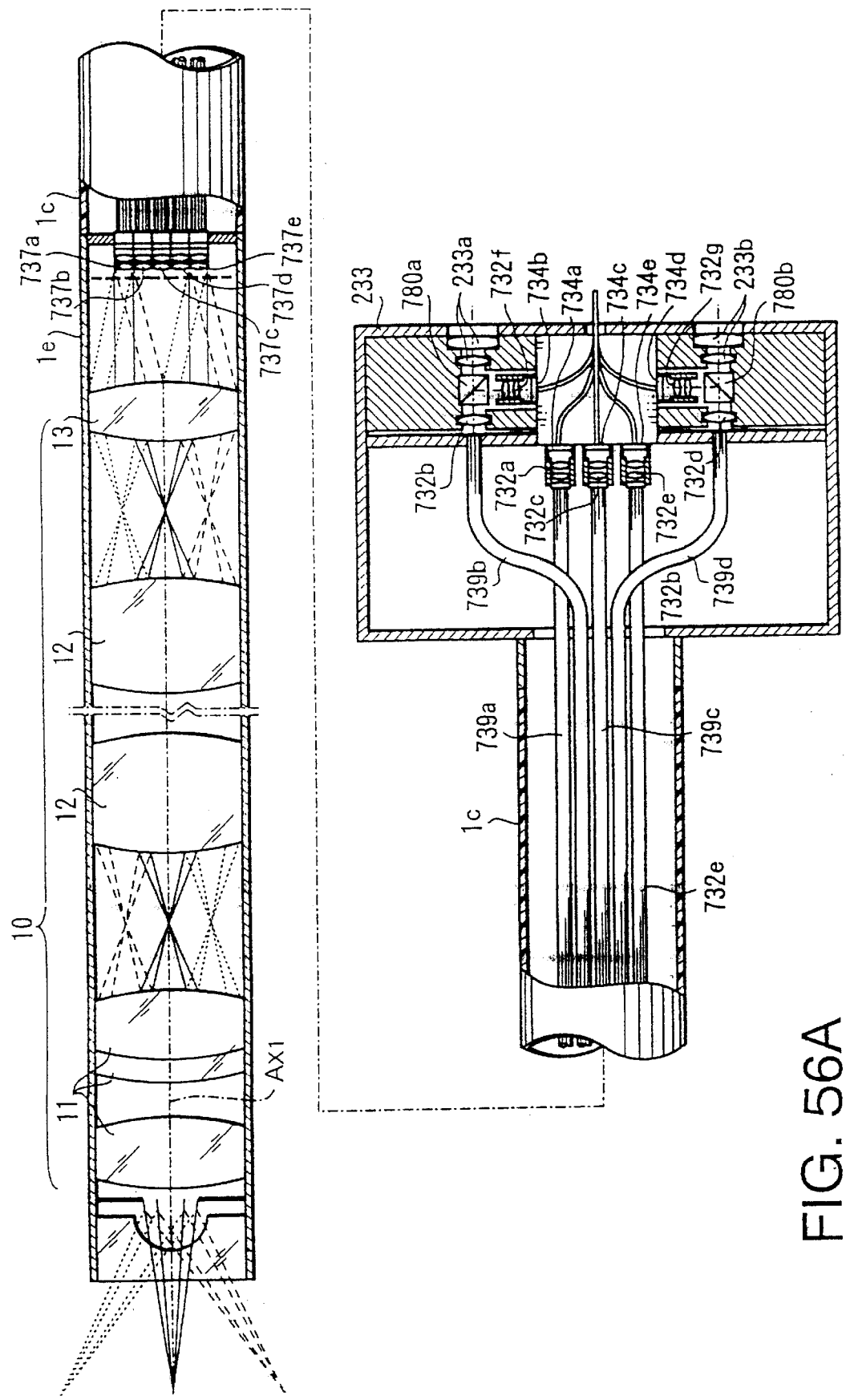
FIG. 56A shows a sectional view of a stereoscopic endoscope according to a thirty-sixth embodiment of the present invention.

FIG. 56A shows a sectional view of a stereoscopic endoscope according to a thirty-sixth embodiment of the present invention. The thirty-sixth embodiment includes the insertion portion 1e, the extension portion 1c and an observing portion 233.

Figure 56B:
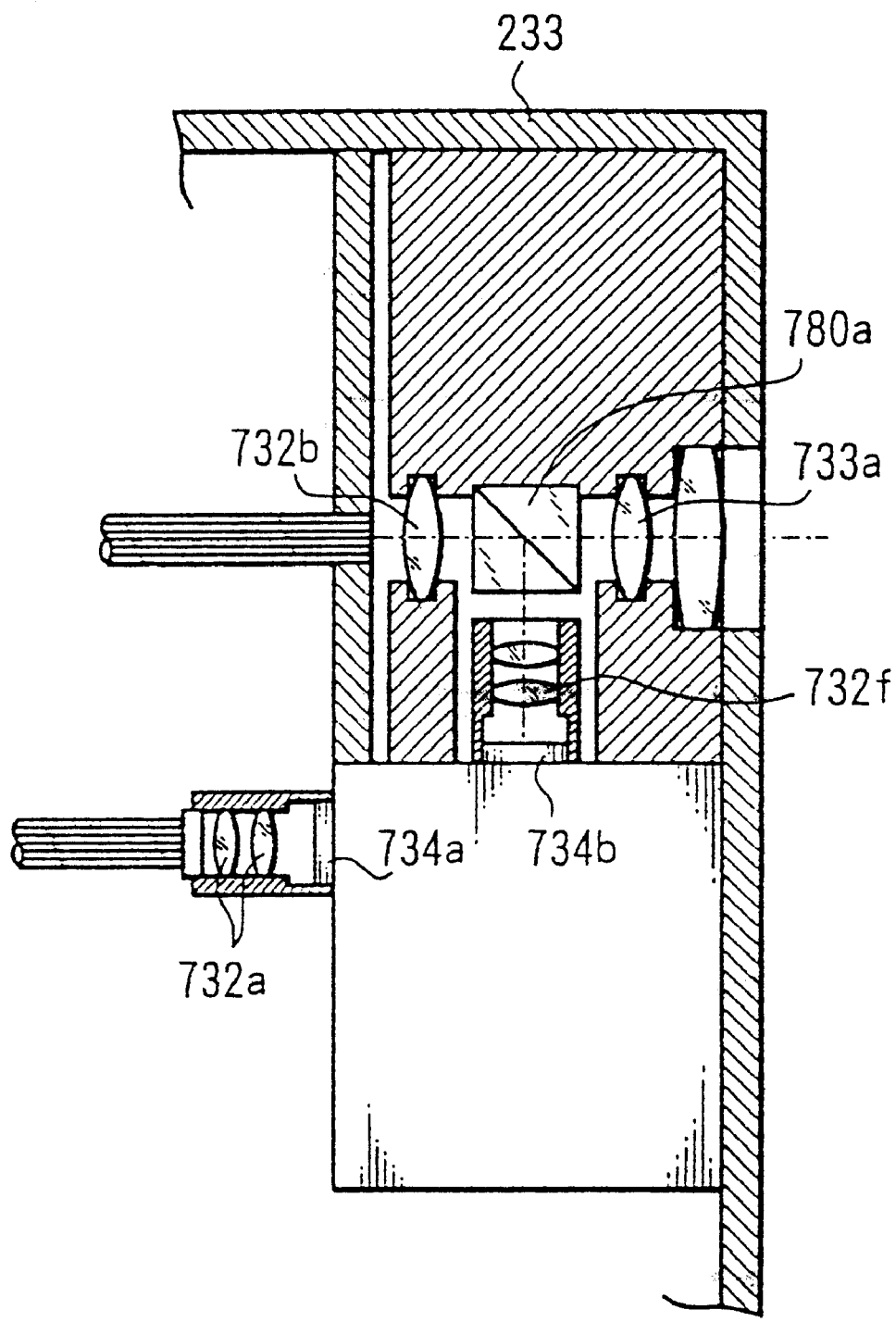
FIG. 56B is an enlarged view of an observing portion of the stereoscopic endoscope shown in FIG. 56A.

The observing portion 233 is similar to the observing portion 232 described above. However, as shown in FIGS. 56A and 56B, the image formed by each of the imaging lenses 732b and 732d is incident on half-mirrors 780a and 780b, respectively.

The half-mirror 780a transmits half of the light to the eyepiece lens 733a, and reflects the other half of the light to the imaging device 734b through an imaging lens 732f. Similarly, the half-mirror 780b transmits half of the light to the eyepiece lens 733b, and reflects the other half of the light to the imaging device 734d through an imaging lens 732g.

With the above construction, the image can be viewed directly through the eyepiece lenses 733a and 733b. Further, all five imaging devices can output image data to a processing device such as the processing device 100.

Thirty-seventh embodiment

Figure 57:
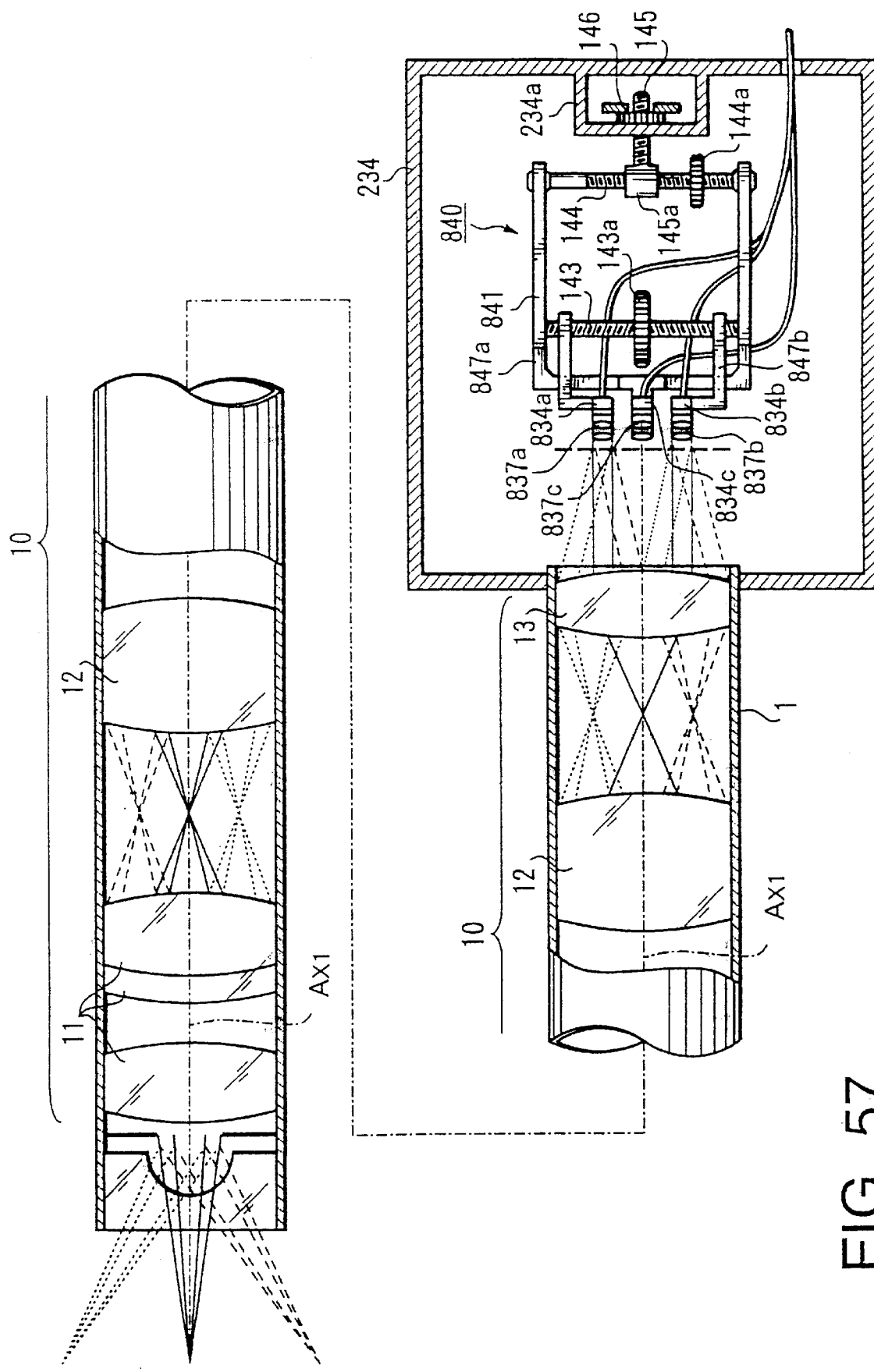
FIG. 57 is a sectional view of a stereoscopic endoscope according to a thirty-seventh embodiment of the present invention.

FIG. 57 shows a sectional view of a stereoscopic endoscope according to a thirty-seventh embodiment of the present invention. The thirty-seventh embodiment includes the insertion portion 1 and an observing portion 234.

The observing portion 234 is similar to the observing portion 230 and includes an adjustment mechanism 840 which is similar to the adjustment mechanism 440 shown in FIG. 47, with the common parts having the same reference numerals. The adjustment mechanism is attached to the wall 234a of the observing mechanism 234.

The observing portion 234 also includes three separator lenses 837a, 837b and 837c for forming images on three corresponding imaging devices 838a, 838b and 838c, in a similar manner to that described above for the previous embodiments.

The separator lens 837a and the imaging device 838a are attached to support 847a, while the separator lens 837b and the imaging device 838b are attached to support 847b. The separator lens 837c and the imaging device 838c are attached to the holding frame 841.

The distance between the separator lenses 837a and 837b is adjusted by rotating the third adjusting gear 143a. Therefore, the three-dimensional effect of image can be varied, as described before. Further, by adjusting screws 144a and 146, the position of the separator lens—imaging device combinations in the x-axis and y-axis directions can be changed simultaneously.

FIGS. 58A, 58B and 58C show the locations of the separator lenses 837a, 837b and 837c in the exit pupil of the primary optical system 10. FIG. 58A shows the condition where the separator lenses 837a, 837b and 837c are located closest to each other (i.e., contacting each other). FIG. 58B shows the condition where the separator lenses 837a, 837b and 837c are located at their maximum distance apart.

FIG. 58C shows the condition in which the separator lenses 837a, 837b and 837c are closest together, but located on one side of the exit pupil. This can be achieved by rotating the adjusting gear 144a in order to move the holding frame 141 in the y-axis direction.

An alternative to the thirty-seventh embodiment uses separator lenses which are designed such that the sum of the diameters of the lenses is equal to the diameter of the exit pupil Ep, as shown in FIG. 58D.

FIGS. 59A through 59D show variations of the arrangement of the separator lenses in the exit pupil Ep. A two dimensional arrangement allows a change in the direction of parallax according to which pair of separator lenses are selected.

If the three separator lenses 837a, 837b, 837c are arranged at vertexes of a triangle as shown in FIG. 59A, one of the three different directions d1, d2 and d3 can be selected as the direction of parallax.

Further, in case four separator lenses (i.e., 837a, 837b, 837c, and 837d) are arranged at ends of a cross as shown in FIG. 59B, one of the two different directions dv and dh can be selected as the direction of parallax.

More separator lenses (such as 837e and 837f) may be arranged as shown in FIGS. 59C and 59D. These two dimensional arrangements of the separator lenses permit a change in the observation direction without changing the direction and/or the angle of the primary optical system 10.

The thirty-eighth through forty-seventh embodiments will be described with reference to FIGS. 60 through 70. In these embodiments, refracting prisms are used in the pupil dividing mechanism.

Thirty-eighth Embodiment

Figure 60:
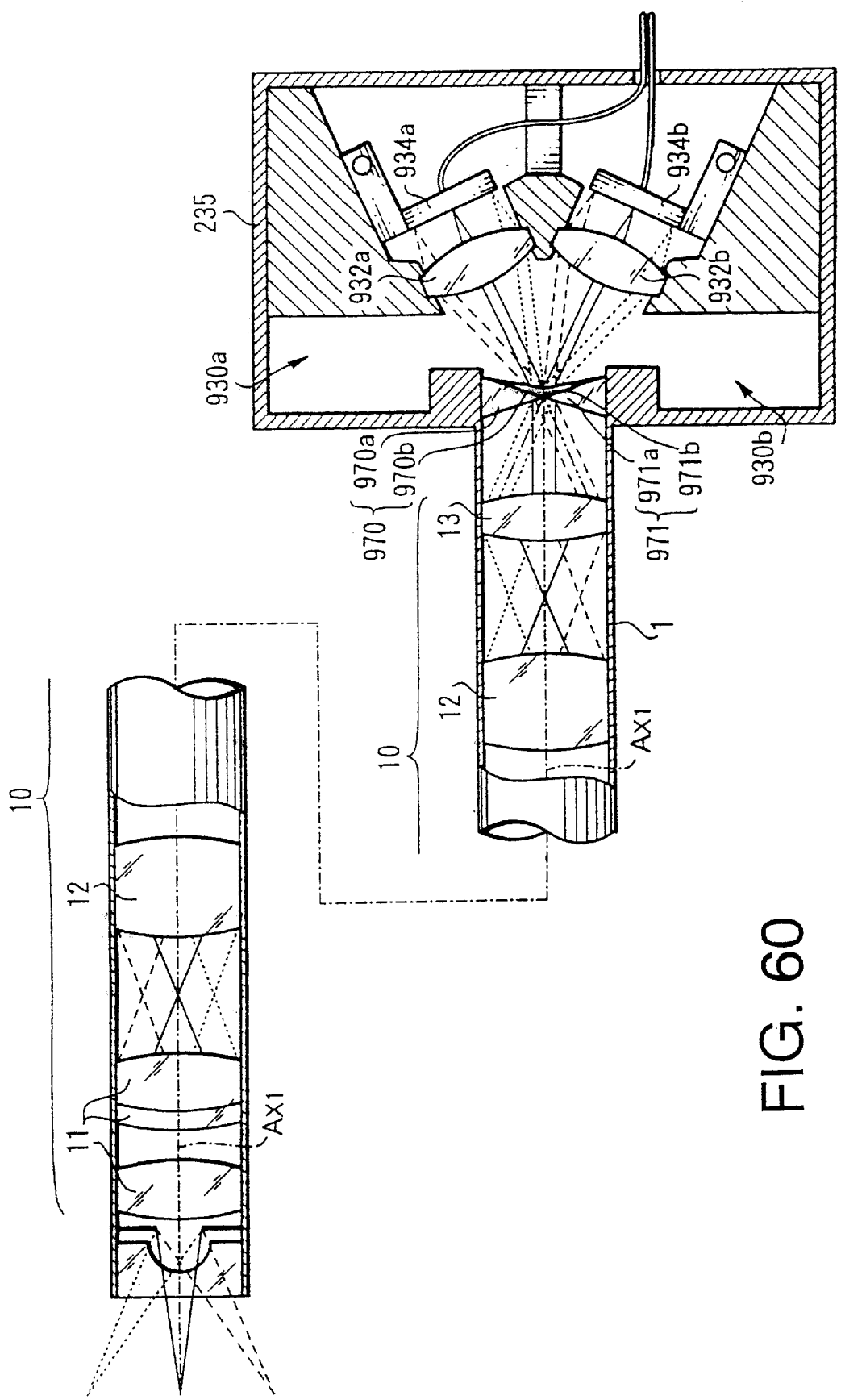
FIG. 60 is a sectional view of a stereoscopic endoscope according to a thirty-eighth embodiment of the present invention.

FIG. 60 shows a sectional view of a stereoscopic endoscope according to a thirty-eighth embodiment of the present invention. The thirty-eighth embodiment includes the insertion portion 1 and an observing portion 235.

The observing portion 235 includes a first secondary optical system 930a, a second optical system 930b, a first prism 970 and a second prism 971. The first prism 970 and the second prism 971 divide the light beam at the exit pupil, into two light beams. One of the divided light beams is refracted towards the first secondary optical system 930a by the first prism 970, while the other light beam is refracted towards the second secondary optical system 930b by the second prism 971.

The first secondary optical system 930a has an imaging lens 932a which receives light from the first prism 970 and forms an image of the object on an imaging device 934a. Similarly, the second secondary optical system 930b has an imaging lens 932b which receives light from the second prism 971 and forms an image of the object on an imaging device 934b.

The first prism 970 and the second prism 971 are wedge-shaped and contact each other at their respective apexes, as shown in FIG. 60. Further, the first prism 970 and the second prism 971 are located in a plane coincident with the exit pupil.

The first prism 970 consists of two prisms 970a and 970b bonded together. Each of the two prisms 970a and 970b has a different refractive index, in order to reduce chromatic aberrations. Similarly, the second prism consists of two prisms 971a and 971b, which have different refractive indexes, bonded together.

The prisms 970a, 970b, 971a, and 971b must satisfy the below noted equations 1 and 2 in order to cancel the chromatic aberration. In equations 1 and 2, "A1" and "A2" denote apex angles of the prisms 970a, 970b, 971a, and 971b, "V1" and "V2" denote Abbe numbers, "N1" and "N2" denote refractive indexes and Dt denotes a composed deviation angle of the two prisms.

$$A_1 = \frac{V_1 \times D_t}{N_1 - 1 \times V_1 - V_2} \quad (1)$$

$$A_2 = \frac{V_2 \times D_t}{N_2 - 1 \times V_2 - V_1} \quad (2)$$

If equations 1 and 2 are satisfied, then the prisms 970a, 970b, 971a, and 971b will be achromatic.

The picture data output from the imaging devices 934a and 934b are processed by a processing device, such as processing device 100, in order to display a three-dimensional picture on a monitor.

Further, the images formed on the imaging devices 934a and 934b include trapezoid distortion due to refraction by the prisms 970, 971. The distortion of the image may be canceled by the well-known affine transformation process.

As described above, the angle between the light beams refracted by each of the prisms 970 and 971 can be minimized. Further, since imaging devices are employed, the secondary optical systems do not have to be parallel. Therefore, the size of the observing portion can be reduced. Furthermore, the number of parts required to construct each of the secondary optical systems can be reduced, since mirrors etc. are not required. This also improves the accuracy of aligning the optical elements used in the observing unit 235.

Thirty-ninth Embodiment

Figure 61:
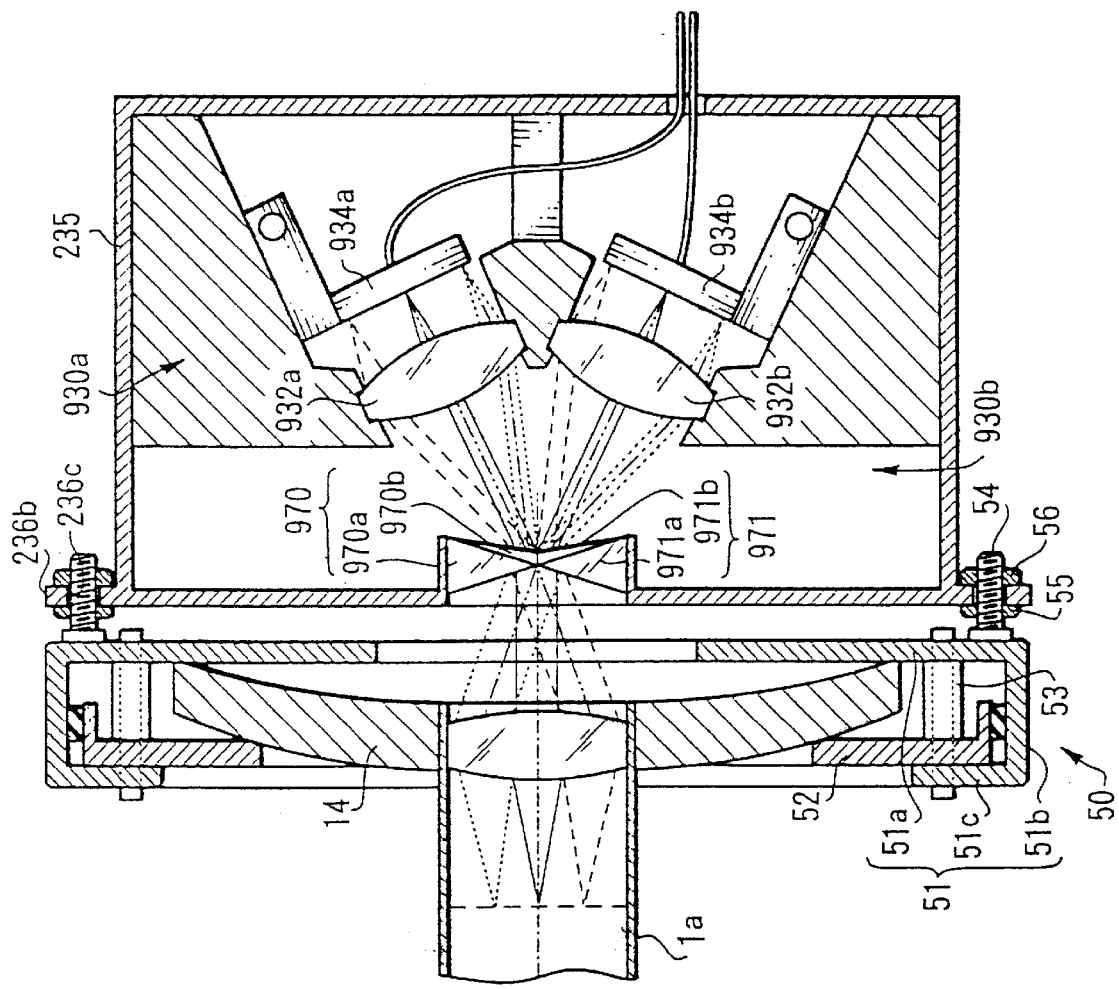
FIG. 61 is a sectional view of an observing portion of a stereoscopic endoscope according to a thirty-ninth embodiment of the present invention.

FIG. 61 shows a sectional view of a stereoscopic endoscope according to a thirty-ninth embodiment of the present invention. The thirty-ninth embodiment includes the insertion portion 1a and an observing portion 236.

The observing portion 236 is similar to the observing portion 235 described above, with common parts having the same reference numerals. The observing portion 236 has a base flange 236b. The base flange 236b has an opening to allow light from the insertion portion 1a to be transmitted to the observing portion 236. Thus, the insertion portion 1a is attached to the hood 14 and the adapter 50. The adapter 50 is then attached to the flange 236b of the observing portion 236 by passing the adjusting bolts 54 through holes 236c and securing the adjusting bolts 54 with nuts 55 and 56, in a similar manner to that described for the fifth embodiment above.

Fortieth Embodiment

Figure 62:
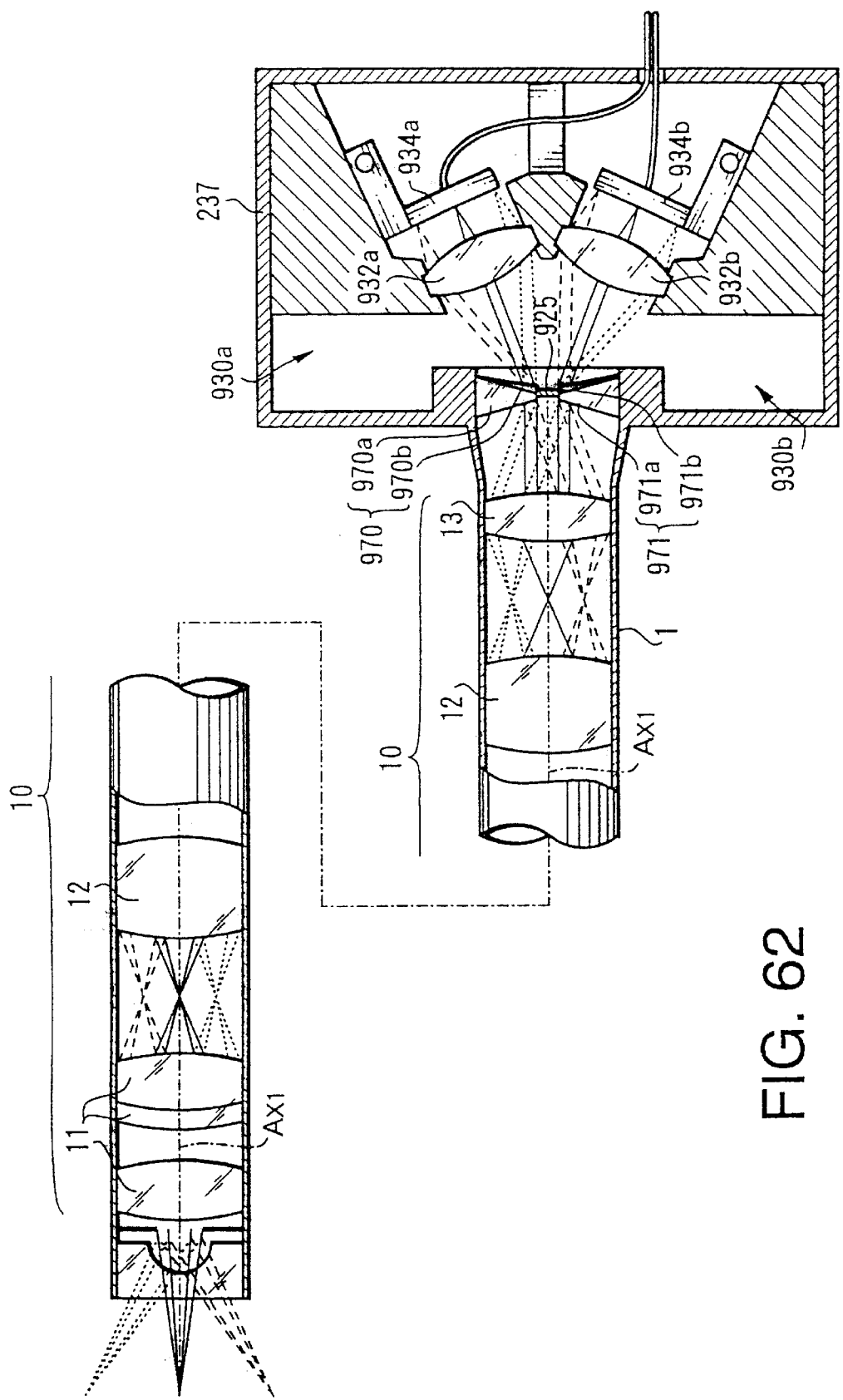
FIG. 62 is a sectional view of a stereoscopic endoscope according to a fortieth embodiment of the present invention.

FIG. 62 shows a sectional view of a stereoscopic endoscope according to a fortieth embodiment of the present invention. The fortieth embodiment includes the insertion portion 1 and an observing portion 237.

The observing portion 237 is similar to the observing portion 235 described above in the thirty-eighth embodiment, with common parts having the same reference numerals. In the observing portion 237, the first prism 970 is separated from the second prism 971 by a shading plate 925. This results in the distance between the incident axes of the first and second light beams being separated. This will increase the three-dimensional effect of the image detected by the imaging devices 934a and 934b, in a manner similar to that described for the previous embodiments.

Figure 63:
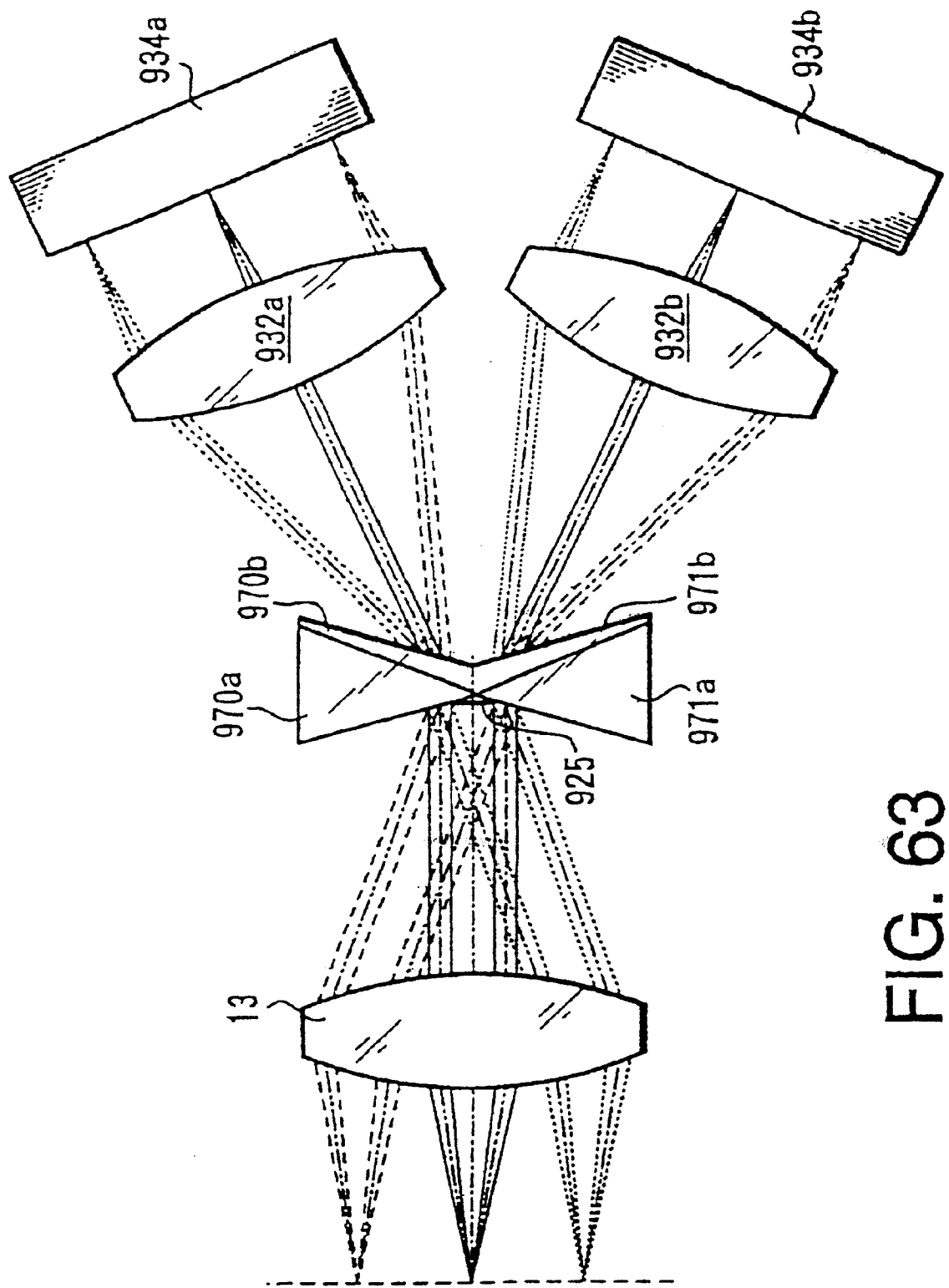
FIG. 63 is an enlarged view of an observing portion of the stereoscopic endoscope shown in FIG. 62.

FIG. 63 shows a modification of the arrangement of the first prism 970, the second prism 971 and the shading plate 925 shown in the fortieth embodiment. In this modification, the first prism 970 contacts the second prism 971 at the apex. However, the shading plate 925 is positioned to block light incident on an area of the two prisms 970 and 971 around the point where the prisms contact each other.

Forty-first Embodiment

Figure 64:
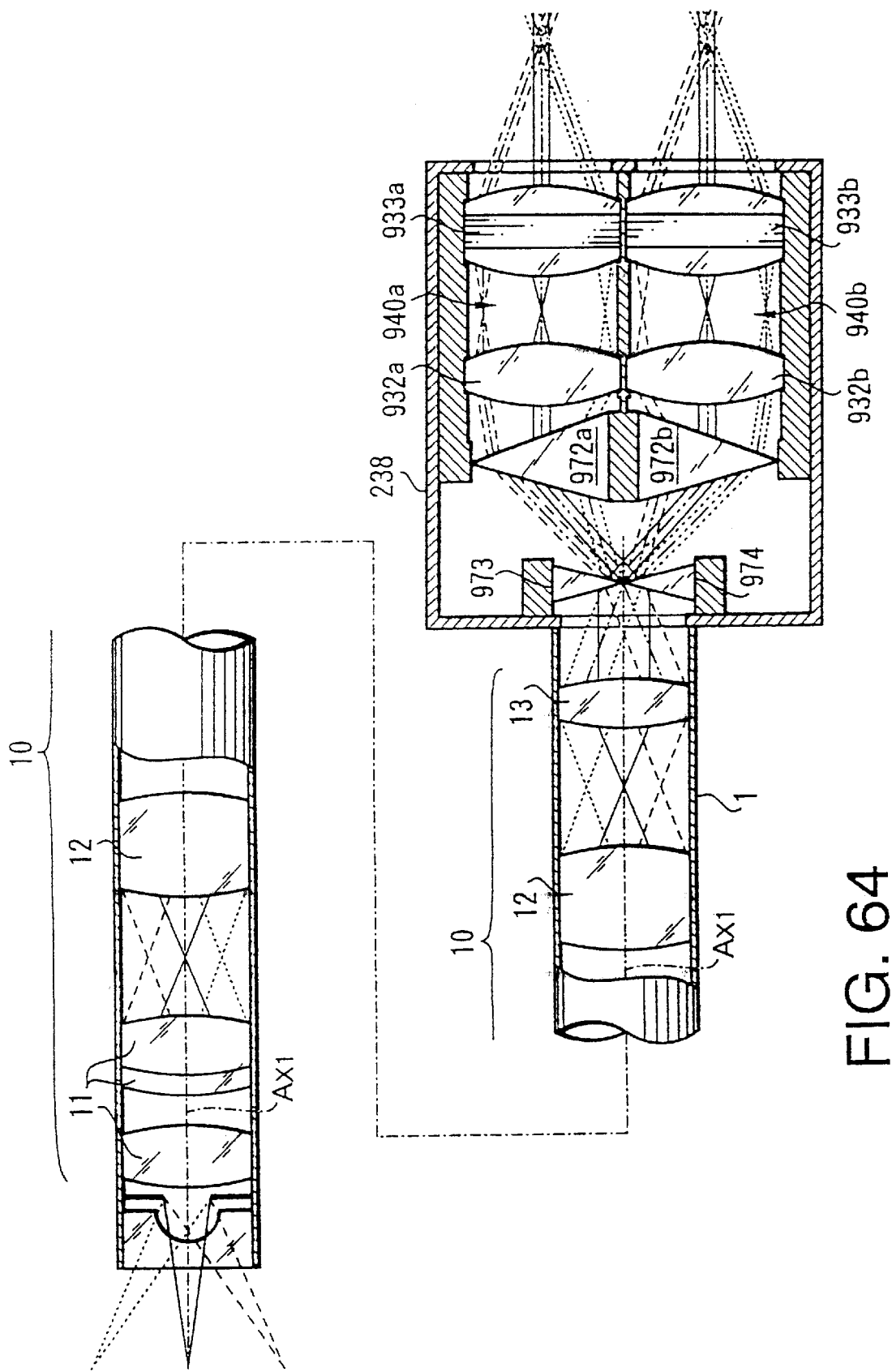
FIG. 64 is a sectional view of a stereoscopic endoscope according to a forty-first embodiment of the present invention.

FIG. 64 shows a sectional view of a stereoscopic endoscope according to a forty-first embodiment of the present invention. The forty-first embodiment includes the insertion portion 1 and an observing portion 238.

The observing portion 238 allows direct viewing of a three-dimensional image of the object. The observing portion has a first secondary optical system 940a, a second secondary optical system 940b, a first prism 973 and a second prism 974.

The first secondary optical system 940a includes the imaging lens 932a, an eyepiece lens 933a, and a deflecting prism 972a. Similarly, the secondary optical system 940b includes the imaging lens 932b, an eyepiece lens 933b, and a deflecting prism 972b.

The first prism 973 and the second prism 974 are arranged to contact each other at their respective apexes, in a similar manner to that described for the prisms 970 and 971, in the thirty-eighth embodiment.

The light beams refracted by each of the prisms 970 and 971, are refracted by the prisms 972a and 972b, such that the refracted light beams are made parallel to the optical axis Ax1, towards the imaging lenses 932a and 932b. The lenses 932a and 932b form left and right images which are viewed using the eyepiece lenses 933a and 933b, respectively.

In the forty-first embodiment, the first prism 973 and the second prism 974 are not formed of separate prisms bonded together, since the chromatic aberrations of the prisms 973 and 974 will be canceled by the chromatic aberrations of the deflecting prisms 972a and 972b. Further, there is no trapezoidal distortion of the image viewed through the eyepiece lenses 933a and 933b, and therefore the affine transformation is not required.

Forty-second Embodiment

Figure 65:
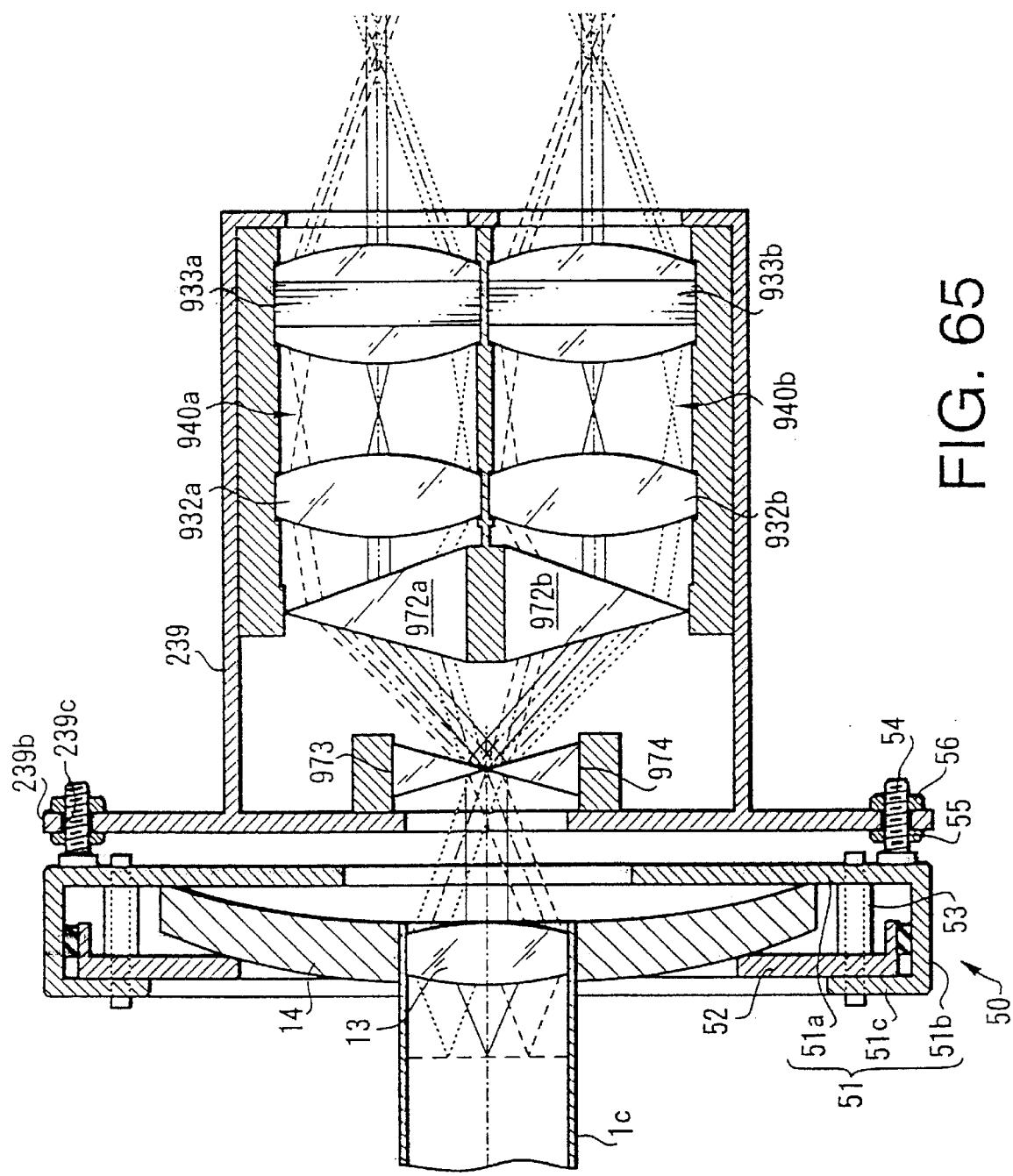
FIG. 65 is a sectional view of an observing portion of stereoscopic endoscope according to a forty-second embodiment of the present invention.

FIG. 65 shows a sectional view of a stereoscopic endoscope according to a forty-second embodiment of the present invention. The forty-second embodiment includes the insertion portion 1a and an observing portion 239.

The observing portion 239 is similar to the observing portion 238 described above, with common parts having the same reference numerals. The observing portion 239 has a base flange 239b. The base flange 239b has an opening to allow light from the insertion portion 1a to be transmitted to the observing portion 239. The insertion portion 1a is attached to the hood 14. The hood 14 is securely fastened to the adapter 50, and the adapter 50 is attached to the base flange 239b, in a similar manner to that described for the fifth embodiment above.

Forty-third Embodiment

Figure 66:
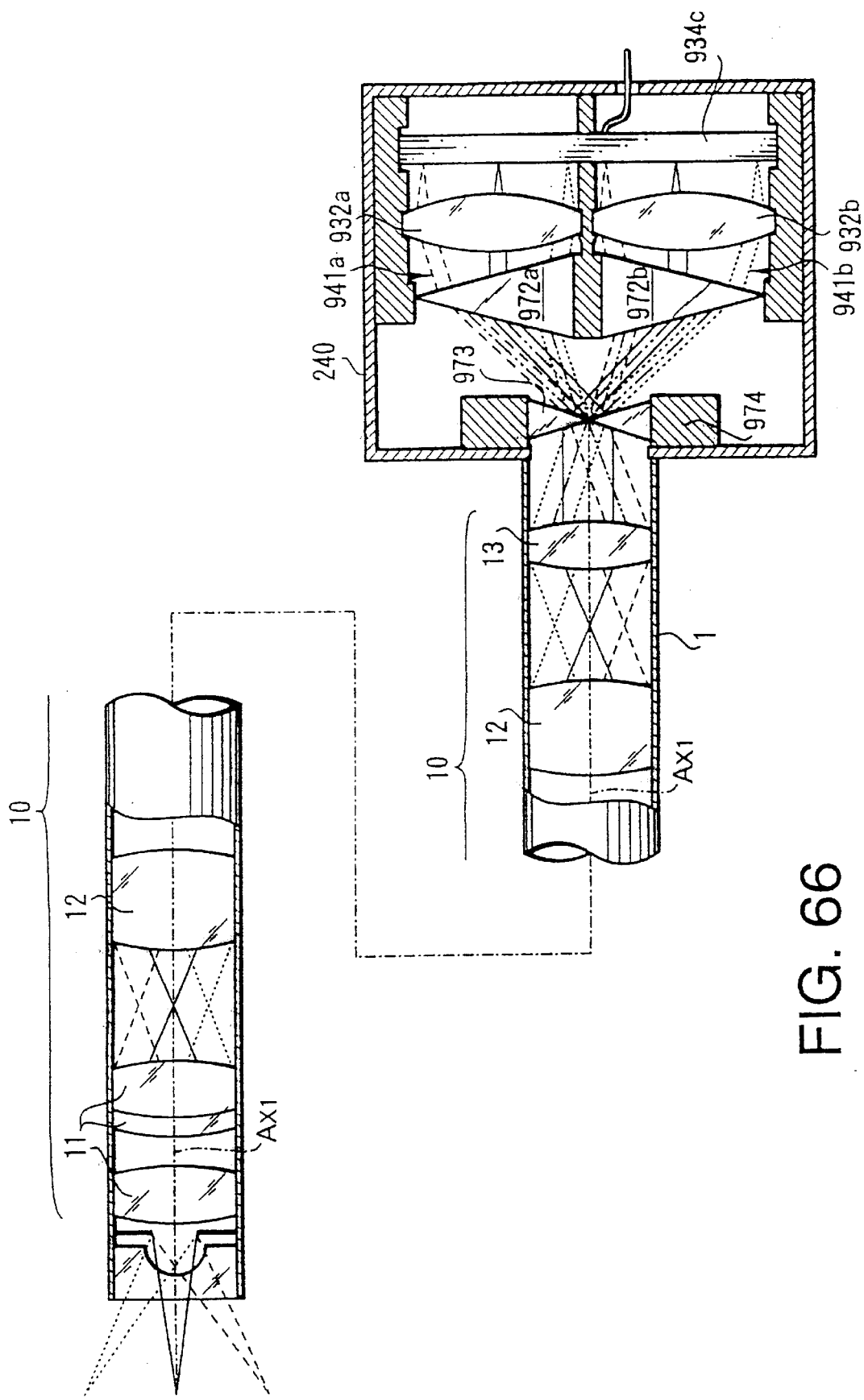
FIG. 66 shows a sectional view of a stereoscopic endoscope according to a forty-third embodiment of the present invention.

FIG. 66 shows a sectional view of a stereoscopic endoscope according to a forty-third embodiment of the present invention. The forty-third embodiment includes the insertion portion 1 and an observing portion 240.

The observing portion 240 has a first secondary optical system 941a, a second secondary optical system 941b, the first prism 973 and the second prism 974.

The first secondary optical system 941a includes the deflecting prism 972a and the imaging lens 932a which forms a left image on a portion of an imaging device 934c. Similarly, the secondary optical system 940b includes the deflecting prism 972b, and the imaging lens 932b which forms a right image on another portion of the imaging device 934c.

The left and right images that are formed on separate areas of the imaging device 934c do not overlap. Therefore, the image data that is output by the imaging device 934c can be processed by a processing device such as the processing device 100, and separated into left image data and right image data. Then, by alternately displaying the left and right images on the monitor 190 and wearing the pair of glasses 191, an observer can view a three-dimensional image.

Forty-fourth Embodiment

Figure 67:
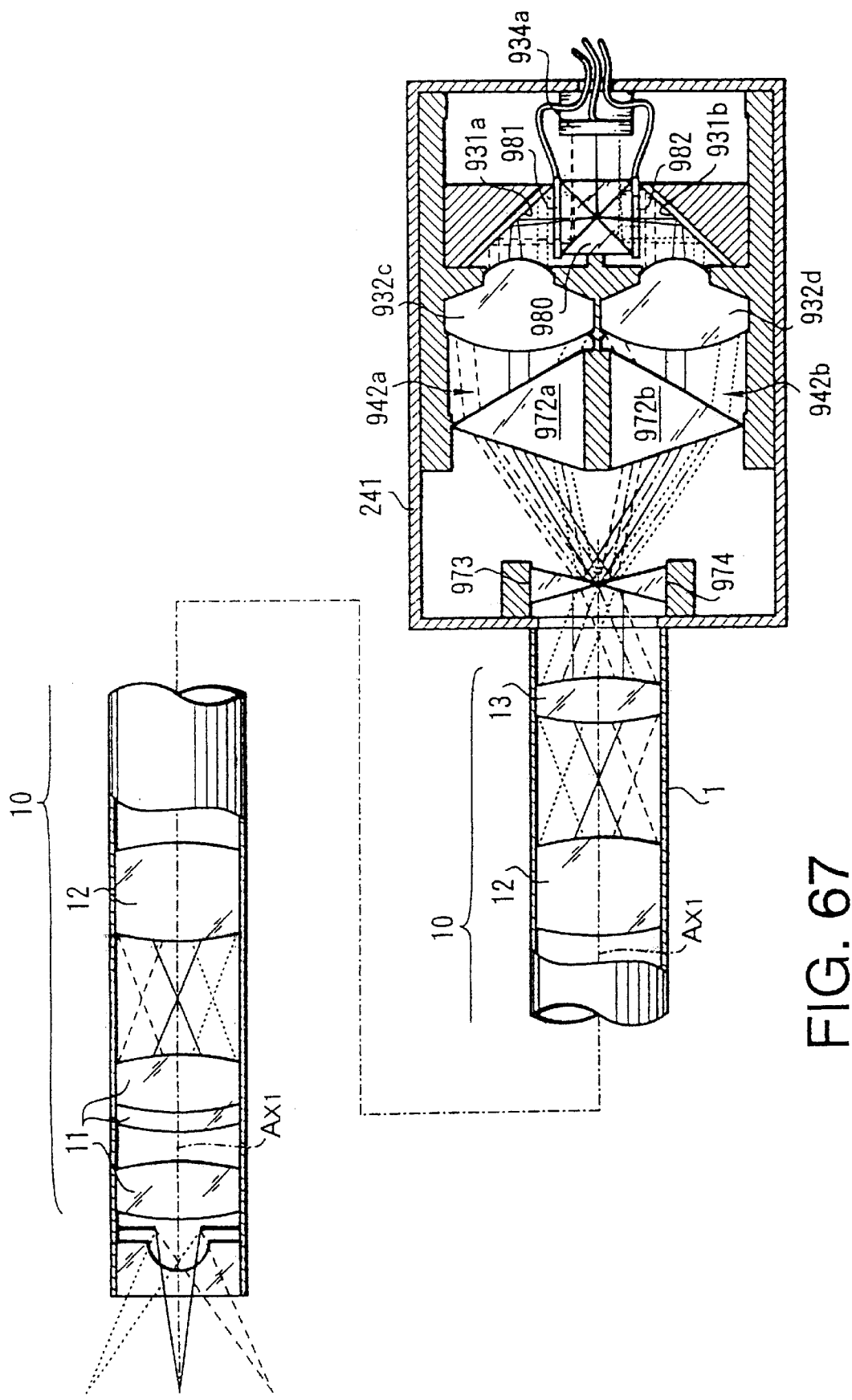
FIG. 67 shows a sectional view of a stereoscopic endoscope according to a forty-fourth embodiment of the present invention.

FIG. 67 shows a sectional view of a stereoscopic endoscope according to a forty-fourth embodiment of the present invention. The forty-fourth embodiment includes the insertion portion 1 and an observing portion 241.

The observing portion 241 has a first secondary optical system 942a, a second secondary optical system 942b, the first prism 973 and the second prism 974, a half mirror prism 980, a first liquid crystal shutter 981, a second liquid crystal shutter 982, and an imaging device 934a.

The first secondary optical system 942a includes a deflecting prism 972c, an imaging lens 932c, and a mirror 931a. Similarly, the secondary optical system 942b includes a deflecting prism 972d, an imaging lens 932d, and a mirror 931b. The imaging lenses 932c and 932d have a different shape than the imaging lenses 932a and 932b, since the distance between the imaging lenses 932c and 932d and the imaging device 934a, is longer than the distance between the imaging lenses 932a and 932b and the imaging device 934c.

The deflecting prisms 972c and 972d have the same function as the prisms 972a and 972b, of the previous embodiments, however the shape of the prisms 972c and 972d is slightly different than the shape of the prisms 972a and 972b in order to accommodate the change in the shape of the imaging lenses 932c and 932d, respectively.

Thus, light which enters the exit pupil of the insertion portion 1 is split by the prisms 973 and 974 and refracted to the optical systems 942a and 942b. The light which is transmitted by the optical system 942a is reflected by the mirror 931a, through the liquid crystal shutter 981 to be incident on the half mirror prism 980. Half of the light is reflected by the half mirror prism 980 towards the imaging device 934a, where the left image is detected and the left image data is output. When the left image data is being detected, the shutter 982 is made opaque, thereby blocking the right image from interfering with the left image.

Similarly, the light which is transmitted by the optical system 942b is reflected by the mirror 931b, through the liquid crystal shutter 982 to be incident on the half mirror prism 980. Half of the light is reflected by the half mirror prism 980 towards the imaging device 934a, where the right image is detected and the right image data is output. Further, when the right image data is being detected, the shutter 981 is made opaque, thereby blocking the left image from interfering with the right image.

The left and right images are formed on overlapping portions of the imaging device 934a. Therefore, by controlling the shutters 982 and 981 to be alternately opaque and transparent, the left and right image data can be detected by the imaging device 934a and output to a processing device, such as the processing device 100, for viewing on a monitor using the pair of glasses 191.

As described above, the imaging device 934a is half the size of the imaging device 934c. Therefore, the cost of manufacturing the stereoscopic endoscope can be reduced.

Forty-fifth Embodiment

Figure 68:
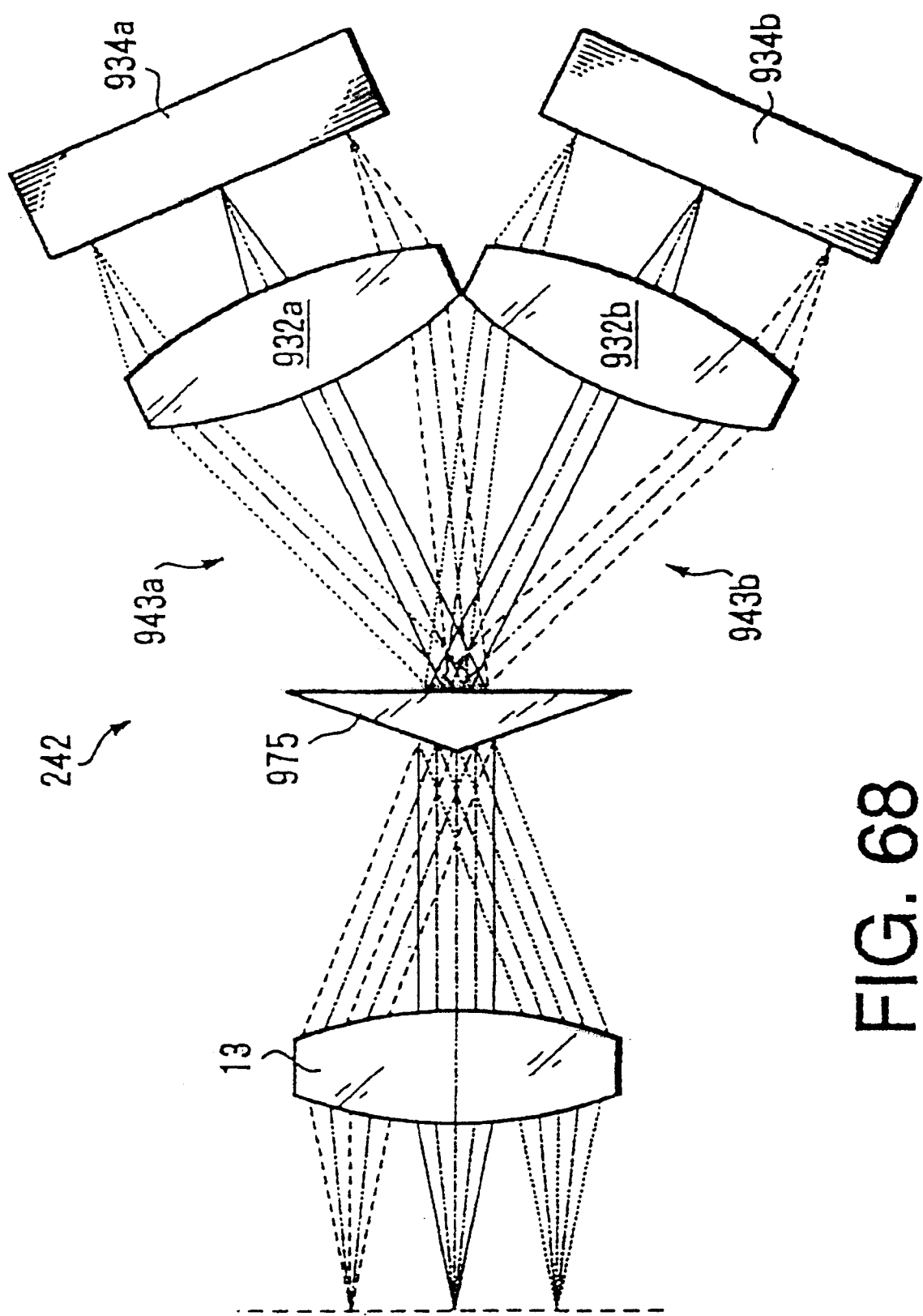
FIG. 68 is an enlarged view of an observing portion of a stereoscopic endoscope according to a forty-fifth embodiment of the present invention.

FIG. 68 shows a first secondary optical system 943a, a second secondary optical system 943b, and a roof prism 975 of an observing portion 242, and an imaging lens 13 of the insertion portion 1 of a stereoscopic endoscope according to a forty-fifth embodiment of the present invention.

As shown in FIG. 68, the thickness of the roof prism 975 is a maximum at the center thereof, and gradually decreases towards each end. The roof prism 975 has two incident surfaces 975a and 975b. Light which is incident on the incident surface 975a is refracted towards the first secondary optical system 943a, thereby forming an image on the imaging device 934a. Similarly, light which is incident on the incident surface 975b is refracted towards the second secondary optical system 943b, thereby forming an image on the imaging device 934b.

The refraction of the light by the roof prism 975 introduces a trapezoidal distortion into the images formed on the imaging devices 934a and 934b. Therefore, the image data output by the imaging devices 934a and 934b should be processed with the affine transform in order to remove the trapezoidal distortion. Further, by processing with the processing device 100, a three-dimensional image may be viewed on the monitor 190 using the pair of glasses 191.

Forty-sixth Embodiment

Figure 69:
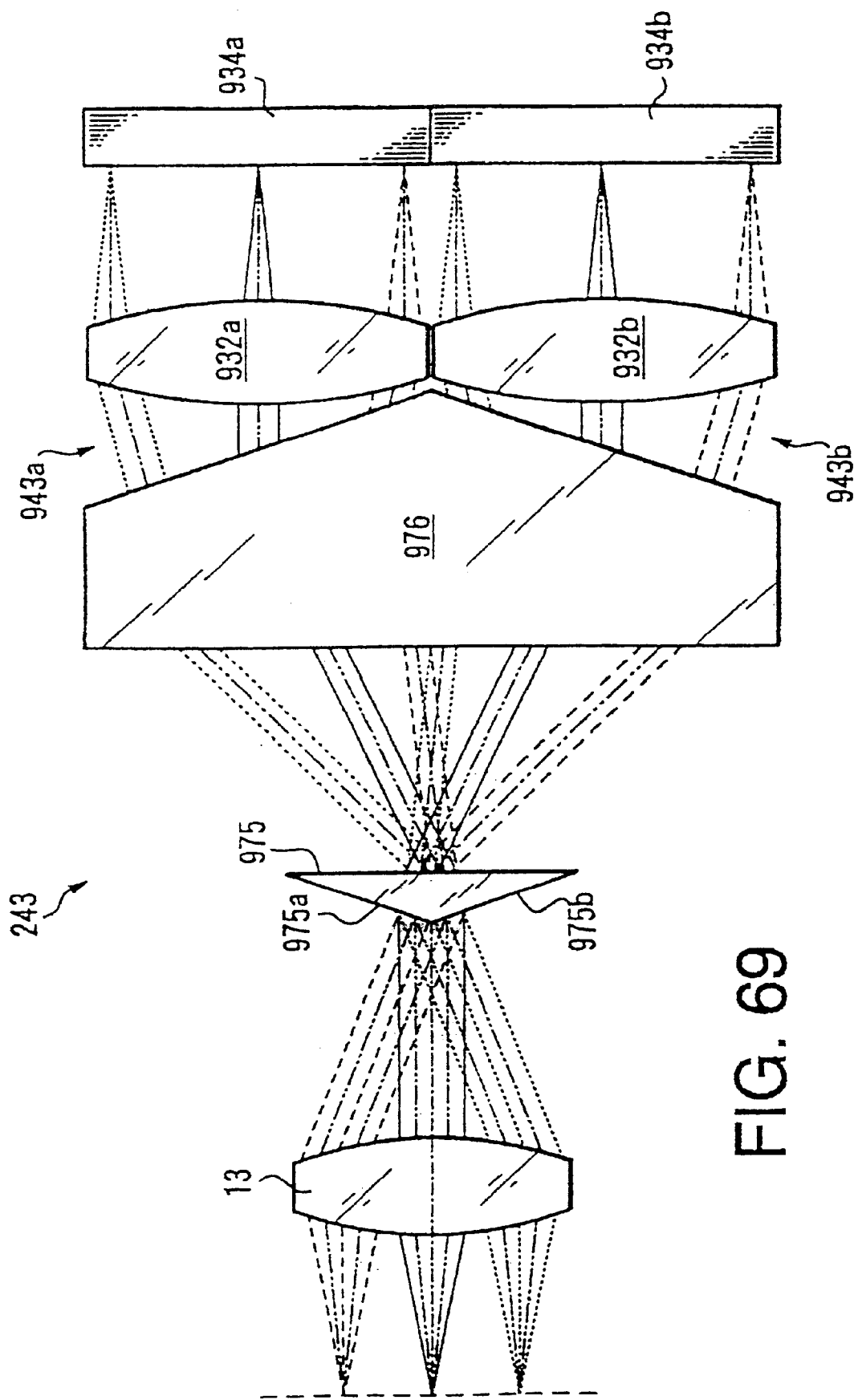
FIG. 69 is an enlarged view of an observing portion of a stereoscopic endoscope according to a forty-sixth embodiment of the present invention.

FIG. 69 shows an observing portion 243, and an imaging lens 13 of the insertion portion 1 of a stereoscopic endoscope according to a forty-sixth embodiment of the present invention.

The observing portion 243 is similar to the observing portion 242 described above, with common parts having the same reference numerals. The observing portion 219 includes a deflecting prism 976 located between the first and second secondary optical systems 943a and 943b and the roof prism 975. The apex of the deflecting prism 976 has the same angle as the apex of the roof prism 975. Therefore, the chromatic aberrations and trapezoidal distortion introduced into the light beams refracted by the roof prism 975 is canceled by the deflecting prism 976. The left and right images detected by the imaging devices 934a and 934b, can be processed normally using the processing device 100, and a three-dimensional image can be viewed on the monitor 190 using the pair of glasses 191.

Forty-seventh Embodiment

Figure 70:
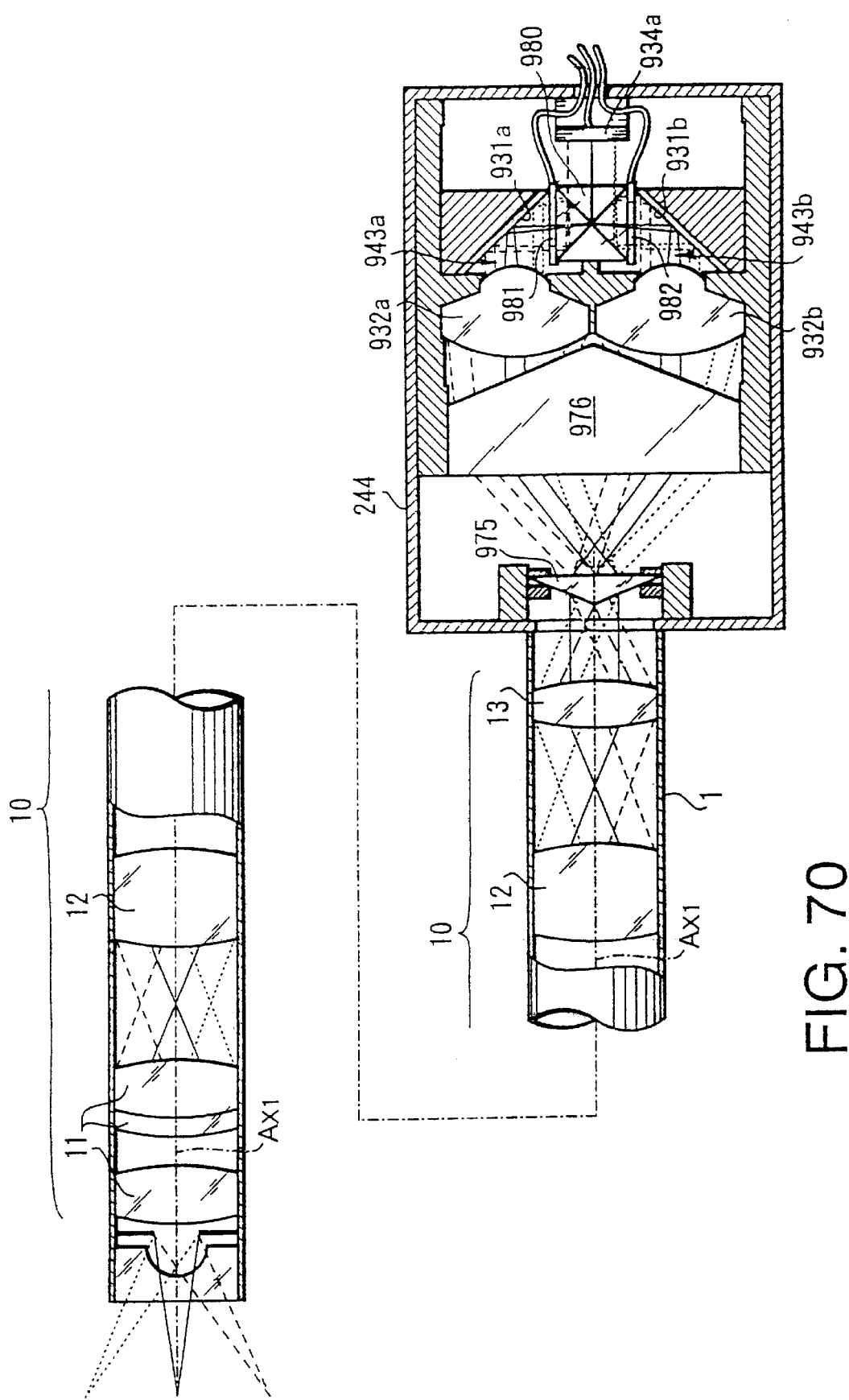
FIG. 70 is a sectional view of a stereoscopic endoscope according to a forty-seventh embodiment of the present invention.

FIG. 70 shows a sectional view of a stereoscopic endoscope according to a forty-seventh embodiment of the present invention. The forty-seventh embodiment includes the insertion portion 1 and an observing portion 244.

The observing portion 244 has a first secondary optical system 944a, a second secondary optical system 944b, the roof prism 975 and the deflecting prism 976, the half mirror prism 980, the first liquid crystal shutter 981, the second liquid crystal shutter 982, and the imaging device 934d.

The first secondary optical system 944a includes the imaging lens 932a and the mirror 931a. Similarly, the secondary optical system 944b includes the imaging lens 932b and the mirror 931b.

Thus, light which enters the exit pupil of the insertion portion 1 is split by the roof prism 975 and refracted by the deflecting prism 976 and to the optical systems 944a and 944b. The light which is transmitted by the optical system 944a is reflected by the mirror 931a, through the liquid crystal shutter 981 to be incident on the half mirror prism 980. Half of the light is reflected by the half mirror prism 980 towards the imaging device 934d, where the left image is detected and the left image data is output. When the left image data is being detected, the shutter 982 is made opaque, thereby blocking the right image from interfering with the left image.

Similarly, the light which is transmitted by the optical system 944b is reflected by the mirror 931b, through the liquid crystal shutter 982 to be incident on the half mirror prism 980. Half of the light is reflected by the half mirror prism 980 towards the imaging device 934d, where the right image is detected and the right image data is output. Further, when the right image data is being detected, the shutter 981 is made opaque, thereby blocking the left image from interfering with the right image.

The left and right images are formed on overlapping portions of the imaging device 934d. Therefore, by controlling the shutters 982 and 981 to be alternately opaque and transparent, the left and right image data can be detected by the imaging device 934d and output to a processing device, such as the processing device 100, for viewing on a monitor using the pair of glasses 191.

As described above, the imaging device 934d is half the size of the imaging device 934c. Therefore, the cost of the stereoscopic endoscope can be reduced.

The present disclosure relates to subject matter contained in Japanese patent application Nos. Hei 6-319300 (filed on Nov. 29, 1994), Hei 6-331229 (filed on Dec. 8, 1994), Hei 6-340053 (filed on Dec. 28, 1994), Hei 6-340055 (filed on Dec. 28, 1994), Hei 7-44779 (filed on Feb. 9, 1995), Hei 7-50613 (filed on Feb. 15, 1995), Hei 7-61749 (filed on Feb. 24, 1995), Hei 7-136043 (filed on May 10, 1995) and Hei 7-191143 (filed on Jul. 4, 1995) which are expressly incorporated herein by references in their entireties.

What is claimed:

1. A stereoscopic observing apparatus for use with a monocular endoscope comprising:

an observing portion comprising a system that divides light transmitted by the monocular endoscope into two light beams, and a pair of optical systems, each of said optical systems receiving one of said light beams and forming an image of an object, said images formed by each of said optical systems forming a stereoscopic image of the object; and an adapter, said adapter comprising a system that connects said observing portion to the monocular endoscope, said connecting system comprising an adjusting system that adjusts a positional relationship of said observing portion and the monocular endoscope, said adjusting system further comprising:

a first set of screws oriented along a first direction, said first set of screws adjusting a position of said adapter relative to said observing portion along said first direction; and a second set of screws, oriented along a second direction, said second set of screws adjusting a position of said adapter relative to said observing portion along said second direction, said second direction being perpendicular to said first direction.

2. The stereoscopic observing apparatus according to claim 1, said adjusting system further comprising:

a first motor system that rotates said first set of screws; and a second motor system that rotates said second set of screws, a position of said adapter relative to said observing portion being adjusted in response to a driving of said first motor system and a driving of said second motor system.

3. The stereoscopic observing apparatus according to claim 1, said connecting system of said adapter further comprising at least one clamp that is configured to mount said adapter to a flange of the monocular endoscope.

4. The stereoscopic observing apparatus according to claim 3, said adapter comprising a holding ring, said at least one clamp being attached to said holding ring, at least one bolt attached to said holding ring and to said at least one clamp, said at least one clamp securing said holding ring to the flange of the monocular endoscope.

* * * * *